United States Patent
Alcaraz et al.

(10) Patent No.: US 9,573,949 B2
(45) Date of Patent: *Feb. 21, 2017

(54) DERIVATIVES OF [1, 2, 4] TRIAZOLO [4, 3-A] PYRIDINE AS P38—MAP KINASE INHIBITORS

(71) Applicant: CHIESI FARMACEUTICI S.P.A., Parma (IT)

(72) Inventors: Lilian Alcaraz, Harlow (GB); Terry Aaron Panchal, Harlow (GB); Andrew Stephen Robert Jennings, Harlow (GB); Andrew Peter Cridland, Harlow (GB); Christopher Hurley, Harlow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/895,718

(22) PCT Filed: Jun. 6, 2013

(86) PCT No.: PCT/EP2013/061706
§ 371 (c)(1),
(2) Date: Dec. 3, 2015

(87) PCT Pub. No.: WO2014/194956
PCT Pub. Date: Dec. 11, 2014

(65) Prior Publication Data
US 2016/0108040 A1    Apr. 21, 2016

(51) Int. Cl.
*A61K 31/437*    (2006.01)
*C07D 471/04*    (2006.01)
*C07D 519/00*    (2006.01)

(52) U.S. Cl.
CPC .......... *C07D 471/04* (2013.01); *C07D 519/00* (2013.01)

(58) Field of Classification Search
USPC .......................................... 514/303; 546/119
See application file for complete search history.

(56) References Cited

U.S. PATENT DOCUMENTS

| | | | |
|---|---|---|---|
| 8,907,094 B2 * | 12/2014 | Van Niel | C07D 401/12 546/119 |
| 9,139,584 B2 * | 9/2015 | Van Niel | C07D 401/12 |
| 9,181,242 B2 * | 11/2015 | Alcaraz | C07C 53/06 |
| 9,315,503 B2 * | 4/2016 | Van Niel | C07D 471/04 |
| 2013/0143914 A1 | 6/2013 | Woo et al. | |
| 2013/0150343 A1 | 6/2013 | Van Niel et al. | |

FOREIGN PATENT DOCUMENTS

WO   2011/154738 A1   12/2011
WO   2013/083604 A1   6/2013

OTHER PUBLICATIONS

International Search Report and Written Opinion issued Jul. 23, 2013 in PCT/EP2013/061706 filed Jun. 6, 2013.

* cited by examiner

*Primary Examiner* — Charanjit Aulakh
(74) *Attorney, Agent, or Firm* — Oblon, McClelland, Maier & Neustadt, L.L.P.

(57) ABSTRACT

Mitogen activated protein kinase (MAPK) inhibitors disclosed herein are useful for the treatment of diseases of the respiratory tract, such as chronic eosinophilic pneumonia, asthma, COPD, adult respiratory distress syndrome (ARDS), exacerbation of airways hyper-reactivity consequent to other drug therapy, and airways disease that is associated with pulmonary hypertension.

20 Claims, No Drawings

DERIVATIVES OF [1, 2, 4] TRIAZOLO [4, 3-A] PYRIDINE AS P38—MAP KINASE INHIBITORS

CROSS REFERENCES TO RELATED APPLICATIONS

This application is a 371 of International Patent Application No. PCT/EP2013/061706, filed on Jun. 6, 2013, which is incorporated herein by reference in its entirety.

This invention relates to compounds and compositions that are p38 MAPK inhibitors, useful as anti-inflammatory agents in the treatment of, inter alia, diseases of the respiratory tract.

BACKGROUND TO THE INVENTION

Mitogen activated protein kinases (MAPK) constitute a family of proline-directed serine/threonine kinases that activate their substrates by dual phosphorylation. There are four known human isoforms of p38 MAP kinase, p38α, p38β, p38γ and p38δ. The p38 kinases, which are also known as cytokine suppressive anti-inflammatory drug binding proteins (CSBP), stress activated protein kinases (SAPK) and RK, are responsible for phosphorylating (Stein et al., Ann. Rep. Med Chem., 1996, 31, 289-298) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447). The products of p38 phosphorylation have been shown to mediate the production of inflammatory cytokines, including tumor necrosis factor alpha (TNFα) and interleukin-(IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm. Exp. Thera., 1996, 279, 1453-1461; Griswold et al, Pharmacol. Comm., 1996, 7, 323-229). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1β, IL-6, IL-4, IL-5 and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425). It is believed that the compounds of the present invention can be used to treat p38 mediated diseases such as: asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467). P38 kinase inhibitors containing a triazolopyridine motif are known in the art, for example WO07/091152, WO04/072072, WO06/018727.

Other p38 MAP Kinase inhibitors are described in the co-pending applications PCT/EP2011/072375, PCT/EP2012/074446 and PCT/EP2012/074450.

BRIEF DESCRIPTION OF THE INVENTION

The compounds of the present invention are inhibitors of p38 mitogen activated protein kinase ("p38 MAPK", "p38 kinase" or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

SUMMARY OF THE INVENTION

Our copending international patent applications No. PCT/EP2012/074446 and PCT/EP2012/074450 are concerned, inter alia, with compounds of formula (I), described in those applications, that are p38 MAPK inhibitors, useful as anti-inflammatory agents in the treatment of, inter alia, diseases of the respiratory tract.

The present invention relates to compounds which are p38 MAPK inhibitors falling within the scope of Formula (I) of No. PCT/EP2012/074446 and Formula (I) of PCT/EP2012/074450, but not specifically disclosed therein.

DESCRIPTION OF THE INVENTION

According to the present invention, there is provided a compound selected from the group consisting of:

1-[3-tert-Butyl-1'-(2-[1,4]oxazepan-4-yl-ethyl)-1'H[1,4']bipyrazolyl-5-yl]-3-{(4-[3-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(4-methyl-piperazin-1-yl)-ethyl]-1'H-[1,4']bipyrazolyl-5-yl}-3-{(4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(4-hydroxy-piperidin-1-yl)-ethyl]-1'H-[1,4']bipyrazolyl-5-yl}-3-{4-[3-2-methyl-piperidin-1-yl)-[1,2,4]triazolo[4,3-a]pyridin-6-yloxy]-1,2,3,4-tetrahydro-naphthalen-1-yl}-urea formate salt;

1-(3-tert-Butyl-1'-{2-[(2-methoxy-ethyl)-methyl-amino]-ethyl}-1'H-[1,4']bipyrazolyl-5-yl)-3-4-[3-(–2-methyl-piperidin-1-yl)-[1,2,4]triazolo[4,3-a]pyridin-6-yloxy]-1,2,3,4-tetrahydro-naphthalen-1-yl}-urea;

1-[3-tert-Butyl-1'-(2-piperidin-1-yl-ethyl)-1'H-[1,4']bipyrazolyl-5-yl]-3-{4-[3-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-[1,4]oxazepan-4-yl-ethyl)-1'H-[1,4']bipyrazolyl-5-yl]-3-{4-[3-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-[4-(3-dimethylamino-[1,2,4]triazolo[4,3-a]pyridin-6-yloxy)-1,2,3,4-tetrahydro-naphthalen-1-yl]-urea formate salt;

1-[3-tert-Butyl-1'-(2-dimethylamino-ethyl)-1'H[1,4']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(3-dimethylamino-propyl)-1'H-[1,4']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[3-(4-methyl-piperazin-1-yl)-propyl]-1'H-[1,4']bipyrazolyl-5-yl}-3-{4-[3-2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,3']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,3']bipyrazolyl-5-yl]-3-{4-[3-(2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(2-dimethylamino-ethyl)-2H-pyrazol-3-yl]-3-{4-[3-(2,6-dimethyl-piperidin-1-yl)-[1,2,4]triazolo[4,3-a]pyridin-6-yloxy]-1,2,3,4-tetrahydronaphthalen-1-yl}-urea formate salt;

1-{5-tert-Butyl-2-[5-(2-dimethylamino-ethoxy)-pyridin-3-yl]-2H-pyrazol-3-yl}-3-{4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[5-(2-dimethylamino-ethoxy)-pyridin-3-yl]-2H-pyrazol-3-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[6-(2-dimethylamino-ethoxy)-pyridin-2-yl]-2H-pyrazol-3-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{-4-[3-(2,6-dichloro-phenyl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3 [4-(3-isopropyl-[1,2,4]triazolo[4,3-a]pyridin-6-yloxy)-1,2,3,4-tetrahydro-naphthalen-1-yl]-urea formate salt;

1-[3-tert-Butyl-1'-(2-pyrrolidin-1-yl-ethyl)-1'H-[1,4']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(4-methoxy-piperidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-(3-tert-Butyl-1'-{2-[(2-hydroxy-ethyl)-methyl-amino]-ethyl}-1'H-[1,4']bipyrazolyl-5-yl)-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-((S)-3-hydroxy-pyrrolidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(3-methoxy-pyrrolidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt 1-{3-tert-Butyl-1'-[2-(ethyl-methyl-amino)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt 1-{3-tert-Butyl-1'-[2-((S)-2-hydroxymethyl-pyrrolidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt 1-{3-tert-Butyl-1'-[2-(5-methyl-2,5-diaza-bicyclo[2.2.1]hept-2-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt 1-[3-tert-Butyl-1'-(2-dimethylamino-ethyl)-1'H-[1,4']bipyrazolyl-5-yl]-3-{4-[3-(2-hydroxymethyl-pyrrolidin-1-yl)-[1,2,4]triazolo[4,3-a]pyridin-6-yloxy]-1,2,3,4-tetrahydro-naphthalen-1-yl}-urea 1-[3-tert-Butyl-1'-(2-hydroxy-ethyl)-1'H-[1,4']bipyrazolyl-5-yl]-3-{4-[3-(1-methyl-pyrrolidin-2-yl)-[1,2,4]triazolo[4,3-a]pyridin-6-yloxy]-1,2,3,4-tetrahydro-naphthalen-1-yl}-urea formate salt 1-[3-tert-Butyl-1'-(2-dimethylamino-ethyl)-1'H-[1,4']bipyrazolyl-5-yl]-3-{4-[3-(1-methyl-pyrrolidin-2-yl)-[1,2,4]triazolo[4,3-a]pyridin-6-yloxy]-1,2,3,4-tetrahydro-naphthalen-1-yl}-urea formate salt 1-{5-tert-Butyl-2-[6-(2-dimethylamino-ethoxy)-pyridazin-4-yl]-2H-pyrazol-3-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt and pharmaceutically acceptable salts thereof.

In particular, the present invention provides a compound selected from the group consisting of those of listed in the Table herebelow, or a pharmaceutically acceptable salt thereof:

| Compound Name | Ex. N. |
|---|---|
| 1-[3-tert-Butyl-1'-(2-[1,4]oxazepan-4-yl-ethyl)-1'H[1,4']-bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 1 |
| 1-{3-tert-Butyl-1'-[2-(4-methyl-piperazin-1-yl)-ethyl]-1'H-[1,4']-bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 2 |
| 1-{3-tert-Butyl-1'-[2-(4-hydroxy-piperidin-1-yl)-ethyl]-1'H-[1,4']-bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 3 |
| 1-(3-tert-Butyl-1'-{2-[(2-methoxy-ethyl)-methyl-amino]-ethyl}-1'H-[1,4']-bipyrazolyl-5-yl)-3-{(1S,4R)-4-[3-((S)-2-methyl-piperidin-1-yl)-[1,2,4]-triazolo[4,3-a]pyridin-6-yloxy]-1,2,3,4-tetrahydro-naphthalen-1-yl}-urea | 4 |
| 1-[3-tert-Butyl-1'-(2-piperidin-1-yl-ethyl)-1'H-[1,4']-bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | 5 |
| 1-[3-tert-Butyl-1'-(2-[1,4]oxazepan-4-yl-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | 6 |
| 1-[3-tert-Butyl-1'-(2-dimethylamino-ethyl)-1'H-[1,4']bipyrazolyl-5-yl]-3-[(1S,4R)-4-(3-dimethylamino-[1,2,4]triazolo[4,3-a]pyridin-6-yloxy)-1,2,3,4-tetrahydro-naphthalen-1-yl]-urea formate salt | 7 |
| 1-[3-tert-Butyl-1'-(2-dimethylamino-ethyl)-1'H[1,4']bipyrazolyl-5-yl]-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea formate salt | 8 |
| 1-[3-tert-Butyl-1'-(3-dimethylamino-propyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 9 |
| 1-{3-tert-Butyl-1'-[3-(4-methyl-piperazin-1-yl)-propyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 10 |
| 1-[3-tert-Butyl-1'-(2-dimethylamino-ethyl)-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 11 |
| 1-[3-tert-Butyl-1'-(2-dimethylamino-ethyl)-1'H-[1,3']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | 12 |
| 1-[5-tert-Butyl-2-(2-dimethylamino-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydronaphthalen-1-yl}-urea formate salt | 13 |
| 1-{5-tert-Butyl-2-[5-(2-dimethylamino-ethoxy)-pyridin-3-yl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | 14 |
| 1-{5-tert-Butyl-2-[5-(2-dimethylamino-ethoxy)-pyridin-3-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 15 |
| 1-{5-tert-Butyl-2-[6-(2-dimethylamino-ethoxy)-pyridin-2-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 16 |
| 1-[3-tert-Butyl-1'-(2-dimethylamino-ethyl)-1'H-[1,4']bipyrazolyl-5-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea formate salt | 17 |
| 1-[3-tert-Butyl-1'-(2-dimethylamino-ethyl)-1'H-[1,4']bipyrazolyl-5-yl]-3[(1S,4R)-4-(3-isopropyl-[1,2,4]triazolo[4,3-a]pyridin-6-yloxy)-1,2,3,4-tetrahydro-naphthalen-1-yl]-urea | 18 |
| 1-[3-tert-Butyl-1'-(2-pyrrolidin-1-yl-ethyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 19 |
| 1-{3-tert-Butyl-1'-[2-(4-methoxy-piperidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 20 |
| 1-(3-tert-Butyl-1'-{2-[(2-hydroxy-ethyl)-methyl-amino]-ethyl}-1'H-[1,4']bipyrazolyl-5-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 21 |
| 1-{3-tert-Butyl-1'-[2-((S)-3-hydroxy-pyrrolidin-1-yl)-ethyl]-1'H-[1,4']-bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 22 |
| 1-{3-tert-Butyl-1'-[2-(3-methoxy-pyrrolidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 23 |
| 1-{3-tert-Butyl-1'-[2-(ethyl-methyl-amino)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 24 |
| 1-{3-tert-Butyl-1'-[2-((S)-2-hydroxymethyl-pyrrolidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 25 |
| 1-{3-tert-Butyl-1'-[2-((1S,4S)-5-methyl-2,5-diaza-bicyclo[2.2.1]hept-2-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 26 |
| 1-[3-tert-Butyl-1'-(2-dimethylamino-ethyl)-1'H-[1,4']bipyrazolyl-5-yl]-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea | 27 |
| 1-[3-tert-Butyl-1'-(2-hydroxy-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt | 28 |
| 1-[3-tert-Butyl-1'-(2-dimethylamino-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt | 29 |

| Compound Name | Ex. N. |
|---|---|
| 1-{5-tert-Butyl-2-[6-(2-dimethylamino-ethoxy)-pyridazin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | 30 |

In another aspect, the invention includes pharmaceutical compositions comprising a compound of the invention, together with one or more pharmaceutically acceptable carriers and/or excipients. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, bronchiectasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Compounds of the invention may exist in one or more geometrical, optical, enantiomeric, diastereomeric and tautomeric forms, including but not limited to cis- and trans-forms, R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

As used herein the term "salt" includes base addition, acid addition and ammonium salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds of the invention which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal habits.

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, $3^{rd}$ Edition, 2002, Taylor and Francis).

Prodrugs in accordance with the invention can, for example, be produced by replacing appropriate functionalities present in the compounds of the invention with certain moieties known to those skilled in the art as 'pro-moieties' as described, for example, in *Design of Prodrugs* by H. Bundgaard (Elsevier, 1985).

EMBODIMENTS OF THE INVENTION

In one embodiment, the compounds of invention are compounds of formula (Ia) or pharmaceutically acceptable salts thereof:

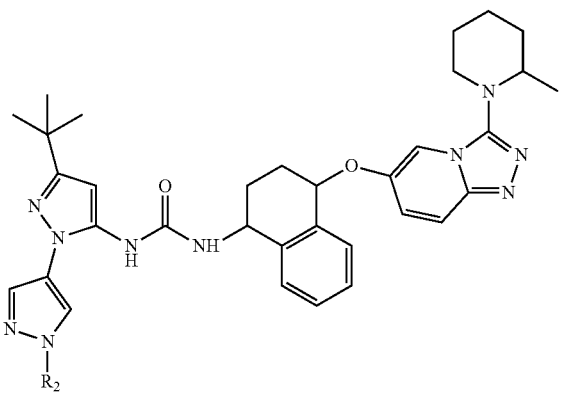

(Ia)

wherein the group $R_2$ is selected in the group consisting of:

1'-(2-[1,4]oxazepan-4-yl-ethyl);
2-[1,4]oxazepan-4-yl-ethyl;
2-(4-hydroxy-piperidin-1-yl)-ethyl;

{2-[(2-methoxy-ethyl)-methyl-amino]-ethyl};
1'-(2-dimethylamino-ethyl);
1'-(3-dimethylamino-propyl);
1'-[3-(4-methyl-piperazin-1-yl)-propyl];
1'-(2-dimethylamino-ethyl);
1'-(2-pyrrolidin-1-yl-ethyl);
1'-[2-(4-methoxy-piperidin-1-yl)-ethyl];
1'-{2-[(2-hydroxy-ethyl)-methyl-amino]-ethyl};
1'-[2-((S)-3-hydroxy-pyrrolidin-1-yl)-ethyl];
1'-[2-(3-methoxy-pyrrolidin-1-yl)-ethyl];
1'-[2-(ethyl-methyl-amino)-ethyl];
1'-[2-((S)-2-hydroxymethyl-pyrrolidin-1-yl)-ethyl];
1'-[2-((1S,4S)-5-methyl-2,5-diaza-bicyclo[2.2.1]hept-2-yl)-ethyl];
2-[6-(2-dimethylamino-ethoxy)-pyridazin-4-yl].

In another embodiment, the compounds of invention are compounds of formula (Ib) or pharmaceutically acceptable salts thereof:

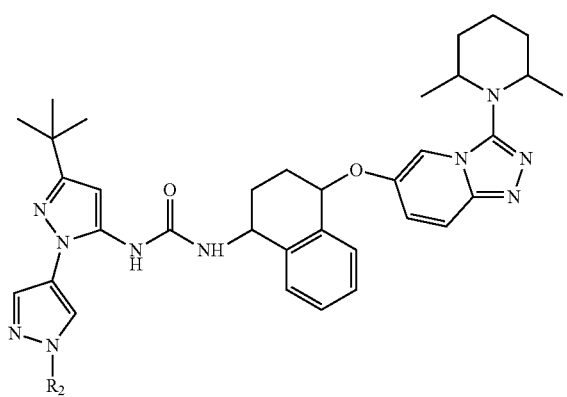

(Ib)

wherein the group $R_2$ is selected in the group consisting of:
1'-(2-piperidin-1-yl-ethyl);
1'-(2-[1,4]oxazepan-4-yl-ethyl);
1'-(2-dimethylamino-ethyl).

In another embodiment, the compounds of invention are compounds of formula (Ic) or pharmaceutically acceptable salts thereof:

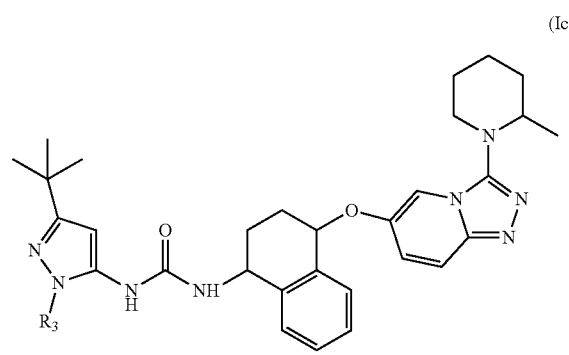

(Ic)

wherein the group $R_3$ is selected in the group consisting of:
2-[5-(2-dimethylamino-ethoxy)-pyridin-3-yl];
2-[6-(2-dimethylamino-ethoxy)-pyridin-2-yl];
2-[6-(2-dimethylamino-ethoxy)-pyridazin-4-yl].

In another embodiment, the compounds of invention are compounds of formula (Id) or pharmaceutically acceptable salts thereof:

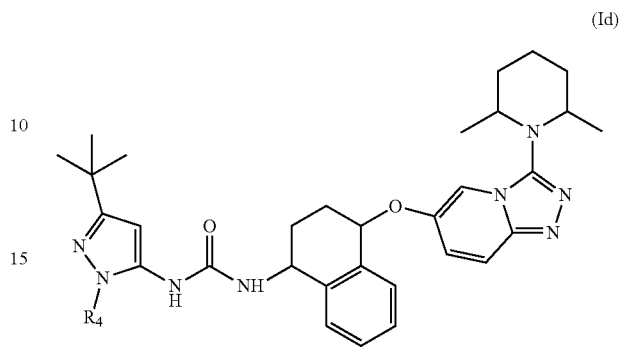

(Id)

wherein the group $R_4$ is selected in the group consisting of:
2-(2-dimethylamino-ethyl);
2-[5-(2-dimethylamino-ethoxy)-pyridin-3-yl].

Utility

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

Compositions

As mentioned above, the compounds of the invention are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 μg to about 1 mg per kg body weight of a human, preferably 0.1 μg to 50 μg per kg, in single or divided doses. On the other hand, it may be necessary to use dosages outside these limits in some cases. For the purpose of the invention, inhaled administration is preferred.

The compounds of the invention may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI).

Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Combinations

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199, Vilanterol, olodaterol, Abediterol; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028; (5) dual pharmacology M3-anticholinergic/β2-adrenoreceptor agonists such as GSK961081; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412; (20) A2b antagonists such as those described in WO2002/42298; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and AZD1981 and mixed DP1/CRTH2 antagonists such as AMG 009; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; (28) MCP-1 antagonists such as ABN-912.

The invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

General Experimental Details

Abbreviations used in the experimental section: AcOH=acetic acid; aq.=aqueous; DCM=dichloromethane; DIAD=Diisopropyl azodicarboxylate; DIPEA=diisopropylethylamine; DMAP=N,N-dimethylaminopyridine; DMF=N,N-dimethylformamide; $d_6$-DMSO=deuterated dimethyl sulfoxide; EDC=1-ethyl-3-(3'-dimethylaminopropyl)carbodiimide Hydrochloride; EtOAc=ethyl acetate; EtOH=ethanol; $Et_2O$=diethyl ether; $Et_3N$=triethylamine; $EtNiPr_2$=diisopropylethylamine; FCC=flash column chromatography; h=hour; HATU=2-(7-aza-1H-benzotriazole-1-yl)-1,1,3,3-tetramethyluronium hexafluorophosphate; HOBt=1-hydroxy-benzotriazole; HPLC=high performance liquid chromatography; IMS=Industrial Methylated Spirits; LCMS=liquid chromatography mass spectrometry; NaOH=sodium hydroxide; MeCN=acetonitrile; MeOH=Methanol; min=minutes; $NH_3$=ammonia; NMR=nuclear magnetic resonance; RT=room temperature; Rt=retention time; sat.=saturated; SCX-2=strong cation exchange chromatography; TFA=trifluoroacetic acid; THF=Tetrahydrofuran; $H_2O$=water; Xantphos=4,5-Bis(diphenylphosphino)-9,9-dimethylxanthene; X-Select=Waters X-select HPLC column; IPA=propan-2-ol; LDA=lithium diisopropylamide; MDAP=mass-directed auto-purification; $Ph_3P$=triphenylphosphine; TBAF=tetrabutylammonium fluoride.

In the procedures that follow, after each starting material, reference to a Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO2008/043019 for key intermediates. All reactions were carried out under anhydrous conditions and an atmosphere of nitrogen or Argon unless specified otherwise. Unless otherwise stated all transformations were carried at ambient temperature (room temperature).

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane (δ=0 ppm). J values are given in Hz through-out. NMR spectra were assigned using DataChord Spectrum Analyst Version 4.0.b21 or SpinWorks version 3.

Where products were purified by flash column chromatography (FCC), 'flash silica' refers to silica gel for chromatography, 0.035 to 0.070 mm (220 to 440 mesh) (e.g. Fluka silica gel 60), and an applied pressure of nitrogen up 20 to 10 p.s.i. accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 μm particle size), or a Phenyl-Hexyl column (250×21.2 mm i.d. Gemini column with 5 μm particle size), UV detection between 220-254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid), or a C18-reverse-phase column (19×250 mm, XBridge OBD, with 5 μm particle size), eluting with gradients from 100-0 to 0-100% water/acetonitrile (containing 0.1% $NH_4OH$); or a ChiralPak IC column (10×250 mm i.d., with 5 μm particle size), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) and HPLC systems used are:

Method 1
Waters Platform LC Quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 2
Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line Waters 996 DAD detector). MS ionization method—Electrospray (positive and negative ion).

Method 3
Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 4
VG Platform II quadrupole spectrometer with a C18-reverse-phase column (30×4.6 mm Phenomenex Luna 3 μm particle size, elution with A: water+0.1% formic acid; B: acetonitrile+0.1% formic acid. Gradient:

| Gradient-Time | flow mL/min | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 μl/min split to the ESI source with inline HP1050 DAD detector). MS ionization method—Electrospray (positive and negative ion).

Method 5
Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: acetonitrile+0.1% formic acid. Gradient:

| Gradient-Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 6
Phenomenex Gemini C18-reverse-phase column (250×21.20 mm 5 μm particle size), elution with A: water+0.1% formic acid; B: $CH_3CN$+0.1% formic acid. Gradient—90% A/10% B to 2% A/98% B over 20 min—flow rate 18 mL/min. Detection—In-line UV detector set at 254 nM wavelength.

Method 7
Agilent 1260 infinity purification system. Column: XSELECT CSH Prep C18 OBD, particle size 5 m, 30×150 mm, RT. Elution with A: water+0.1% formic acid; B: $CH_3CN$+0.1% formic acid. Gradient—90% A/10% B to 2% A/95% B over 22 min—flow rate 60 mL/min. Detection—In-line Agilent 6100 series single Quadrupole LC/MS.

Method 8

Agilent 1260 infinity purification system. Column: XBridge Prep C18 OBD, particle size 5 μm, 30×150 mm, RT. Elution with A: water+0.1% ammonia; B: CH₃CN+ 0.1% ammonia. Gradient—90% A/10% B to 2% A/95% B over 22 min—flow rate 60 mL/min. Detection—In-line Agilent 6100 series single Quadrupole LC/MS.

Example 1

Intermediate 1

(1R,4S)-4-Amino-1,2,3,4-tetrahydro-naphthalen-1-ol

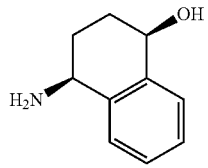 [SMILES: N[C@H]1CC[C@@H](O)c2ccccc21]

a. 2,2,2-Trifluoro-N—(S)-1,2,3,4-tetrahydro-naphthalen-1-yl-acetamide (Intermediate 1a)

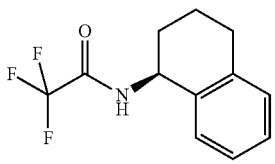 [SMILES: O=C(N[C@H]1CCCc2ccccc21)C(F)(F)F]

To a mechanically stirred solution of (S)-(+)-(1,2,3,4-tetrahydro-naphthalen-1-yl)amine (CAS: 23357-52-0, 175 g, 1.19 mol) and triethylamine (250 mL, 1.79 mol) in MeOH (1.75 L), ethyl trifluoroacetate (170 mL, 1.43 mol) was added dropwise at a rate to maintain the internal temperature below 30° C. (ca. over 20 min). The resulting solution was stirred at RT overnight. The mixture was concentrated in vacuo. This was partitioned between DCM (1 L) and water (1 L). The layers were separated and the aqueous layer was extracted with DCM (2×600 mL). The combined organic layers were washed with brine, dried (Na₂SO₄), filtered and concentrated in vacuo to yield Intermediate 1a (289.4 g, 100%). ¹H NMR (400 MHz, CDCl₃): 1.80-1.95 (3H, m), 2.05-2.15 (1H, m), 2.75-2.90 (2H, m), 5.18-5.25 (1H, q, J=5.0 Hz), 6.38-6.48 (1H, br s), 7.12-7.16 (1H, m), 7.20-7.26 (3H, m).

b. 2,2,2-Trifluoro-N—((S)-4-oxo-1,2,3,4-tetrahydro-naphthalen-1-yl)-acetamide (Intermediate 1b)

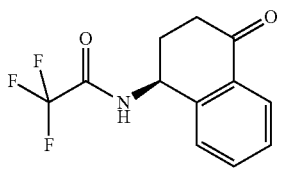 [SMILES: O=C1CC[C@H](NC(=O)C(F)(F)F)c2ccccc21]

A 20 L flask was charged with Intermediate 1a (288 g, 1.19 mol) and acetone (7 L). Magnesium sulfate monohydrate (328 g, 2.37 mol) in water (3 L) was added and the mixture stirred mechanically, and cooled to internal temperature ~1.5° C. Potassium permanganate (562.1 g, 3.56 mol) was then added in 7 equal portions (i.e. 80.3 g) every 15 min for 105 min. Water (0.5 L) was added and the resulting mixture was stirred at RT for 17 h. The mixture was cooled to 15° C. and a solution of sodium thiosulfate pentahydrate (883 g, 3.56 mol) in water (3 L) was added dropwise over 1 h, whilst maintaining internal temperature below 18° C. The resulting slurry was stirred for 1 h and the mixture left to stand at RT overnight. The solid had settled at the bottom of the flask and the solution was decanted and then concentrated to leave a residue. The remaining solid was treated with ethyl acetate (7 L) and water (2 L) and the mixture was filtered through Celite. The filtrate was combined with the residue isolated above. The mixture was separated and the aqueous layer extracted with ethyl acetate (2×1 L). The organics were combined and drying agent (Na₂SO₄) and decolourising charcoal were added. The mixture was filtered through Celite and concentrated to dryness in vacuo to yield Intermediate 1b (260 g, 85%). ¹H NMR (400 MHz, CDCl₃): 2.20-2.30 (1H, dddd, J=13.3, 10.0, 8.8, 4.5 Hz), 2.43-2.52 (1H, dddd, J=13.3, 7.2, 4.6, 4.6 Hz), 2.67-2.77 (1H, ddd, J=17.4, 10.1, 4.6 Hz), 2.78-2.88 (1H, ddd, J=17.4, 7.1, 4.6 Hz), 5.39-5.47 (1H, td, J=8.5, 4.5 Hz), 7.32-7.37 (1H, d, J=7.7 Hz), 7.44-7.49 (1H, t, J=7.6 Hz), 7.59-7.64 (1H, td, J=7.6, 1.4 Hz), 8.03-8.07 (1H, dd, J=7.7, 1.4 Hz).

c. 2,2,2-Trifluoro-N-((1S,4R)-4-hydroxy-1,2,3,4-tetrahydro-naphthalen-1-yl)-acetamide (Intermediate 1c)

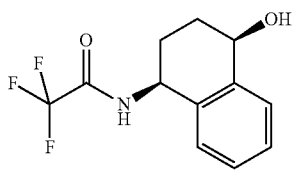 [SMILES: O=C(N[C@H]1CC[C@@H](O)c2ccccc21)C(F)(F)F]

A solution of Intermediate 1b (161 g, 624 mmol) in DMF (2 L) was vacuum degassed with Argon. [N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium (CAS: 192139-92-7, 9.95 g, 15.6 mmol) was then added. Formic acid (57.5 g, 1.25 mol) was added slowly to ice cold triethylamine (126 g, 1.25 mol) with stirring, this was then added to the DMF solution. The resulting reaction mixture was heated to 50° C. (internal temperature) for 41 h with stirring. LCMS analysis of the reaction indicated it was incomplete, therefore a solution of formic acid (14.4 g, 313 mmol) was added slowly to ice cold triethylamine (31.6 g, 312 mmol), this was then added to the reaction mixture. Heating was continued for an additional 22 h. After cooling, the mixture was concentrated in vacuo to give an orange residue. The residue was diluted with ethyl acetate (1.5 L) and the solution washed with brine (2×0.5 L). The organics were dried (Na₂SO₄), filtered and concentrated in vacuo. Purification by column chromatography (Silica, 3 Kg, 0-50% ethyl acetate in cyclohexane) gave Intermediate 1c (118 g, 73%). 97.5 d.e. % determination by LCMS (Method 4) Rt 3.37 min, M-H 258 (93.7%, desired); Rt 3.25 min, M-H 258 (1.2%, trans isomer). ¹H NMR (400 MHz, CDCl₃): 1.88-1.92 (1H, d, J=4.8 Hz), 1.98-2.18 (4H, m), 4.80-4.88 (1H, m), 5.165-5.24 (1H, m), 6.70-6.80 (1H, br s), 7.25-7.30 (1H, m), 7.30-7.40 (2H, m), 7.45-7.50 (1H, m).

d. (1R,4S)-4-Amino-1,2,3,4-tetrahydro-naphthalen-1-ol (Intermediate 1)

To a stirred solution of Intermediate 1c (117 g, 451 mmol) in methanol (0.7 L), 6N aqueous sodium hydroxide solution (190 mL, 1.14 mol) was added and stirred at RT for 20 h. The mixture was concentrated in vacuo and the residue was diluted with ethyl acetate (1 L) and water (0.5 L). Concentrated HCl solution (95 mL, 1.14 mol) was added slowly with stirring. Additional HCl was used to adjust the pH of the aqueous layer to pH=2. The mixture was then separated and the organic layer was extracted with HCl solution (2M aqueous, 3×500 mL). The combined aqueous layers were basified to pH~12, by addition of concentrated aqueous NH$_4$OH solution, and then extracted in to ethyl acetate (5×750 mL). The combined organic extracts were washed with brine (200 mL), dried (Na$_2$SO$_4$), filtered and concentrated in vacuo to give a solid (50.8 g). This material was recrystallized (cyclohexane/ethyl acetate [2:1], 350 mL) to provide Intermediate 1 as a solid (44.4 g, 60%). $^1$H NMR (400 MHz, d$_6$-DMSO): 1.66-1.90 (4H, m), 3.71-3.77 (1H, t, J=5.4 Hz), 4.46-4.54 (1H, t, J=5.4 Hz), 7.14-7.22 (2H, m), 7.32-7.38 (1H, m), 7.40-7.46 (1H, m).

Intermediate 2

(1S,4R)-4-[3-((S)-2-Methyl-piperidin-1-yl)-[1,2,4]triazolo[4,3-a]pyridin-6-yloxy]-1,2,3,4-tetrahydro-naphthalen-1-ylamine

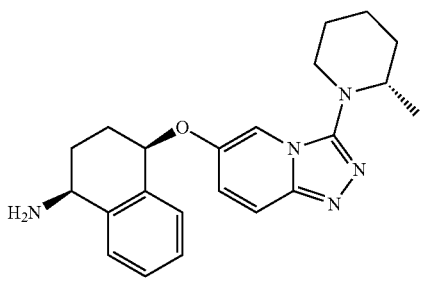 [SMILES: C[C@H]1CCCCN1c1nnc2ccc(O[C@@H]3CC[C@H](N)c4ccccc43)cn12]

a. (R)-Hydroxy-phenyl-acetate(S)-2-methyl-piperidinium (Intermediate 2a)

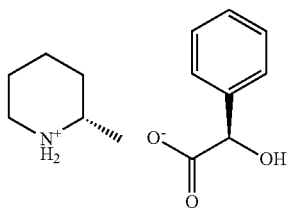

2-Methylpiperidine (99.7 g, 1.0 mol) [CAS 109-05-7] was dissolved in MeOH (100 mL) in a 2 L Florentine flask and cooled in an ice bath. (R)-(−)-mandelic acid (152.9 g, 1.0 mol) [CAS 611-71-2] was then added and the reagents stirred with gentle heating until a homogenous solution resulted. The solution was left to cool, and Et$_2$O (900 mL) was added. The flask walls were scratched to aid crystallisation, and then stored in a fridge for 18 h. The resulting crystals were then filtered off, and washed with cold Et$_2$O. The product was recrystallized again from MeOH (100 mL) and Et$_2$O (500 mL) and left in a fridge for 48 h. The crystals were filtered off, washed with Et$_2$O and dried in a vacuum oven at 50° C. overnight to afford Intermediate 2a (66.97 g, 53%) as colourless crystals. $^1$H NMR (300 MHz, d$_6$-DMSO-d$_6$): 1.12 (3H, d, J=6.5 Hz), 1.20-1.57 (3H, m), 1.58-1.74 (3H, m), 2.72 (1H, dt, J=3.2, 12.4 Hz), 2.88-3.02 (1H, m), 3.06-3.18 (1H, m), 4.51 (1H, s), 7.11-7.19 (1H, m), 7.19-7.29 (2H, m), 7.33-7.42 (2H, m).

Diastereomeric purity was measured using Marfey's method; compound 2 (1 mg, 3.68 µmol) was dissolved in EtOAc (1 mL) and H$_2$O (1 mL) and Marfey's reagent was added (N$_\alpha$-(2,4-Dinitro-5-fluorophenyl)-L-alaninamide, FDAA [CAS 95713-52-3], 1 mg, 3.68 µmol) followed by saturated NaHCO$_3$ solution (50 µL) and heated to 50° C. for 1 hour. The mixture was then diluted with H$_2$O (1 mL) and subjected to analytical HPLC (Waters X-Select C18, 2.5 m, 4.6×50 mm, 32-34% CH$_3$CN/H$_2$O (+0.1% formic acid), 16 min gradient, 1 mL/min, 340 nm). Rt 10.82 min, >99% d.e.

Racemic 2-methylpiperidine was also subjected to Marfey's method; HPLC: Rt 10.75 min (50%), 11.581 min (50%).

b. (S)-2-Methyl-piperidine-1-carbonyl chloride (Intermediate 2b)

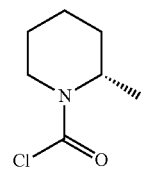

Intermediate 2a (12.0 g, 47.75 mmol) was treated with aqueous NaOH solution (1N; 96 mL, 96 mmol) and extracted into DCM (2×75 mL). This solution of (S)-2-methyl piperidine was transferred to a 3-necked RB flask, stirred under an inert atmosphere and cooled in an ice-bath before pyridine (11.6 mL, 143.72 mmol) was added followed by triphosgene (14.17 g, 47.75 mmol) during 30 min at <10° C. The cooling bath was removed after 30 min and the mixture stirred at RT for a further 3.5 hours. Reaction was quenched by very careful addition of aqueous HCl (1N, 300 mL) at 0-5° C. After 30 min the phases were separated and the aqueous layer extracted with DCM (2×100 mL). Combined DCM extracts were washed with brine, dried (MgSO$_4$), passed through a phase separation cartridge and concentrated in vacuo to give Intermediate 2b (8.6 g, >100% still containing some DCM). $^1$H NMR (300 MHz, CDCl$_3$): 1.25 (3H, d, J 6.8), 1.40-1.80 (6H, m), 3.0 (1H, br), 4.12-4.21 (1H, m), 4.56-4.67 (1H, m).

c. (S)-2-Methyl-piperidine-1-carboxylic acid N'-(5-fluoro-pyridin-2-yl)-hydrazide (Intermediate 2c)

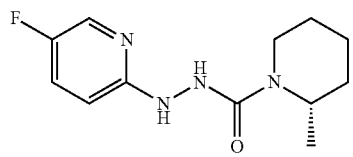 [SMILES: C[C@H]1CCCCN1C(=O)NNc1ccc(F)cn1]

A stirred solution of Intermediate 2b (17.20 g, assumed to be 95.49 mmol) and (5-fluoro-pyridin-2-yl)-hydrazine (12.14 g, 95.51 mmol) in DCM (300 mL) at RT was treated with DIPEA (34 mL, 195.18 mmol) during 5 min. This mixture was continued to be stirred at RT for 4 days before being added to water (500 mL) and phases separated. The aqueous layer was further extracted into DCM (4×100 mL), combined extracts washed with brine, dried (MgSO$_4$), passed through a phase separation cartridge and concentrated in vacuo to give a residual solid. This product was treated with Et$_2$O-pentane and the resultant solids filtered off and dried to give Intermediate 2c (18.74 g, 77%). LCMS (Method 3) Rt 2.26 min, m/z 253 [MH$^+$]. $^1$H NMR (300 MHz, CDCl$_3$): 1.23 (3H, d, J 6.9), 1.40-1.74 (6H, m), 2.97 (1H, td, J 13.1, 3.0), 3.82-3.91 (1H, m), 4.27-4.38 (1H, m), 6.54 (1H, s), 6.78 (1H, ddd, J 9.1, 3.7, 0.6), 7.30 (1H, ddd, J 9.1, 7.8, 2.9), 8.00 (1H, d, J 2.6).

d. 6-Fluoro-3-((S)-2-methyl-piperidin-1-yl)-[1,2,4]triazolo[4,3-a]pyridine (Intermediate 2d)

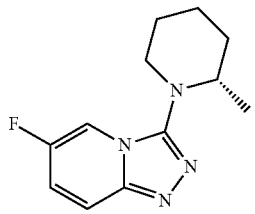 [SMILES: C[C@H]1CCCCN1c1nnc2ccc(F)cn12]

To a stirred solution of Intermediate 2c (14.70 g, 58.27 mmol), Ph$_3$P (30.56 g, 116.51 mmol) and Et$_3$N (33 mL, 236.76 mmol) in THF (300 mL) at RT was added hexachloroethane (27.60 g, 116.58 mmol) during 10 min before then heating at 60° C. overnight. The cooled mixture was filtered and concentrated in vacuo to give a residual oil which was dissolved in DCM (200 mL) and extracted into dilute HCl (2M) until most product had been removed from the DCM phase by LCMS. These aqueous extracts were treated with solid NaOH (with cooling) to achieve ~pH 9 and extracted into DCM. Combined DCM extracts were washed with brine, dried (MgSO$_4$), passed through a phase separation cartridge and concentrated in vacuo to give Intermediate 2d (11.30 g, 82%) as a brown oil. LCMS (Method 3) Rt 2.99 min, m/z 235 [MH$^+$]. $^1$H NMR (300 MHz, d$_6$-d$_6$-DMSO): 0.89 (3H, d, J 6.3), 1.40-1.88 (6H, m), 2.85-2.96 (1H, m), 3.18 (1H, dt, J 12.0, 4.5), 3.28-3.35 (1H, m), 7.42 (1H, ddd, J 10.0, 8.0, 2.3), 7.76 (1H, ddd, J 10.0, 4.9, 0.9), 8.31-8.35 (1H, m).

e. (1S,4R)-4-[3-((S)-2-Methyl-piperidin-1-yl)-[1,2,4]triazolo[4,3-a]pyridin-6-yloxy]-1,2,3,4-tetrahydronaphthalen-1-ylamine (Intermediate 2)

Sodium hydride (60% dispersion in oil, 12 g, 300 mmol) was suspended in DMF (800 mL) and cooled to 0° C. using an ice bath. (24.45 g, 150 mmol) was then added in small portions under N$_2$ and the resulting opaque brown suspension was stirred at RT for 45 min (CARE: gas evolution). A solution of Intermediate 2d (35.1 g, 150 mmol) in dry DMF (200 mL) was added and the dark brown solution stirred at RT for 18 h. The solution was concentrated in vacuo, the residue was poured into a mixture of brine/1N aqueous NaOH/H$_2$O (1:1:1; 200 mL); the product was extracted using mixture of EtOAc and Me-THF (300 mL×5). The organic extracts were combined, washed with a small amount of brine, dried over MgSO$_4$ and concentrated under reduced pressure. The product was purified by FCC, eluting with 0-20% [2M NH$_3$ in MeOH] in DCM, to provide the title compound (27.1 g, 48%). LCMS (Method 3): Rt 2.29 min, m/z 378 [MH$^+$].

Intermediate 3

(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-ylamine

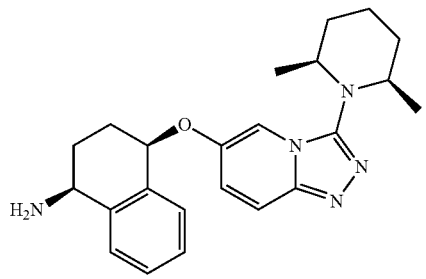 [SMILES: C[C@@H]1CCC[C@H](C)N1c1nnc2ccc(O[C@@H]3CC[C@H](N)c4ccccc43)cn12]

a. (2S,6R)-2,6-Dimethyl-piperidine-1-carbonyl chloride (Intermediate 3a)

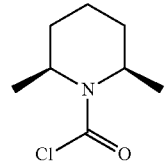

To a solution of triphosgene (20.8 g, 70.0 mmol) in DCM (400 mL) at 5° C. was added pyridine (16.2 mL, 200 mmol) dropwise over 10 min, maintaining the temperature below 10° C. The solution was then stirred between 5-10° C. for 1 h, then cis-2,6-dimethyl piperidine (CAS: 766-17-6, 27.0 mL, 200 mmol) was added dropwise over 10 min and the resulting red solution stirred at RT for 4 days (reaction complete within <4 h). The solution was cooled to 3° C., then a pre-cooled (3° C.) 1M aqueous HCl solution (400 mL) was added and the mixture stirred at 5° C. for 30 min. The mixture was separated and the aqueous layer was extracted with DCM (200 mL), then the combined organic extracts passed through a hydrophobic frit and concentrated under vacuum affording Intermediate 3a as a red oil (31.5 g, 90%). $^1$H NMR (300 MHz, CDCl$_3$): 1.30 (6H, d, J=7.09 Hz), 1.49-1.87 (6H, m), 4.46-4.56 (2H, m).

b. (2S,6R)-2,6-Dimethyl-piperidine-1-carboxylic acid N'-(5-fluoro-pyridin-2-yl)-hydrazide (Intermediate 3b)

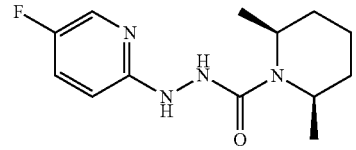 [SMILES: C[C@@H]1CCC[C@H](C)N1C(=O)NNc1ccc(F)cn1]

A dark red solution of (5-fluoro-pyridine-2-yl)-hydrazine (21.7 g, 171 mmol), Intermediate 3a (31.5 g, 180 mmol) and DIPEA (44.7 mmol, 256 mmol) in DCM (350 mL) was stirred at RT for 4 days. Water (350 mL) was added, then the aqueous layer extracted with DCM (100 mL). The combined organic extracts were passed through a hydrophobic frit and concentrated under vacuum to leave a solid. Trituration with diethyl ether/pentane (1:4, 150 mL), and drying under vacuum at 50° C., gave Intermediate 3b (31.7 g, 70%, ~90% purity). LCMS: Rt 2.58 min, m/z 289 [MH+]. ¹H NMR (300 MHz, CDCl₃): 1.29 (6H, d, J=7.0 Hz), 1.45-1.89 (6H, m), 4.26 (2H, apparent quin, J=6.5 Hz), 6.53 (1H, s), 6.65 (1H, br s), 6.77 (1H, dd, J=9.0, 3.6 Hz), 7.29-7.28 (1H, ddd, J=9.0, 8.0, 3.0), 8.02 (1H, d, J=2.9 Hz).

c. 3-((2S,6R)-2,6-Dimethyl-piperidine-1-yl)-6-fluoro-[1,2,4]triazolo[4,3-a]pyridine (Intermediate 3c)

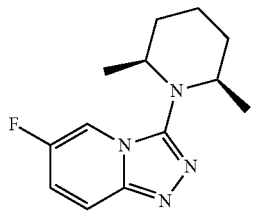 [SMILES: C[C@@H]1CCC[C@H](C)N1c1nnc2ccc(F)cn12]

To a dark red suspension of Intermediate 3b (27.4 g, 102.9 mmol) and pyridine (25 mL, 309.1 mmol) in toluene (250 mL) at 50° C. was added POCl₃ (11.0 mL, 118 mmol) in 3 portions at 30 s intervals. (CARE: exotherm to 70° C.) The brown suspension was stirred at 50° C. for 1 h, then cooled to RT. Water (100 mL) and sat. aqueous NaHCO₃ solution (100 mL) were added (CARE: gas evolution) and the mixture stirred at RT for 30 min. The aqueous was extracted with EtOAc (2×250 mL), then the combined organics washed with brine (250 mL), dried (Na₂SO₄), filtered and concentrated in vacuo to leave a brown oil (26.3 g, overweight). The oil was redissolved in MeOH (150 mL) then charcoal (6 g) was added and the mixture swirled for 30 min. The suspension was filtered through Celite and the filtercake washed with MeOH (25 mL). The filtrate was concentrated in vacuo to leave a red oil. This was azeotroped with pentane (25 mL) to give a solid (24.0 g). The solid was slurried in diethyl ether/pentane (1:1, 40 mL), filtered and dried in vacuo to leave Intermediate 3c (20.6 g, 81%). The mother liquor was concentrated in vacuo, the residue dissolved in hot cyclohexane (50° C., 30 mL), then cooled to RT and allowed to stand for over the weekend. The mixture was filtered, the solid washed with cyclohexane (5 mL) then dried in vacuo at 45° C. to leave additional Intermediate 3c as a solid (1.8 g, 6%). LCMS: Rt 3.30 min, m/z 249 [MH+]. ¹H NMR (300 MHz, CDCl₃): 0.68 (6H, d, J=6.2 Hz), 1.36-1.49 (2H, m), 1.52-1.68 (1H, m), 1.75-1.90 (3H, m), 3.29-3.40 (2H, m), 7.16 (1H, ddd, J=10.0, 7.6, 2.3 Hz), 7.67 (1H, dd, J=10.0, 4.7 Hz), 8.03 (1H, t, J=2.7 Hz).

d. (1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-ylamine (Intermediate 3)

To a solution of Intermediate 1 (6.59 g, 40.4 mmol) in dry DMF (80 mL) under N₂ was added sodium hydride (60% dispersion in oil, 3.20 g, 80.0 mmol) and the resulting opaque brown solution was stirred at RT for 45 min (CARE: gas evolution). A solution of Intermediate 3c (9.93 g, 40.0 mmol) in dry DMF (20 mL) was added and the dark brown solution stirred at RT for 24 h. The reaction was carefully quenched with saturated NH₄Cl (CARE: gas evolution) solution and H₂O. The brown mixture was stirred for 30 min. The mixture was concentration in vacuo gave a dark brown gum, which was dissolved in MeOH (125 mL), charcoal was added to the solution and the mixture was stirred at RT for 1 h, and then filtered through Celite. The solution was evaporated under reduced pressure to afford a dark brown residue. The residue was suspended in H₂O (100 mL) and extracted with EtOAc (3×100 mL). The combined organic extracts were washed with brine (75 mL), dried over Na₂SO₄, filtered and concentrated in vacuo to obtain a foam (14.6 g, 93%). The foam was triturated with pentane (2×75 mL) using sonication and stirring, the solution was decanted and the solid was left to dry under vacuum and at RT affording a solid (14.2 g, 90%). LCMS (Method 3): Rt 2.32 min, m/z 392 [MH+].

Intermediate 4

[6-((1R,4S)-4-Amino-1,2,3,4-tetrahydro-naphthalen-1yloxy)[1,2,4]triazolo[4,3-a]pyridin-3-yl]-dimethyl-amine

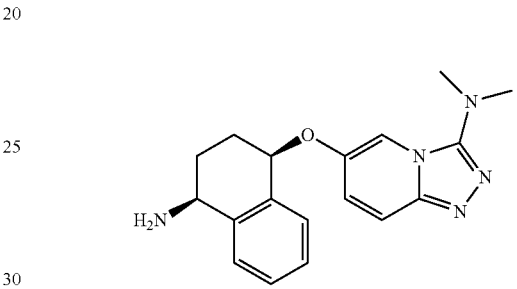

a. 2-(5-Fluoropyridin-2-yl)-N,N-dimethylhydrazine carboxamide (Intermediate 4a)

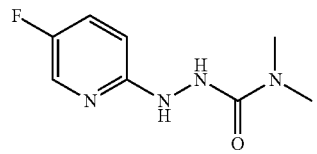

A solution of (5-fluoro-pyridin-2-yl)-hydrazine (500 mg, 3.93 mmol), dimethylcarbamyl chloride (505 mg, 4.72 mmol) and DIPEA (1.01 g, 7.86 mmol) in DCM (20 mL) was stirred at reflux for 16 h. The reaction mixture was applied to an SCX-2 cartridge (25 g), washed with MeOH and the product eluted with 2M NH₃ in MeOH. The product containing fractions were concentrated in vacuo and then triturated with diethyl ether gave the title compound (600 mg, 77%). ¹H NMR (400 MHz, CDCl₃): 2.99 (6H, s), 6.46 (2H, m), 6.75 (1H, dd, J=9.1, 3.5 Hz), 7.22-7.32 (1H, m), 8.03 (1H, d, J=2.7 Hz).

b. (6-Fluoro-[1,2,4]triazolo[4,3-a]pyridin-3-yl)-dimethyl-amine (Intermediate 4b)

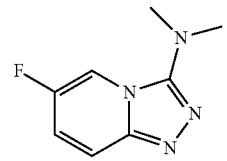

To a solution of Intermediate 4a (590 mg, 2.98 mmol), Ph₃P (1.56 g, 5.96 mmol) and Et₃N (1.20 g, 11.9 mmol) in THF (40 mL) was added hexachloroethane (1.41 g, 5.96 mmol) and the mixture stirred at 60° C. for 9 h. The mixture was diluted with EtOAc (100 mL), washed with water, brine, dried (MgSO₄) and then concentrated in vacuo. The residue was purified by FCC, using 0-10% [2M NH₃ in MeOH] in DCM, then triturated with diethyl ether to give the title compound (78 mg, 14%). LCMS (Method 1): Rt 2.24 min, m/z 181 [MH⁺].

c. [6-((1R,4S)-4-Amino-1,2,3,4-tetrahydro-naphthalen-1-yloxy) [1,2,4]triazolo[4,3-a]pyridin-3-yl]-dimethyl-amine (Intermediate 4)

To a solution of Intermediate 1 (75.0 mg, 0.458 mmol) in DMF (2 mL) was added sodium hydride (60% in oil, 50.0 mg, 1.25 mmol) and the mixture stirred at RT for 20 min, before Intermediate 4b (75.0 mg, 0.416 mmol) was added. This mixture was stirred at 60° C. for 1 h. The cooled reaction mixture was then applied to an SCX-2 cartridge (10 g), washed with MeOH and the product eluted with 2M NH₃ in MeOH. The resulting residue was purified by FCC, using 0-10% [2M NH₃ in MeOH] in DCM, affording the title compound (82.0 mg, 61%). LCMS (Method 4): Rt 1.49 min, m/z 324 [MH⁺].

Intermediate 5 a. (1S,4R)-4-[3-((R)-2-Methyl-piperidin-1-yl)-[1,2,4]triazolo[4,3-a]pyridin-6-yloxy]-1,2,3,4-tetrahydro-naphthalen-1-ylamine

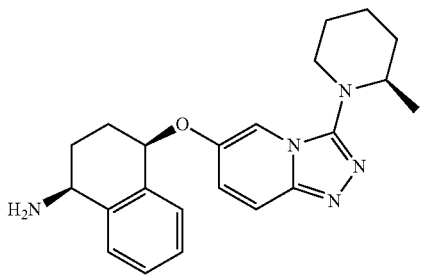 [SMILES: C[C@@H]1CCCCN1c1nnc2ccc(O[C@@H]3CC[C@H](N)c4ccccc43)cn12]

The title compound was prepared starting from (R)-2-methyl piperidine (ABCR) using analogous procedures to those described in the preparation of Intermediate 2. LCMS (Method 3): Rt 2.26 min, m/z 378 [MH⁺]. ¹H NMR (400 MHz, d₆-DMSO): 0.92 (3H, d, J=6.1 Hz), 1.39-2.15 (11H, m), 2.29-2.42 (1H, m), 3.05-3.22 (2H, m), 3.32-3.45 (1H, m), 3.97-4.05 (1H, m), 5.24 (1H, t, J=4.6 Hz), 7.06 (1H, dd, J=9.9, 2.1 Hz), 7.23-7.42 (3H, m, obscured by solvent), 7.50 (1H, d, J=1.9 Hz), 7.55-7.64 (2H, m).

Intermediate 6

[3-tert-Butyl-1'-(2-hydroxy-ethyl)-1'H-[1,4']bipyrazolyl-5-yl]-carbamic acid 2,2,2-trichloro-ethyl ester

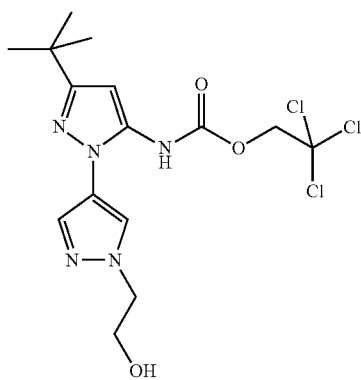 [SMILES: CC(C)(C)c1cc(NC(=O)OCC(Cl)(Cl)Cl)n(-c2cnn(CCO)c2)n1]

a. 2-(4-Iodo-pyrazol-1-yl)-ethanol (Intermediate 6a)

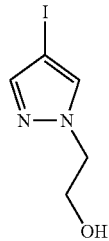

A solution of 4-iodopyrazole (14.3 g, 73.9 mmol) and ethylene carbonate (6.83 g, 77.6 mmol) in DMF (50 mL) was stirred at 125° C. for 24 h. The cooled solution was concentrated under vacuum to leave a brown oil. The residue was purified by FCC, using 30-70% EtOAc in DCM, to give the title compound (9.36 g, 53%). LCMS (Method 3): Rt 2.24 min, m/z 239 [MH⁺].

b. 2-(5-Amino-3-tert-butyl-[1,4']bipyrazolyl-1'-yl)-ethanol (Intermediate 6b)

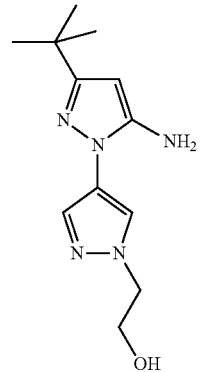 [SMILES: CC(C)(C)c1cc(N)n(-c2cnn(CCO)c2)n1]

A solution of Intermediate 6a (9.36 g, 39.3 mmol) in xylene (40 mL) was purged with Argon for 30 min. In a separate flask, a mixture of 3-tert-butyl-1H-pyrazole-5-amine (5.75 g, 41.3 mmol), copper iodide (375 mg, 1.97 mmol), trans-N,N-dimethylcyclohexane-1,2-diamine (1.12 g, 7.87 mmol) and potassium carbonate (11.4 g, 82.6 mmol) was de-gassed and purged with Argon three times. The xylene solution was then added, via cannula to the flask and the resultant brown solution was heated at reflux for 3 h. The cooled solution was diluted with EtOAc (40 mL) and washed with saturated aqueous ammonia solution/water (1:1, 40 mL). The aqueous layer was extracted with EtOAc (40 mL) and the combined organics were washed with water (40 mL) and brine (40 mL), dried (Na₂SO₄), filtered and concentrated in vacuo to afford a solid. This was purified by FCC, using 4-7.5% MeOH in DCM, to afford the title compound (6.01 g, 61%). LCMS (Method 3): Rt 1.84 min, m/z 250 [MH⁺].

c. [3-tert-Butyl-1'-(2-hydroxy-ethyl)-1'H-[1,4']bipyrazolyl-5-yl]-carbamic acid 2,2,2-trichloro-ethyl ester (Intermediate 6)

To a solution of Intermediate 6b (6.01 g, 24.1 mmol) and aqueous NaOH solution (36 mL, 36 mmol) in EtOAc (40 mL) was added 2,2,2-trichloroethyl chloroformate (4.15 mL, 30.1 mmol). The reaction mixture was stirred at RT for 16 h. The layers were separated and the aqueous layer was extracted with EtOAc (40 mL). The combined organics were washed with brine (40 mL), dried (Na₂SO₄), filtered and concentrated in vacuo to afford a brown gum. This was purified by FCC, using 2-7% MeOH in DCM, to afford the title compound. LCMS (Method 3): Rt 3.61 min, m/z 424, 426 [MH⁺].

Intermediate 7

{3-tert-Butyl-1'-[3-(tetrahydro-pyran-2-yloxy)-propyl]-1'H-[1,4']bipyrazolyl-5-yl}-carbamic acid 2,2,2-trichloro-ethyl ester

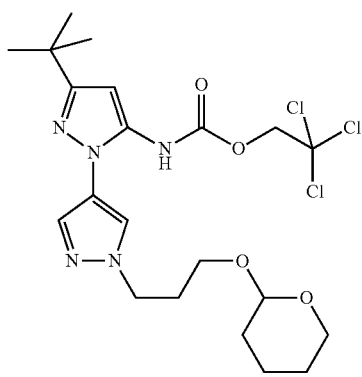 [SMILES: CC(C)(C)c1cc(NC(=O)OCC(Cl)(Cl)Cl)n(-c2cnn(CCCOC3CCCCO3)c2)n1]

a. 4-Iodo-1-[3-(tetrahydro-pyran-2-yloxy)-propyl]-1H-pyrazole (Intermediate 7a)

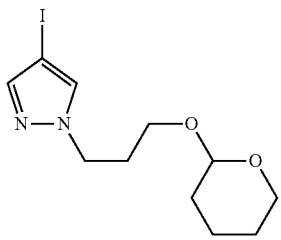 [SMILES: Ic1cnn(CCCOC2CCCCO2)c1]

To a mixture of 4-iodo-1H-pyrazole (2.0 g, 10.3 mmol) and $Cs_2CO_3$ (5.04 g, 15.5 mmol) in MeCN (28 mL) was added 2-(3-bromopropoxy)tetrahydro-2H-pyran (1.84 mL, 10.8 mmol) and the mixture stirred at RT overnight. The crude reaction mixture was poured into water and extracted with EtOAc (×3). The combined organic layers were washed with brine, dried ($MgSO_4$) and concentrated in vacuo. The resulting residue was purified by FCC, using a gradient of 0-80% EtOAc in cyclohexane, to give the title compound (2.95 g, 81%). $^1$H NMR (300 MHz, $CDCl_3$): 150-1.58 (4H, m), 1.65-1.90 (2H, m), 2.12 (2H, qn, J=6.4 Hz), 3.35 (1H, dt, J=10.2, 5.9 Hz), 3.46-3.54 (1H, m), 3.73 (1H, dt, J=10.2, 5.9 Hz), 3.80-3.88 (1H, m), 4.26 (2H, td, J=6.9, 1.5 Hz), 4.54 (1H, dd, J=4.5, 3.1 Hz), 7.46 (1H, s), 7.50 (1H, s).

b. 3-tert-Butyl-1'-[3-(tetrahydro-pyran-2-yloxy)-propyl]-1'H-[1,4']bipyrazolyl-5-ylamine (Intermediate 7b)

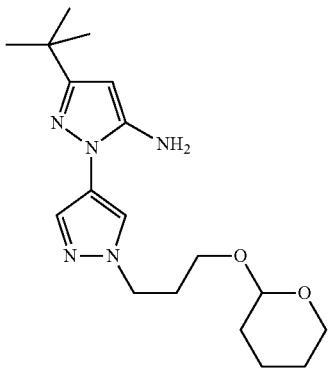 [SMILES: CC(C)(C)c1cc(N)n(-c2cnn(CCCOC3CCCCO3)c2)n1]

To a mixture of Intermediate 7a (1.50 g, 4.46 mmol), 5-tert-butyl-2H-pyrazol-3-ylamine (620 mg, 4.46 mmol), copper (I) iodide (42 mg, 0.22 mmol) and $K_2CO_3$ (1.29 g, 9.37 mmol) was added to toluene (4.6 mL; previously degassed by using a stream of Argon). (R,R)-(−)-N,N'-Dimethyl-1,2-cyclohexanediamine (141 μL, 0.89 mmol) was then added and the reaction mixture was heated at 140° C. for 2.5 h under microwave irradiation. The crude reaction mixture was poured into water and extracted with EtOAc (×3). The combined organic layers were washed with brine, dried ($MgSO_4$) and concentrated in vacuo. The resultant residue was purified by FCC, using a gradient of 0-100% EtOAc in cyclohexane, to give the title compound (1.14 g, 73%). LCMS (Method 4): Rt 2.34 min, m/z 348 [MH$^+$].

c. {3-tert-Butyl-1'-[3-(tetrahydro-pyran-2-yloxy)-propyl]-1'H-[1,4']bipyrazolyl-5-yl}-carbamic acid 2,2,2-trichloro-ethyl ester (Intermediate 7)

To a stirred mixture of Intermediate 7b (1.14 g, 3.28 mmol) in water (6 mL) and EtOAc (12 mL) was added NaOH (263 mg, 6.57 mmol). After 10 min, 2,2,2-trichloro-ethyl chloroformate (543 μL, 3.94 mmol) was added and the reaction mixture was stirred at RT for 1 h. The aqueous layer was extracted with EtOAc (×3) and the combined organic layers were washed with brine, dried ($MgSO_4$) and concentrated in vacuo. The resultant residue was purified by FCC, using a gradient of 0-100% EtOAc in cyclohexane, to afford the title compound (1.57 g, 91%). LCMS (Method 4): Rt 3.99 min, m/z 522, 524 [MH$^+$].

Intermediate A

Methanesulfonic acid 2-[3-tert-butyl-5-(3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester

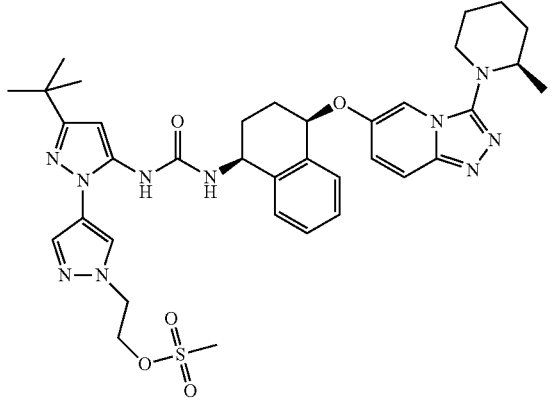 [SMILES: C[C@@H]1CCCCN1c1nnc2ccc(O[C@@H]3CC[C@H](NC(=O)Nc4cc(C(C)(C)C)nn4-c4cnn(CCOS(C)(=O)=O)c4)c4ccccc43)cn12]

a. 1-[3-tert-Butyl-1'-(2-hydroxyethyl)1'H[1,4']bipyrazolyl-5-yl]-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea. (Intermediate Aa)

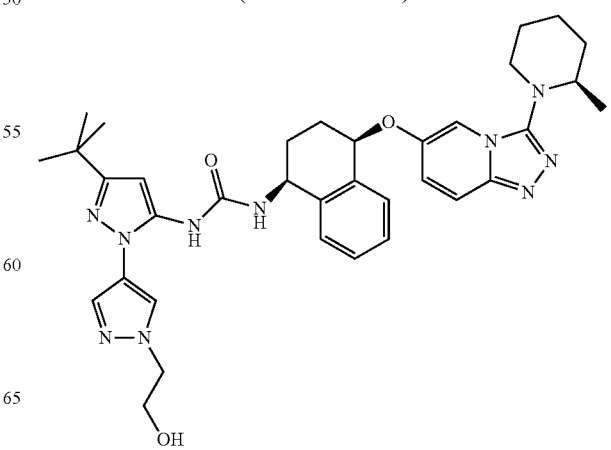

A mixture of Intermediate 6 (100 mg, 0.235 mmol), Intermediate 5 (89 mg, 0.235 mmol) and DIPEA (61 μL, 0.353 mmol) in dioxane (1.5 mL) was heated at 60° C. for 48 h. The mixture was cooled to RT, diluted with DCM (5 mL) and washed with water (5 mL) and brine (5 mL). The organic layer was passed through a phase separator and concentrated in vacuo. The residue was purified by FCC, using 0-10% [2M NH$_3$ in MeOH] in DCM to afford the title compound (77 mg, 50%). LCMS (Method 3): Rt 3.39 min, m/z 653 [MH$^+$].

b. Methanesulfonic acid 2-[3-tert-butyl-5-(3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester. (Intermediate A)

A mixture of Intermediate Aa (75 mg, 0.115 mmol), methanesulfonyl chloride (11.6 μL, 0.149 mmol) and DIPEA (60 μL, 0.345 mmol) in DCM (1 mL) was stirred at RT for 30 min. The reaction mixture was partitioned between DCM (5 mL) and water (2×5 mL). The organic layer was washed with brine (5 mL), separated through a phase separating cartridge and concentrated in vacuo to afford the title compound (84 mg, 100%). LCMS (Method 3): Rt 3.61 min, m/z 731 [MH$^+$].

Intermediate B

Methanesulfonic acid 2-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester. (Intermediate B)

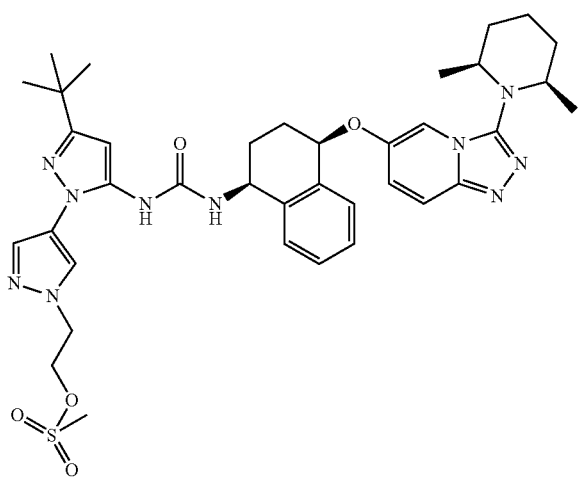 [SMILES: C[C@@H]1CCC[C@H](C)N1c1nnc2ccc(O[C@@H]3CC[C@H](NC(=O)Nc4cc(C(C)(C)C)nn4-c4cnn(CCOS(C)(=O)=O)c4)c4ccccc43)cn12]

a. 1-[3-tert-Butyl-1'-(2-hydroxy-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea. (Intermediate Ba)

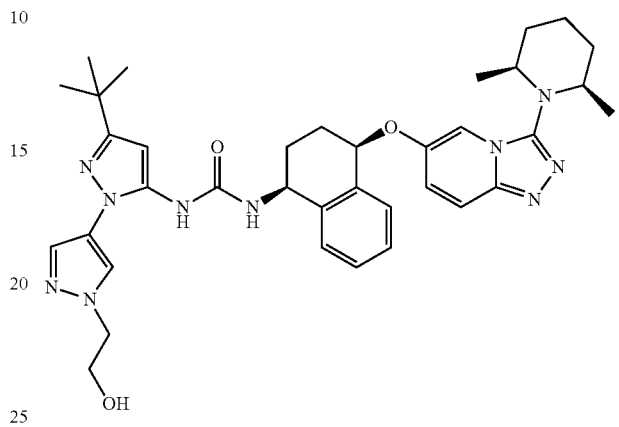

An orange solution of Intermediate 6 (446 mg, 1.05 mmol), Intermediate 3 (392 mg, 1.00 mmol) and DIPEA (218 μL, 1.25 mmol) in dioxane (10 mL) was stirred at 60° C. for 64 h. The cooled solution was concentrated in vacuo, suspended in water (10 mL) and extracted with DCM (2×10 mL). The combined organics were passed through a hydrophobic frit and concentrated in vacuo to leave a brown oil. FCC, using 6-13% MeOH in DCM, gave the title compound (510 mg, 76%). LCMS (Method 3): Rt 3.54 min, m/z 667 [MH$^+$]. $^1$H NMR (300 MHz, CDCl$_3$): 0.60 (3H, d, J 6.3), 0.62 (3H, d, J 6.3), 1.25-1.60 (3H, m), 1.31 (9H, s), 1.68-1.86 (3H, m), 1.93 (1H, t, J 10.6), 2.03-2.25 (3H, m), 3.07-3.24 (2H, m), 3.81 (2H, t, J 4.6), 4.07 (2H, dd, J 5.6, 3.7), 5.10 (1H, td, J 8.6, 5.0), 5.20 (1H, t, J 4.0), 6.37 (1H, s), 6.43 (1H, br d, J 8.6), 6.88 (1H, dd, J 9.8, 2.2), 7.21-7.34 (4H, m), 7.42 (1H, d, J 7.7), 7.62-7.64 (2H, m), 7.70 (1H, s), 7.84 (1H, br s).

b. Methanesulfonic acid 2-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester. (Intermediate B)

To a solution of Intermediate Ba (510 mg, 0.765 mmol) and DIPEA (400 μL, 1.53 mmol) in DCM (10 mL) at RT was added methanesulfonyl chloride (118 μL, 1.53 mmol) and the resulting orange solution stirred at RT for 1 h. Water (5 mL) and sat. aq. NaHCO$_3$ solution (5 mL) were added and the mixture shaken. The aqueous was extracted with DCM (10 mL), then the combined organics passed through a hydrophobic frit and concentrated in vacuo to leave the title compound (100%). LCMS (Method 3): Rt 3.83 min, m/z 745 [MH$^+$].

Intermediate C

Methanesulfonic acid 2-(3-tert-butyl-5-{3-[(1S,4R)-4-(3-dimethylamino-[1,2,4]triazolo[4,3-a]pyridin-6-yloxy)-1,2,3,4-tetrahydro-naphthalen-1-yl]-ureido}-[1,4']bipyrazolyl-1'-yl)-ethyl ester

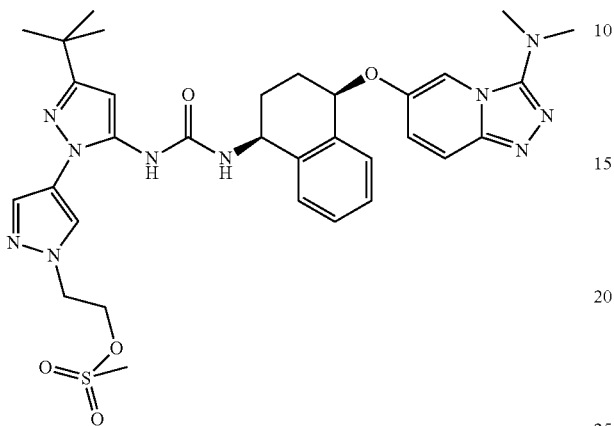

a. 1-[3-tert-Butyl-1'-(2-hydroxy-ethyl)-1'H-[1,4']bipyrazolyl-5-yl]-3-[(1S,4R)-4-(3-dimethylamino-[1,2,4]triazolo[4,3-a]pyridin-6-yloxy)-1,2,3,4-tetrahydro-naphthalen-1-yl]-urea (Intermediate Ca)

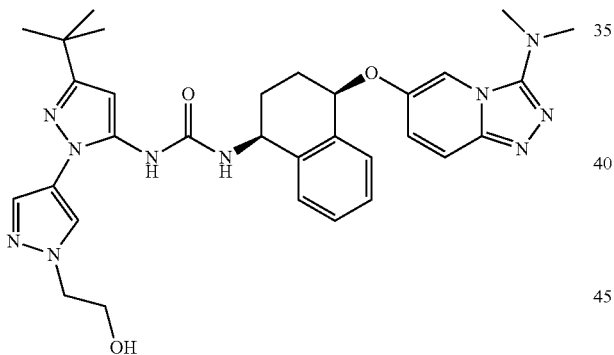

A mixture of Intermediate 6 (254 mg, 0.59 mmol), Intermediate 4 (202 mg, 0.59 mmol) and DIPEA (208 µL, 1.20 mmol) in dioxane (6.0 mL) was stirred at 70° C. for 14 h. The resultant mixture was poured into water and the aqueous phase was extracted with EtOAc (×3). The combined organic layers were washed with brine, dried (MgSO₄) and concentrated in vacuo. The resultant residue was purified by FCC, using a gradient of 0-10% MeOH in DCM, to give the title compound (300 mg, 85%). LCMS (Method 4): Rt 2.64 min, m/z 598 [MH⁺].

b. Methanesulfonic acid 2-(3-tert-butyl-5-{3-[(1S,4R)-4-(3-dimethylamino-[1,2,4]triazolo[4,3-a]pyridin-6-yloxy)-1,2,3,4-tetrahydro-naphthalen-1-yl]-ureido}-[1,4']bipyrazolyl-1'-yl)-ethyl ester. (Intermediate C)

To an ice-bath cooled solution of Intermediate Ca (300 mg, 0.50 mmol) in DCM (5.0 mL) was added DIPEA (349 µL, 2.01 mmol) followed by methanesulfonyl chloride (98.0 µL, 1.00 mmol). The reaction mixture was stirred for 3 h and then quenched with water. The aqueous phase was extracted with DCM (×3) and the combined organic layers were washed with brine, dried (MgSO₄) and concentrated in vacuo to afford the title compound (Quantitative). Product used in the subsequent step without further purification. LCMS (Method 4): Rt 2.86 min, m/z 677 [MH⁺].

Intermediate D

Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester

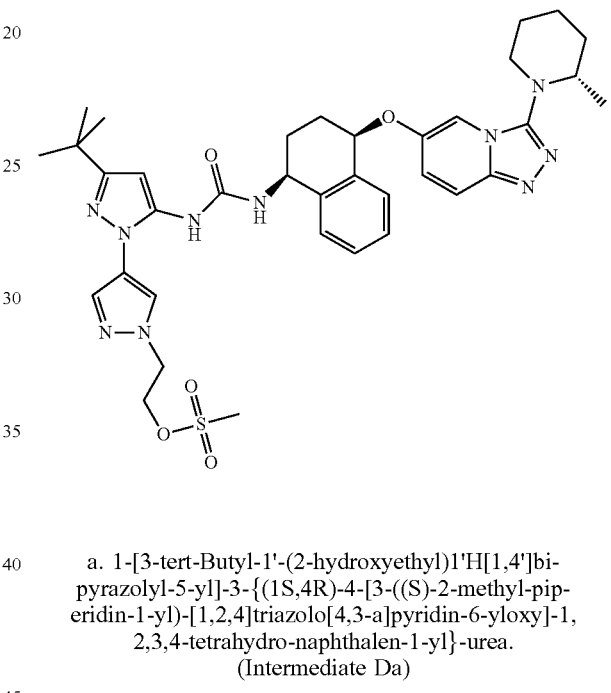

a. 1-[3-tert-Butyl-1'-(2-hydroxyethyl)1'H[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea. (Intermediate Da)

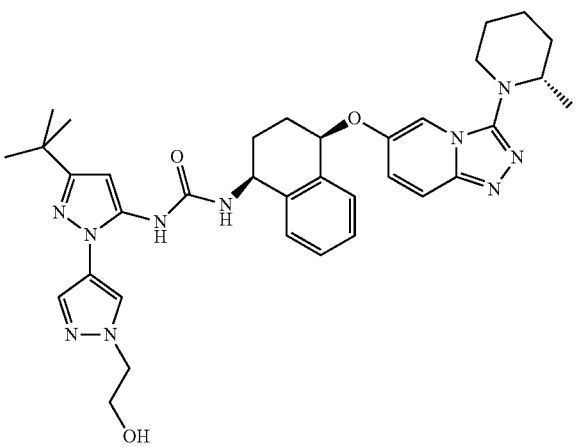 [SMILES: C[C@H]1CCCCN1c1nnc2ccc(O[C@@H]3CC[C@H](NC(=O)Nc4cc(C(C)(C)C)nn4-c4cnn(CCO)c4)c4ccccc43)cn12]

The title compound was prepared starting from Intermediate 6 and Intermediate 2 by using an analogous procedure to that described for Intermediate A step a. LCMS (Method 3): Rt 3.32 min, m/z=653 [MH+].

b. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester. (Intermediate D)

The title compound was prepared starting from Intermediate Da by using an analogous procedure to that described for Intermediate A step b. LCMS (Method 3): Rt 3.54 min, m/z 731 [MH+].

Intermediate E

Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-propyl ester

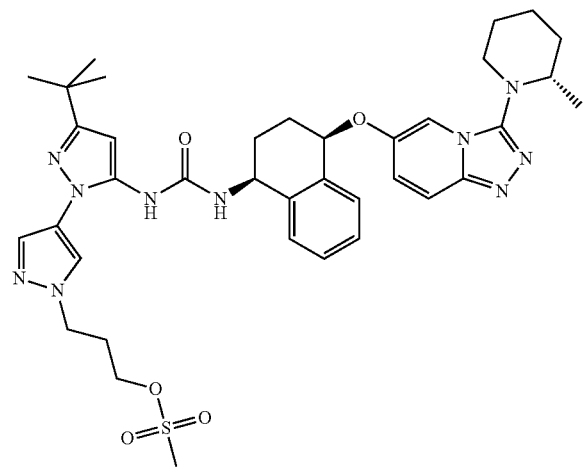 [SMILES: C[C@H]1CCCCN1c1nnc2ccc(O[C@@H]3CC[C@H](NC(=O)Nc4cc(C(C)(C)C)nn4-c4cnn(CCCOS(C)(=O)=O)c4)c4ccccc43)cn12]

a. 1-{3-tert-Butyl-1'-[3-(tetrahydro-pyran-2-yloxy)-propyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate Ea)

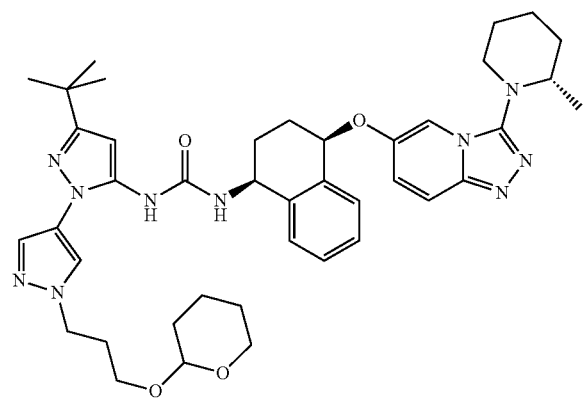 [SMILES: C[C@H]1CCCCN1c1nnc2ccc(O[C@@H]3CC[C@H](NC(=O)Nc4cc(C(C)(C)C)nn4-c4cnn(CCCOC5CCCCO5)c4)c4ccccc43)cn12]

A mixture of Intermediate 7 (865 mg, 1.49 mmol), Intermediate 2 (561 mg, 1.49 mmol) and DIPEA (390 µL, 2.24 mmol) in 2-methyltetrahydrofuran (8 mL) was stirred at 60° C. for 20 h. The mixture was cooled, diluted with water, and extracted with DCM (2×20 mL). The combined organic phases were dried, concentrated in vacuo and the resultant residue was purified by FCC eluting with 0-12% of MeOH in DCM to afford the title compound (958 mg, 86%). LCMS (Method 3): R3.85 min, m/z 751.5 [MH+].

b. 1-[3-tert-Butyl-1'-(3-hydroxy-propyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea. (Intermediate Eb)

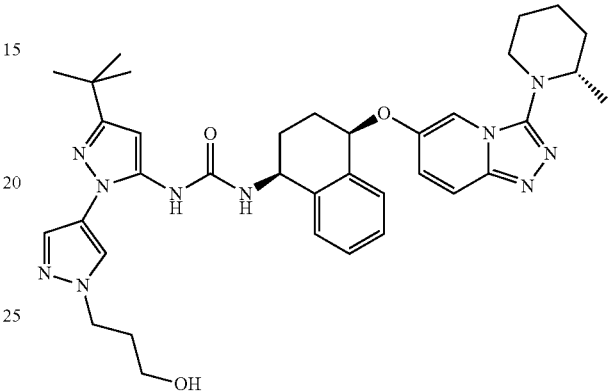

To a solution of Intermediate Ea (930 mg, 1.24 mmol) in methanol (10 mL) was added pyridinium p-toluenesulphonate (930 mg, 3.72 mmol). Mixture was heated to 45° C. for 7 h and 50° C. for 16 h. After cooling, the mixture was diluted with saturated sodium hydrogen carbonate solution, and extracted with DCM (2×25 mL). The combined organic extracts were dried, concentrated in vacuo and the resultant residue was purified by FCC eluting with 0-10% of MeOH in DCM to afford the title compound (719 mg, 87%). LCMS (Method 3): Rt 3.36 min, m/z 667.5 [MH+].

c. Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-propyl ester. (Intermediate E)

A mixture of Intermediate Eb (355 mg, 0.53 mmol), methanesulfonyl chloride (62.0 µL, 0.80 mmol) and DIPEA (272 µL, 1.56 mmol) in DCM (10 mL) was stirred at RT for 0.4 h. The reaction mixture was diluted with saturated sodium hydrogen carbonate solution and extracted with DCM (2×10 mL). The organic layer was passed through a phase separating cartridge and concentrated in vacuo to afford the title compound (400 mg, quantitative). LCMS (Method 3): Rt 3.59 min, m/z 745.4 [MH+].

Examples 1-11 a. General Displacement Procedure

A mixture of Intermediate A-E (0.115 mmol) and an appropriate amine [see table 1] (2.30 mmol) in anhydrous THF (1 mL) was stirred at 60° C. for 18 h in a sealed vial. The volatiles were concentrated in vacuo and the resulting residue was purified by either by MDAP (method 7) or HPLC (Gemini C18, 20-40% MeCN in H₂O, 0.1% HCO₂H, 18 ml/min.) or both to afford the title compound (40-80%). compound (40-80%).

| Example No. | Amine | Intermediate used | Example Structure | NMR (400 MHz) δ | LCMS |
|---|---|---|---|---|---|
| 1 | 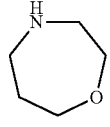<br>[1,4]Oxazepane | D | 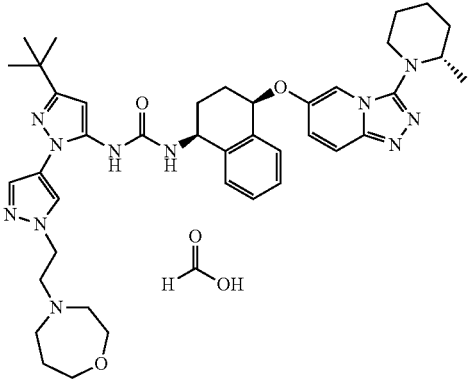 [SMILES: C[C@H]1CCCCN1c1nnc2ccc(O[C@@H]3CC[C@H](NC(=O)Nc4cc(C(C)(C)C)nn4-c4cnn(CCN5CCCOCC5)c4)c4ccccc43)cn12 ; O=CO]<br>1-[3-tert-Butyl-1'-(2-[1,4]oxazepan-4-yl-ethyl)-1'H[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^{1}$H NMR (400 MHz, d$_6$-DMSO): 0.91 (3H, d, J = 6.1 Hz), 1.25 (9H, s), 1.47-1.55 (2H, m), 1.62-2.18 (10H, m), 2.66-2.72 (4H, m), 2.87-2.96 (3H, m), 3.12-3.19 (1H, m, obscured by water), 3.28-3.36 (1H, m, obscured by water), 3.55-3.59 (2H, m), 3.64 (2H, t, J = 5.9 Hz), 4.23 (2H, t, J = 6.8 Hz), 4.80-4.89 (1H, m), 5.52 (1H, t, J = 4.6 Hz), 6.27 (1H, s), 7.15 (1H, d, J = 8.5 Hz), 7.20 (1H, dd, J = 9.8, 2.2 Hz), 7.26-7.31 (1H, m), 7.33-7.40 (3H, m), 7.62-7.66 (2H, m), 7.70 (1H, d, J = 1.8 Hz), 8.00 (1H, s), 8.06 (1H, d, J = 0.5 Hz), 8.17 (0.6H, s). | (Method 5): Rt 3.56 min, m/z 736.4 [MH$^+$]. |
| 2 | 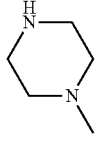<br>1-Methylpiperazine | D | 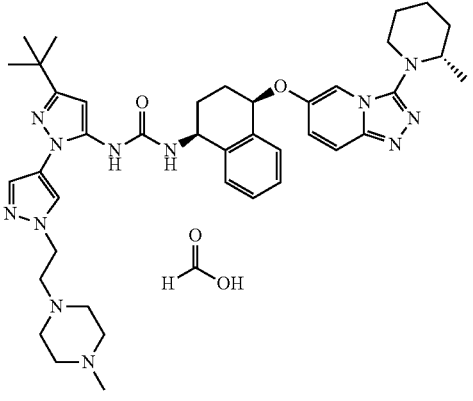 [SMILES: C[C@H]1CCCCN1c1nnc2ccc(O[C@@H]3CC[C@H](NC(=O)Nc4cc(C(C)(C)C)nn4-c4cnn(CCN5CCN(C)CC5)c4)c4ccccc43)cn12 ; O=CO]<br>1-{3-tert-Butyl-1'-[2-(4-methyl-piperazin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^{1}$H NMR (400 MHz, d$_6$-DMSO): 0.91 (3H, d, J = 6.0 Hz), 1.25 (9H, s), 1.47-1.57 (2H, m), 1.62-1.73 (2H, m), 1.74-2.17 (6H, m), 2.14 (3H, s), 2.26-2.38 (4H, br, m), 2.38-2.49 (4H, br, m), 2.73 (2H, t, J = 6.6 Hz), 2.86-2.95 (1H, m), 3.12-3.20 (1H, m), 3.27-3.37 (1H, m), 4.23 (2H, t, J = 6.6 Hz), 4.80-4.89 (1H, m), 5.53 (1H, t, J = 5.5 Hz), 6.27 (1H, s), 7.16 (1H, d, J = 8.3 Hz), 7.20 (1H, dd, J = 10.0, 2.2 Hz), 7.25-7.31 (1H, m), 7.31-7.40 (3H, m), 7.61-7.66 (2H, m), 7.70 (1H, d, J = 2.0 Hz), 8.01 (1H, s), 8.05 (1H, d, J = 0.6 Hz), 8.17 (1H, s). | (Method 5): Rt 3.50 min, m/z 735.4 [MH$^+$]. |
| 3 | 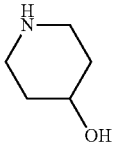<br>Piperidin-4-ol | D | 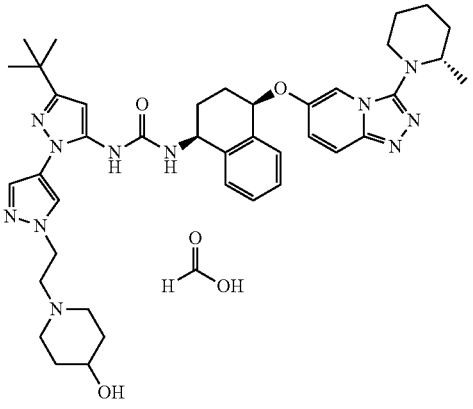 [SMILES: C[C@H]1CCCCN1c1nnc2ccc(O[C@@H]3CC[C@H](NC(=O)Nc4cc(C(C)(C)C)nn4-c4cnn(CCN5CCC(O)CC5)c4)c4ccccc43)cn12 ; O=CO]<br>1-{3-tert-Butyl-1'-[2-(4-hydroxy-piperidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^{1}$H NMR (400 MHz, d$_6$-DMSO): 0.91 (3H, d, J = 6.2 Hz), 1.25 (9H, s), 1.30-1.41 (2H, m), 1.46-1.56 (2H, m), 1.62-1.72 (4H, m), 1.74-2.04 (4H, m), 2.05-2.16 (4H, m), 2.68-2.78 (4H, m), 2.86-2.95 (1H, m), 3.12-3.20 (m, obscured by water), 3.28-3.36 (m, obscured by water), 3.38-3.47 (m, obscured by water), 4.21 (2H, t, J = 6.8 Hz), 4.81-4.88 (1H, m), 5.41 (1H, t, J = 4.5 Hz), 6.27 (1H, s), 7.15 (1H, d, J = 8.5 Hz), 7.20 (1H, dd, J = 9.8, 2.2 Hz), 7.25-7.31 (1H, m), 7.31-7.40 (3H, m), 7.62-7.66 (2H, m), 7.70 (1H, d, J = 2.0 Hz), 8.00 (1H, s), 8.05 (1H, s), 8.16 (1H, s). | (Method 5): Rt 3.50 min, m/z 736.4 [MH$^+$]. |

-continued

| Example No. | Amine | Intermediate used | Example Structure | NMR (400 MHz) δ | LCMS |
|---|---|---|---|---|---|
| 4 | (methoxyethyl-methylamine) | D | 1-(3-tert-Butyl-1'-{2-[(2-methoxy-ethyl)-methyl-amino]-ethyl}-1'H-[1,4']bipyrazolyl-5-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea | $^1$H NMR (400 MHz, d$_6$-DMSO): 0.91 (3H, d, J = 6.2 Hz), 1.25 (9H, s), 1.46-1.57 (2H, m), 1.61-1.73 (2H, m), 1.74-2.01 (4H, m), 2.01-2.18 (2H, m), 2.24 (3H, s), 2.54 (2H, t, J = 5.8 Hz), 2.80 (2H, t, J = 6.6 Hz), 2.87-2.95 (1H, m), 3.13-3.18 (m, obscured by water), 3.19 (3H, s), 3.29-3.34 (m, completely obscured by water), 3.36 (2H, t, J = 5.8 Hz), 4.19 (2H, t, J = 6.6 Hz), 4.80-4.88 (1H, m), 5.53 (1H, t, J = 4.5 Hz), 6.26 (1H, s), 7.17 (1H, dd, J = 8.3 Hz), 7.20 (1H, dd, J = 9.8, 2.2 Hz), 7.25-7.31 (1H, m), 7.32-7.40 (3H, m), 7.62-7.66 (2H, m), 7.70 (1H, d, J = 1.9 Hz), 8.01 (1H, s), 8.06 (1H, s), 8.19 (0.9H, s). | (Method 5): Rt: 3.62 min, m/z 724.6 [MH+]. |
| 5 | Piperidine | B | 1-[3-tert-Butyl-1'-(2-piperidin-1-yl-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.60 (3H, d, J = 6.2 Hz), 0.63 (3H, d, J = 6.2 Hz), 1.25 (9H, s), 1.32-1.38 (2H, m), 1.40-1.60 (7H, m), 1.68-1.74 (2H, m), 1.77-1.92 (2H, m), 1.95-2.02 (1H, m), 2.04-2.12 (2H, m), 2.40 (4H, t, J = 4.9 Hz), 2.71 (2H, t, J = 6.8 Hz), 3.13-3.23 (2H, m), 4.23 (2H, t, J = 6.8 Hz), 4.85 (1H, td, J = 8.5, 5.4 Hz), 5.54 (1H, t, J = 4.4 Hz), 6.26 (1H, s), 7.14 (1H, d, J = 8.5 Hz), 7.21 (1H, dd, J = 9.8, 2.2 Hz), 7.25-7.29 (1H, m), 7.33-7.38 (3H, m), 7.63 (1H, d, J = 0.7 Hz), 7.67 (1H, d, J = 9.8 Hz), 7.89 (1H, d, J = 2.1 Hz), 8.00 (1H, s), 8.05 (1H, s), 8.15 (1H, s). | (Method 5): Rt 3.79 min, m/z 734 [MH$^+$]. |
| 6 | [1,4]oxazepane | B | 1-[3-tert-Butyl-1'-(2-[2,4]oxazepan-4-yl-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.60 (3H, d, J = 6.2 Hz), 0.63 (3H, d, J = 6.2 Hz), 1.25 (9H, s), 1.38-1.60 (3H, m), 1.68-1.83 (5H, m), 1.84-1.92 (1H, m), 1.95-2.01 (1H, m), 2.05-2.12 (2H, m), 2.67-2.71 (4H, m), 2.92 (2H, t, J = 6.6 Hz), 3.13-3.23 (2H, m), 3.57 (2H, t, J = 4.6 Hz), 3.63 (2H, t, J = 6.0 Hz), 4.21 (2H, t, J = 6.6 Hz), 4.85 (1H, td, J = 8.5, 5.4 Hz), 5.54 (1H, t, J = 4.4 Hz), 6.26 (1H, s), 7.15 (1H, d, J = 8.5 Hz), 7.21 (1H, dd, J = 9.8, 2.2 Hz), 7.25-7.30 (1H, m), 7.32-7.38 (3H, m), 7.64 (1H, d, J = 0.7 Hz), 7.67 (1H, d, J = 9.8 Hz), 7.89 (1H, d, J = 2.1 Hz), 8.00 (1H, s), 8.06 (1H, s), 8.17 (1H, s). | (Method 5): Rt 3.71 min, m/z 750.6 [MH$^+$]. |

| Example No. | Amine | Intermediate used | Example Structure | NMR (400 MHz) δ | LCMS |
|---|---|---|---|---|---|
| 7 | Dimethylamine | C | 1-[3-tert-Butyl-1'-(2-dimethylamino-ethyl)-1'H-[1,4']bipyrazolyl-5-yl]-3-[(1S,4R)-4-(3-dimethylamino-[1,2,4]triazolo[4,3-a]pyridin-6-yloxy)-1,2,3,4-tetrahydro-naphthalen-1-yl]-urea formate salt | $^1$H NMR (400 MHz, d$_6$-DMSO): 1.19 (9H, s), 1.76-1.86 (1H, m), 1.87-1.97 (1H, m), 1.98-2.10 (2H, m), 2.12 (6H, s), 2.63 (2H, t, J = 6.5 Hz), 2.83 (6H, s), 4.15 (2H, t, J = 6.5 Hz), 4.79 (1H, td, J = 8.3, 5.4 Hz), 5.50 (1H, t, J = 4.5 Hz), 6.21 (1H, s), 7.07 (1H, dd, J = 9.8, 2.1 Hz), 7.11 (1H, d, J = 8.6 Hz), 7.22-7.32 (3H, m), 7.34 (1H, d, J = 7.6 Hz), 7.55 (1H, d, J = 10.0 Hz), 7.57 (1H, s), 7.76 (1H, d, J = 2.0 Hz), 7.95 (1H, s), 7.99 (1H, s), 8.10 (0.7H, s). | (Method 5): Rt 3.14 min, m/z 626 [MH+]. |
| 8 | Dimethylamine | A | 1-[3-tert-Butyl-1'-(2-dimethylamino-ethyl)-1'H-[1,4']bipyrazolyl-5-yl]-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl]-urea formate salt | $^1$H NMR (400 MHz, d$_6$-DMSO): 0.88 (3H, d, J = 6.4 Hz), 1.25 (9H, s), 1.44-1.56 (2H, m), 1.63-1.72 (2H, m), 1.75-2.01 (4H, m), 2.04-2.13 (2H, m), 2.17 (6H, s), 2.67 (2H, t, J = 6.6 Hz), 2.90-2.99 (1H, m), 3.14-3.21 (1H, m), 3.39 (m, obscured by water), 4.20 (2H, t, J = 6.6 Hz), 4.79-4.88 (1H, m), 5.56 (1H, t, J = 4.4 Hz), 6.27 (1H, s), 7.13-7.21 (2H, m), 7.25-7.41 (4H, m), 7.61-7.66 (2H, m), 7.71 (1H, d, J = 1.0 Hz), 8.01 (1H, s), 8.05 (1H, s), 8.20 (0.5H, s). | (Method 5): Rt 3.52 min, m/z 680.4 [MH$^+$]. |
| 9 | Dimethylamine | E | 1-[3-tert-Butyl-1'-(3-dimethylamino-propyl)-1'H-[1,4']bipyrazolyl-5-yl]-3-{(1S,4R)-4-[3-((S)-2-methyl-piperdin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J 6.4), 1.25 (9H, s), 1.44-1.57 (2H, m), 1.62-1.73 (2H, m), 1.74-2.01 (6H, m), 2.02-2.17 (2H, m), 2.20 (6H, s), 2.33 (2H, t, 7.1), 2.87-2.95 (1H, m), 3.13-3.20 (1H, m), 3.27-3.36 (1H, m), 4.15 (2H, t, J 7.1), 4.81-4.88 (1H, m), 5.53 (1H, t, J 4.4), 6.27 (1H, s), 7.15-7.22 (2H, m), 7.25-7.31 (1H, m), 7.32-7.40 (3H, m), 7.62-7.67 (2H, m), 7.69-7.72 (1H, m), 8.02-8.06 (2H, m), 8.18 (1.4H, s). | (Method 5): Rt 3.53 min, m/z 694.5 [MH$^+$] |

| Example No. | Amine | Intermediate used | Example Structure | NMR (400 MHz) δ | LCMS |
|---|---|---|---|---|---|
| 10 | 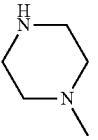<br>1-Methylpiperazine | E | 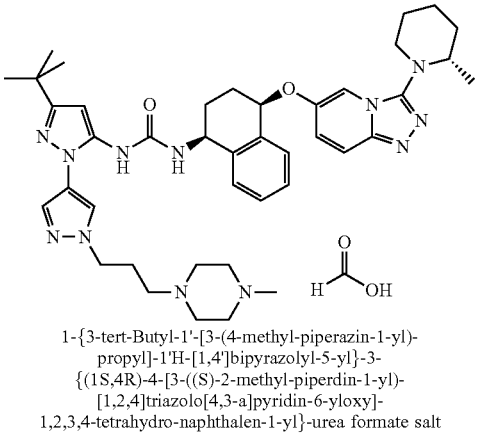<br>1-{3-tert-Butyl-1'-[3-(4-methyl-piperazin-1-yl)-propyl]-1'H-[1,4']bipyrazolyl-5-yl}-3-{(1S,4R)-4-[3-((S)-2-methyl-piperdin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J 6.4), 1.25 (9H, s), 1.44-1.58 (2H, m), 1.62-1.73 (2H, m), 1.74-2.01 (6H, m), 2.02-2.15 (2H, m), 2.16 (3H, s), 2.24-2.48 (10H, m), 2.86-2.95 (1H, m), 3.13-3.20 (1H, m), 3.27-3.36 (1H, m), 4.14 (2H, t, J 7.0), 4.80-4.88 (1H, m), 5.53 (1H, t, J 4.3), 6.26 (1H, s), 7.13-7.22 (2H, m), 7.26-7.31 (1H, m), 7.32-7.40 (3H, m), 7.62-7.67 (2H, m), 7.69-7.72 (1H, m), 7.99-8.04 (2H, m), 8.16 (1.9H, s). | (Method 5): Rt 3.43 min, m/z 749.5 [MH$^+$] |

Example 11

1-[3-tert-Butyl-1'-(2-dimethylamino-ethyl)-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

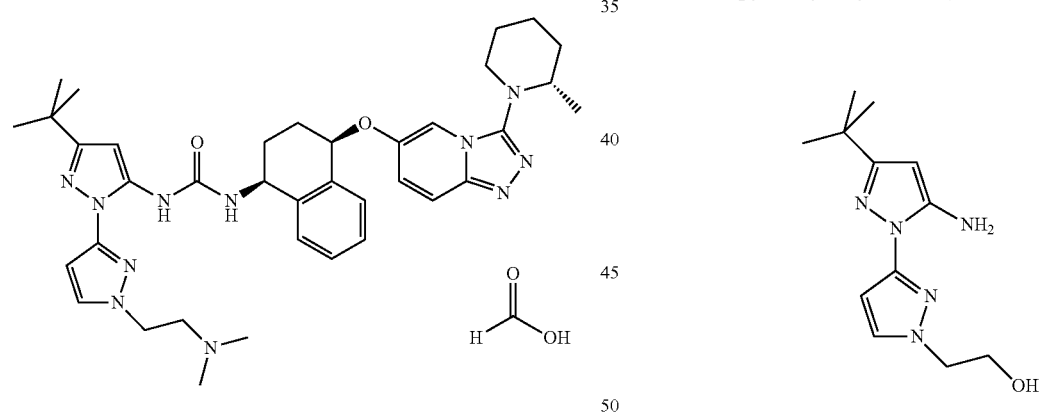

a. 2-(3-Iodo-pyrazol-1-yl-ethanol (Intermediate 11a)

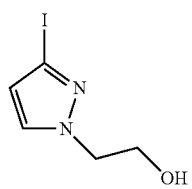

A solution of 3-iodo-1H-pyrazole (500 mg, 2.6 mmol) and ethylene carbonate (238 mg, 2.7 mmol) was formed in DMF (5 mL) and heated at 150° C. for 3 h. The mixture was allowed to cool then evaporated under vacuum to remove the solvent. Purification of the residue by FCC, eluting with a gradient of 0-100% EtOAc in cyclohexane, gave crude title compound (444 mg, 72%). LCMS (Method 3): Rt 2.17 min, m/z 239 [MH$^+$].

b. 3-tert-Butyl-1'-(2-dimethylamino-ethyl)-1'H-[1,3']bipyrazolyl-5-ylamine (Intermediate 11b)

A solution of Intermediate 11a (444 mg, 1.9 mmol), 3-tert-butyl-1H-pyrazole-5-amine (312 mg, 2.2 mmol) and trans-N,N'-dimethyl-cyclohexane-diamine (53.0 mg, 0.4 mmol) was formed in toluene (5 mL). Potassium carbonate (543 mg, 3.9 mmol) was added and the mixture degassed by bubbling nitrogen through it. Copper(I) iodide (36.0 mg, 0.2 mmol) was added and the mixture was sealed in a microwave vial and heated under microwave irradiation at 150° C. for 2 h. The resulting mixture was partitioned between EtOAc/Water and extracted with EtOAc. The combined organics were dried over Na$_2$SO$_4$, filtered and evaporated. Purification by FCC, eluting with a gradient of 25-100% EtOAc in cyclohexane, gave the title compound (200 mg, 43%). LCMS (Method 3): Rt 2.30 min, m/z 250 [MH$^+$].

c. [3-tert-Butyl-1'-(2-hydroxy-ethyl)-1'H-[1,3']bi-pyrazolyl-5-yl]-carbamic acid 2,2,2-trichloro-ethyl ester (Intermediate 11c)

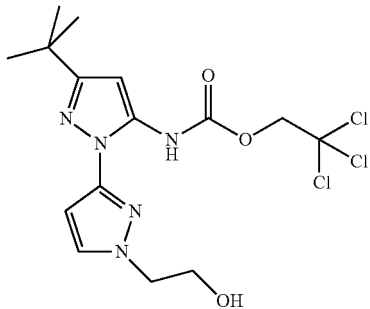 [SMILES: CC(C)(C)c1cc(NC(=O)OCC(Cl)(Cl)Cl)n(-c2ccn(CCO)n2)n1]

A solution of Intermediate 11b (200 mg, 0.80 mmol) was formed in EtOAc (8 mL). Sodium hydroxide solution (1M aqueous, 1.6 mL, 1.60 mmol) was added followed by 2,2,2-trichlororethyl-chloroformate (121 μL, 0.88 mmol). The mixture was stirred at RT over the weekend. The resulting mixture was partitioned between EtOAc/Water and extracted with EtOAc. The combined organics were dried over Na$_2$SO$_4$, filtered and evaporated. Purification by FCC, eluting with a gradient of 0-100% EtOAc in cyclohexane, gave the title compound (277 mg, 82%). LCMS (Method 3): Rt 4.21 min, m/z 424, 426 [MH$^+$].

d. 1-[3-tert-Butyl-1'-(2-hydroxy-ethyl)-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 11d)

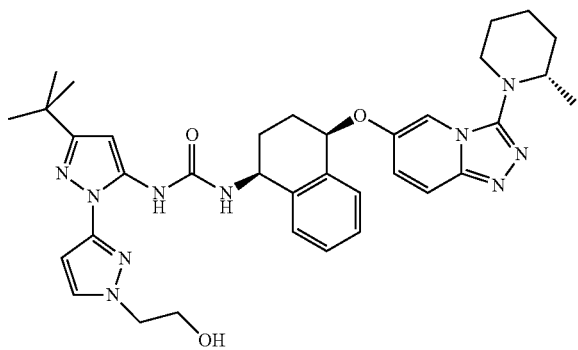 [SMILES: C[C@H]1CCCCN1c1nnc2ccc(O[C@@H]3CC[C@H](NC(=O)Nc4cc(C(C)(C)C)nn4-c4ccn(CCO)n4)c4ccccc43)cn12]

A solution of Intermediate 11c (113 mg, 0.26 mmol), Intermediate 2 (100 mg, 0.26 mmol) and triethylamine (91.0 μL, 0.52 mmol) was formed in dioxane (3 mL) and heated at 90° C. for 24 h, then 110° C. for 4 h. The resulting mixture was partitioned between EtOAc/Water and extracted with EtOAc. The combined organics were dried over Na$_2$SO$_4$, filtered and evaporated. Purification by FCC, eluting with a gradient of 0-10% MeOH in DCM, gave the title compound (92 mg, 54%). LCMS (Method 3): Rt 3.71 min, m/z 653 [MH$^+$].

e. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-umido)-[1,3']bipyrazolyl-1'-yl]-ethyl ester (Intermediate 11e)

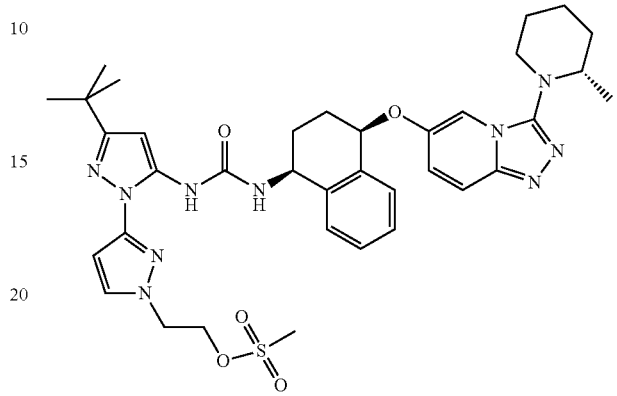

A solution of Intermediate 11d (92.0 mg, 0.14 mmol) and DIPEA (73.0 μL, 0.42 mmol) was formed in DCM (5 mL). Methane sulphonyl chloride (22.0 μL, 0.28 mmol) was added and the mixture stirred at RT for 2 h. Partitioned between water/DCM and isolated the organic fraction passed through a phase separation cartridge. Evaporation gave crude title compound (assumed 100%) which was used in the next step without purification. LCMS (Method 3): Rt 4.01 min, m/z 731 [MH$^+$].

f. 1-[3-tert-Butyl-1'-(2-dimethylamino-ethyl)-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 11)

A solution of Intermediate 11d was formed in a solution of 2M dimethylamine in THF (5 mL) and heated at 60° C. for 16 h. The resulting mixture was allowed to cool to RT then partitioned between EtOAc/Water and extracted with EtOAc. The combined organics were dried over Na$_2$SO$_4$, filtered and evaporated. Purification by FCC, eluting with a gradient of 0-20% MeOH in DCM. Re-dissolved in MeCN (5 mL) and added a couple of drops of formic acid. Evaporated and azeotroped with MeCN. Trituration with Et$_2$O and drying under vacuum gave the title compound (76 mg, 75%). LCMS (Method 5): Rt 3.70 min, m/z 680 [MH$^+$]. $^1$H NMR (400 MHz, d$_6$-DMSO): 0.92 (3H, d, J=6.3 Hz), 1.27 (9H, s), 1.48-1.56 (2H, m), 1.64-1.72 (2H, m), 1.76-1.86 (2H, m), 1.88-2.12 (3H, m), 2.16 (6H, s), 2.18-2.26 (1H, m), 2.67 (2H, t, J=6.3 Hz), 2.88-2.95 (1H, m), 3.14-3.21 (1H, m), 3.29-3.36 (1H, m), 4.23 (2H, t, J=6.3 Hz), 4.90-4.97 (1H, m), 5.54 (1H, t, J=3.8 Hz), 6.32 (1H, d, J=2.3 Hz), 6.42 (1H, s), 7.20 (1H, dd, J=5.0, 2.2 Hz), 7.27-7.42 (4H, m), 7.65 (1H, d, J=10.0 Hz), 7.70 (1H, d, J=7.6 Hz), 7.83 (1H, d, J=2.3 Hz), 7.89 (1H, d, J=8.7 Hz), 8.16 (1H, s), 9.24 (1H, s).

Example 12

1-[3-tert-Butyl-1'-(2-dimethylamino-ethyl)-1'H-[1,3']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

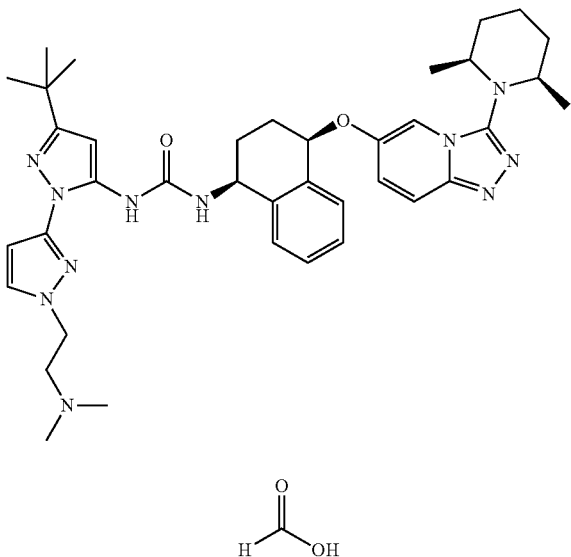 [SMILES: C[C@@H]1CCC[C@H](C)N1c1nnc2ccc(O[C@@H]3CC[C@H](NC(=O)Nc4cc(C(C)(C)C)nn4-c4ccn(CCN(C)C)n4)c4ccccc43)cn12 ; O=CO]

a. 1-[3-tert-Butyl-1'-(2-hydroxy-ethyl)-1'H-[1,3']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 12a)

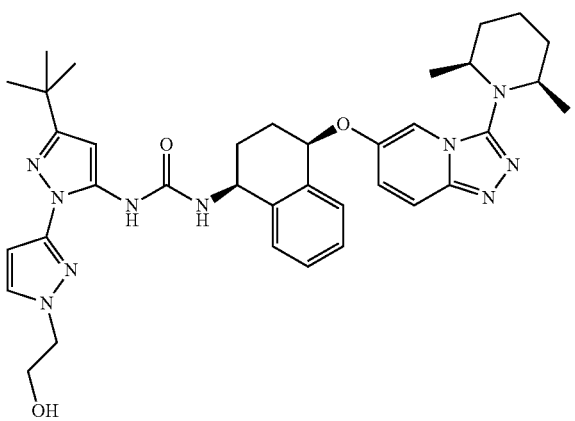 [SMILES: C[C@@H]1CCC[C@H](C)N1c1nnc2ccc(O[C@@H]3CC[C@H](NC(=O)Nc4cc(C(C)(C)C)nn4-c4ccn(CCO)n4)c4ccccc43)cn12]

A mixture of Intermediate 12c (83.0 mg, 195 µmol), Intermediate 3 (76.3 mg, 195 µmol) and DIPEA (102 µL, 585 µmol) in dioxane (2.5 mL) was heated to 60° C. for 90 h and then 80° C. for 24 h. After cooling, the mixture was concentrated in vacuo and the residue was purified by FCC, using 0-10% MeOH in DCM, to provide the title compound as an orange residue (60.0 mg, 46%). LCMS (Method 3): Rt 3.91 min, m/z 667 [MH$^+$].

b. Methanesulfonic acid 2-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-[1,3']bipyrazolyl-1'-yl]-ethyl ester (Intermediate 12b)

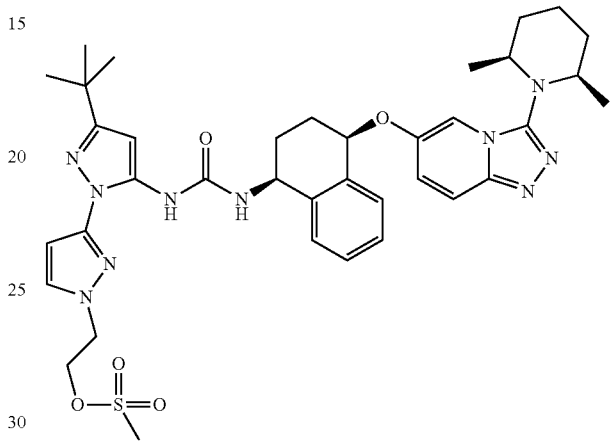

Methanesulfonyl chloride (10.4 µL, 135 µmol) was added to a stirred mixture of Intermediate 12a (60.0 mg, 90.0 µmol), DIPEA (47.0 µL, 270 µmol) in DCM (2 mL) at RT. Stirring was continued for 2 h, and the resulting mixture was diluted with DCM, washed (water, sat. aqueous NaHCO$_3$ solution and brine), passed through a phase separating cartridge and concentrated to dryness. The title compound was isolated as an orange residue, which was used for the next step without further purification. LCMS (Method 3): Rt 4.20 min, m/z 745 [MH$^+$].

c. 1-[3-tert-Butyl-1'-(2-dimethylamino-ethyl)-1'H-[1,3']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt (Example 12)

Intermediate 12b (assumed to be 90.0 µmol) was treated with dimethylamine (2M in THF, 0.9 mL, 1.80 mmol) in THF (1.1 mL) at RT for 96 h. The solvent was removed in vacuo and the residue was purified by MDAP (Method 7) to afford the title compound (27 mg, 43%). LCMS (Method 5): Rt 3.91 min, m/z 694 [MH$^+$]. $^1$H NMR (400 MHz, d$_6$-DMSO): 0.62 (6H, dd, J=10.5, 6.1 Hz), 1.26 (9H, s), 1.40-1.60 (3H, m), 1.72 (2H, m), 1.81 (1H, m), 1.88-2.20 (4H, m), 2.16 (6H, s), 2.66 (2H, t, J=6.2 Hz), 3.19 (m, signal partially obscured by water peak), 4.23 (2H, t, J=6.2 Hz), 4.94 (1H, m), 5.55 (1H, m), 6.32 (1H, d, J=2.5 Hz), 6.42 (1H, s), 7.22 (1H, dd, J=9.6, 2.2 Hz), 7.28 (1H, m), 7.37 (3H, m), 7.66 (1H, d, J=9.5 Hz), 7.83 (1H, d, J=2.2 Hz), 7.88 (2H, m), 8.19 (0.8H, s), 9.24 (1H, br s).

Example 13

1-[5-tert-Butyl-2-(2-dimethylamino-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydronaphthalen-1-yl}-urea formate salt

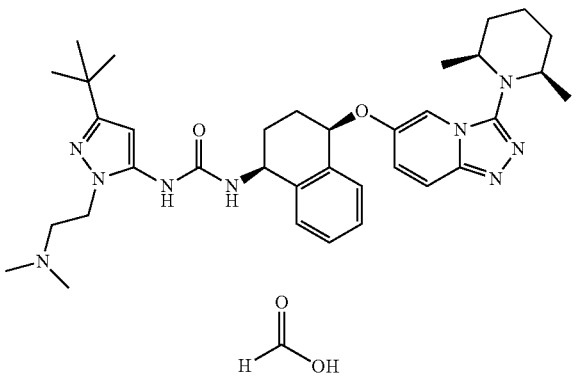

a. 2-(5-Amino-3-tert-butyl-pyrazol-1-yl)-ethanol (Intermediate 13a)

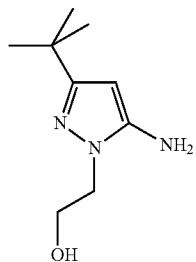

A solution of 4,4-dimethyl-3-oxo-pentanenitrile (5.00 g, 40.0 mmol), concentrated HCl (0.1 mL) and 2-hydrazino ethanol (2.98 mL, 44.0 mmol) in ethanol (40 mL) was refluxed for 20 h. The reaction mixture was then concentrated in vacuo. The resulting solid was washed with cyclohexane (30 mL), and dissolved in MeOH (5 mL) and H$_2$O (5 mL) and lyophilised to give the title compound as a white powder (7.13 g, 97%). LCMS (Method 3): Rt 0.43 min, m/z 184 [MH$^+$].

b. 5-tert-Butyl-2-(2-hydroxyethyl)-2H-pyrazol-3-yl}-carbamic acid 2,2,2-trichloro-ethyl ester (Intermediate 13b)

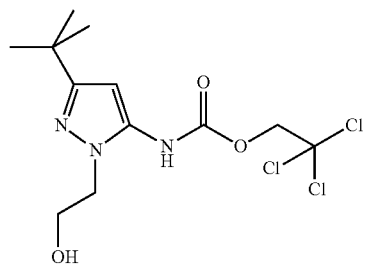 [SMILES: CC(C)(C)c1cc(NC(=O)OCC(Cl)(Cl)Cl)n(CCO)n1]

To a solution of Intermediate 13a (4.11 g, 22.4 mmol) in aqueous NaOH solution (1M, 33.6 mL) and EtOAc (35 mL), at 0° C., was added 2,2,2-trichloro chloroformate (3.24 mL, 23.5 mmol) dropwise over 5 min. The reaction mixture was stirred at RT for 5 h. Additional 2,2,2-trichloro chloroformate (462 µL, 3.36 mmol) was added and the reaction mixture was stirred at RT for a further 16 h. Additional 2,2,2-trichloro chloroformate (462 µL, 3.36 mmol) was added and aqueous NaOH solution (1M, 15 mL) and the reaction mixture was stirred at RT for 1 h. The mixture was extracted with EtOAc (20 mL) and washed with brine (20 mL), dried (Na$_2$SO$_4$), filtered and concentrated in vacuo to afford an orange oil. This was dissolved in cyclohexane (100 mL) and left to stand for 5 days. The suspension was filtered and the solid obtained was washed with cyclohexane (50 mL) and then dried under vacuum, at 45° C. for 20 h to afford the title compound (3.64 g, 45%). The organic extracts were concentrated in vacuo and the residue was purified by FCC, using 50% EtOAc in cyclohexane, to give an orange oil. This was partitioned between DCM (50 mL) and water (50 mL) and the organic layer was passed through a phase separator and concentrated in vacuo to afford additional title compound as an orange gum (1.43 g, 18%). LCMS (Method 3): Rt 3.72 min, m/z 358/360 [MH$^+$].

c. 1-[5-tert-Butyl-2-(2-hydroxy-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 13c)

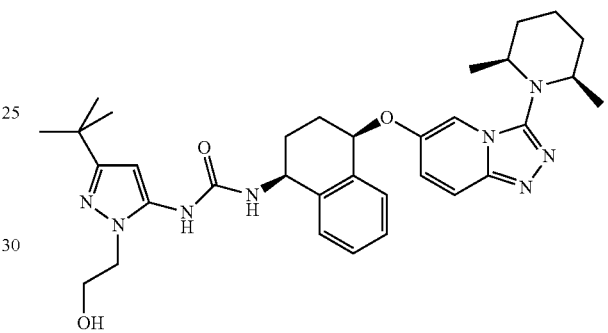

A mixture Intermediate 14b (92.0 mg, 0.26 mmol), Intermediate 3 (100 mg, 0.26 mmol) and DIPEA (67.0 µL, 0.38 mmol) in dioxane (2 mL) was heated at 60° C. for 24 h. The mixture was cooled to RT, diluted with DCM (15 mL) and washed with water (2×15 mL). The organic layer was passed through a phase separator and concentrated in vacuo. The residue was purified by FCC, using 0-10% [2M NH$_3$ in MeOH] in DCM, to afford the title compound (89 mg, 58%). LCMS (Method 3): Rt 3.55 min, m/z 601 [MH$^+$].

d. Methanesulfonic acid 2-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-ethyl ester (Intermediate 13d)

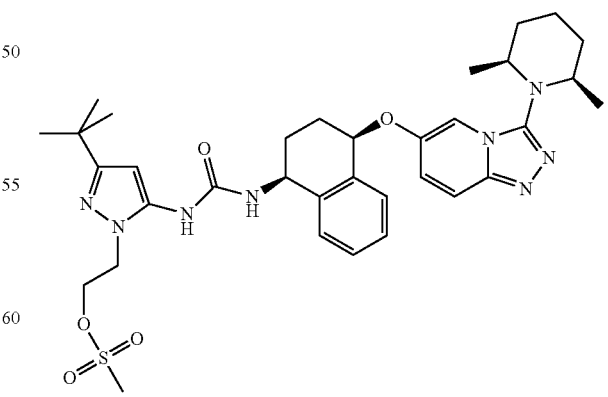

A mixture of Intermediate 13c (85.0 mg, 0.14 mmol), methanesulfonyl chloride (14.0 µL, 0.18 mmol) and DIPEA (74.0 µL, 0.42 mmol) in DCM (1 mL) was stirred at RT for 1 h. The reaction mixture was partitioned between DCM (5 mL) and water (3×5 mL). The organic layer was passed through a phase separating cartridge and concentrated in vacuo to afford the title compound (96 mg, 100%). LCMS (Method 3): Rt 3.81 min, m/z 679 [MH+].

e. 1-[5-tert-Butyl-2-(2-dimethylamino-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydronaphthalen-1-yl}-urea formate salt (Example 13)

A mixture of Intermediate 13d (96.0 mg, 141 μmol) and dimethylamine (2.0M in THF, 1.41 mL, 2.83 mmol) in anhydrous THF (1 mL) was stirred at 60° C. for 18 h in a sealed vial. The volatiles were concentrated in vacuo and the resultant residue was purified by MDAP (method 7) to afford the title compound (44 mg, 49%). LCMS (Method 5): Rt 3.75 min, m/z 628.4 [MH+]. ¹H NMR (400 MHz, d₆-DMSO): 0.61 (3H, d, J=3.2 Hz), 0.63 (3H, d, 3.2 Hz), 1.21 (9H, s), 1.40-1.61 (3H, m), 1.67-1.75 (2H, m), 1.77-1.84 (1H, m), 1.90-2.03 (2H, m), 2.04-2.17 (2H, m), 2.19 (6H, s), 2.60 (2H, t, J=7.0 Hz), 3.13-3.24 (m, obstructed by water), ~3.39 (m, completely obscured by water), 3.99 (2H, t, J=6.9 Hz), 4.84-4.92 (1H, m), 5.55 (1H, t, J=4.0 Hz), 6.03 (1H, s), 7.00 (1H, d, J=8.9 Hz), 7.21-7.30 (2H, m), 7.33-7.42 (3H, m), 7.67 (1H, d, J=9.8 Hz), 7.90 (1H, d, J=1.8 Hz), 8.18 (0.8H, s), 8.48 (1H, s).

Example 14

1-{5-tert-Butyl-2-[5-(2-dimethylamino-ethoxy)-pyridin-3-yl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

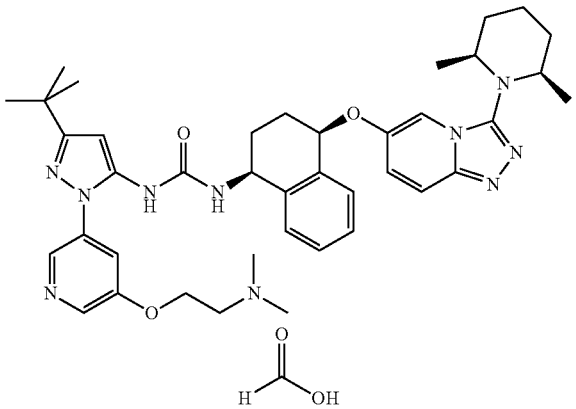

a. 5-(5-Amino-3-tert-butyl-pyrazol-1-yl)-pyridin-3-ol (Intermediate 14a)

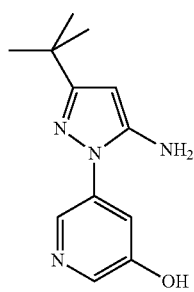 [SMILES: CC(C)(C)c1cc(N)n(-c2cncc(O)c2)n1]

3-(tert-butyl)-1H-pyrazole-5-amine (1.00 g, 7.18 mmol), 3-bromo-5-hydroxypyridine (1.14 g, 6.53 mmol), copper (I) iodide (62.0 mg, 0.33 mmol), K₂CO₃ (1.90 g, 13.7 mmol) and trans-N,N'-dimethylcyclohexane-1,2-diamine (186 mg, 1.31 mmol), were weighed in a 20 mL microwave vial fitted with a stirrer bar and sealed with a crimped septum. The vial was then evacuated and purged with N₂, and anhydrous toluene (10 mL) added. The resulting mixture vacuum degassed and purged with N₂, and then heated at 100° C. for 24 h. The resulting dark suspension was diluted with EtOAc and filtered through Celite, washed with EtOAc and the filtrates concentrated in vacuo. The resulting residue was purified by FCC, eluting with 0-8% MeOH/DCM, to afford the title compound (1.15 g, 76%). LCMS (Method 3): Rt 2.31 min, m/z 233.2 [MH+]. ¹H NMR (300 MHz, CDCl₃): 1.32 (9H, s), 3.49 (1H, s), 5.55 (1H, s), 7.37 (1H, t, J=2.3 Hz), 8.04 (1H, d, J=2.5 Hz), 8.27 (1H, d, J=2.1 Hz).

b. 5-tert-Butyl-2-{5-[2-(tetrahydro-pyran-2-yloxy)-ethoxyl]-pyridin-3-yl}-2H-pyrazol-3-ylamine (Intermediate 14b)

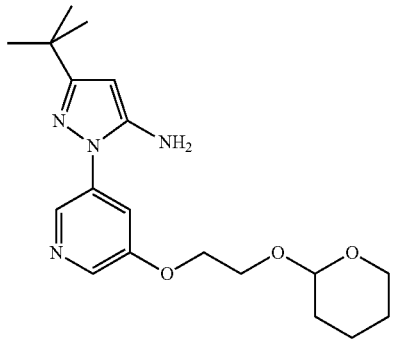 [SMILES: CC(C)(C)c1cc(N)n(-c2cncc(OCCOC3CCCCO3)c2)n1]

To a stirred, ice cooled solution of Intermediate 14a (1.15 g, 4.95 mmol), 2-(tetrahydro-2H-pyran-2-yloxy)ethanol (1.09 g, 7.43 mmol) and triphenylphosphine (2.60 g, 9.90 mmol) in anhydrous THF (30 mL) was added slowly diethyl azodicarboxylate (1.72 g, 1.56 mL, 7.43 mmol) (CARE this resulted in an exotherm). The ice bath was removed, and stirring continued at RT for 45 min. The mixture was then partitioned between water and EtOAc. The organic layer was separated, and the aqueous layer extracted again with EtOAc. The combined organics were dried over MgSO₄, concentrated in vacuo and subjected to FCC, eluting with 0-7% MeOH/DCM, to afford the title compound as a brown oil (637 mg, 36%). LCMS (Method 3): Rt 3.22 min, m/z 361.3 [MH+]. ¹H NMR (300 MHz, CDCl₃): 1.31 (9H, s), 1.46-1.90 (6H, m), 3.47-3.58 (1H, m), 3.75 (2H, br s), 3.80-3.94 (2H, m), 4.08 (1H, dt, J=4.5, 11.5 Hz), 4.23-4.29 (2H, m), 4.67-4.73 (1H, m), 5.56 (1H, s), 7.54 (1H, t, J=2.3 Hz), 8.28 (1H, d, J=2.5 Hz), 8.51 (1H, d, J=1.8 Hz).

c. 2-[5-(5-Amino-3-tert-butyl-pyrazol-1-yl)-pyridin-3-yloxy]-ethanol (Intermediate 14c)

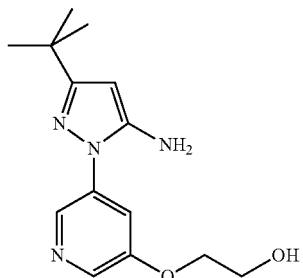

Intermediate 14b (0.64 g, 1.77 mmol), and pyridinium p-toluenesulfonate (1.33 g, 5.30 mmol), were suspended in MeOH (20 mL) and heated to 50° C. for 18 h. The reaction mixture was applied to a 20 g SCX-2 SPE cartridge, washed with MeOH and the product eluted with 2M NH₃ in MeOH, and the basic eluent concentrated in vacuo. The residue was purified by FCC, eluting with 0-8% [2M NH₃ in MeOH] in DCM, to afford the title compound which crystallised (392 mg, 80%). LCMS (Method 3): Rt 2.35 min, m/z 277.3 [MH⁺]. ¹H NMR (300 MHz, CDCl₃): 1.31 (9H, s), 3.97-4.03 (2H, m), 4.14-4.21 (2H, m), 5.57 (1H, s), 7.54 (1H, t, J=2.3 Hz), 8.26 (1H, d, J=2.7 Hz), 8.53 (1H, d, J=2.0 Hz).

d. {5-tert-Butyl-2-[5-(2-hydroxy-ethoxy)-pyridin-3-yl]-2H-pyrazol-3-yl}-carbamic acid 2,2,2-trichloro-ethyl ester (Intermediate 14d)

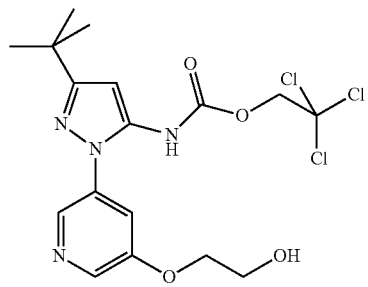 [SMILES: CC(C)(C)c1cc(NC(=O)OCC(Cl)(Cl)Cl)n(-c2cncc(OCCO)c2)n1]

To an ice cooled solution of Intermediate 14c (392 mg, 1.42 mmol) in EtOAc (5 mL) and 1N aqueous NaOH solution (3.6 mL), was added 2,2,2-trichloroethyl chloroformate (331 mg, 215 µL, 1.56 mmol) dropwise, and the ice bath removed and the reaction allowed to warm to RT. An additional 4.4 eq of 2,2,2-trichloroethyl chloroformate was added portionwise at intervals over 6 h, and then stirred for 18 h. The mixture was then partitioned between H₂O and EtOAc, and the organic layer was separated, and the aqueous extracted again with EtOAc. The combined organics were dried over MgSO₄, concentrated in vacuo and subjected to FCC, eluting with 0-5% MeOH/DCM, to afford the title compound as a glassy film (262 mg, 41%). LCMS (Method 3): Rt 3.64 min, m/z 451.1 [MH⁺]. ¹H NMR (300 MHz, CDCl₃): 1.35 (9H, s), 3.98-4.04 (2H, m), 4.15-4.22 (2H, m), 4.81 (2H, s), 6.44 (1H, s), 7.47 (1H, t, J=2.2 Hz), 8.26 (1H, d, J=1.8 Hz), 8.40 (1H, s).

e. 1-{5-tert-Butyl-2-[5-(2-hydroxy-ethoxy)-pyridin-3-yl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 14e)

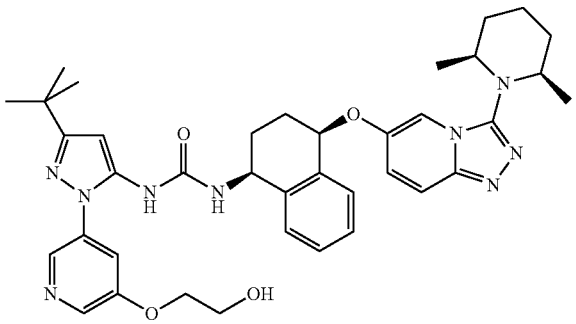 [SMILES: C[C@@H]1CCC[C@H](C)N1c1nnc2ccc(O[C@@H]3CC[C@H](NC(=O)Nc4cc(C(C)(C)C)nn4-c4cncc(OCCO)c4)c4ccccc43)cn12]

A mixture of Intermediate 14d (130 mg, 0.29 mmol), Intermediate 3 (113 mg, 0.29 mmol) and DIPEA (75 µL, 0.43 mmol) in dioxane (5 mL) was stirred at 80° C. for 24 h. The volatiles were concentrated in vacuo and the resultant residue was purified by FCC, eluting with 1-8% [2M NH₃ in MeOH] in DCM, to afford the title compound (160 mg, 80%). LCMS (Method 3): Rt 3.61 min, m/z 694.5 [MH⁺].

f. Methanesulfonic acid 2-{5-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-pyridin-3-yloxy}-ethyl ester (Intermediate 14f)

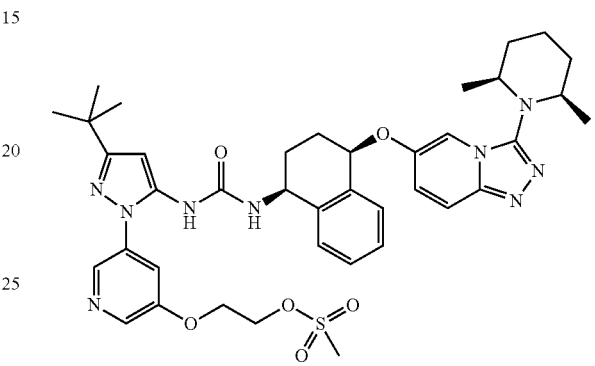

A mixture of Intermediate 14e (160 mg, 0.23 mmol), methanesulfonyl chloride (23 µL, 0.30 mmol) and DIPEA (118 µL, 0.70 mmol) in DCM (5 mL) was stirred at RT for 20 min. The reaction mixture was partitioned between DCM and water, stirred vigorously, separated through a phase separating cartridge and concentrated in vacuo to afford the title compound (178 mg, 100%). LCMS (Method 3): Rt 3.87 min, m/z 771.95 [MH⁺].

g. 1-{5-tert-Butyl-2-[5-(2-dimethylamino-ethoxy)-pyridin-3-yl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt (Example 14)

A mixture of Intermediate 14f (160 mg, 0.21 mmol) and dimethylamine (2.0M in THF, 4 mL, 8.00 mmol) was stirred at 60° C. for 24 h in a sealed vial. The volatiles were concentrated in vacuo and the resultant residue was purified by FCC, eluting with 1-6% [2M NH₃ in MeOH] in DCM. The resulting residue was triturated with pentane/Et₂O. Further purification by reverse-phase HPLC (Method 6) and the product fractions concentrated in vacuo, and triturated with Et₂O and dried in a vacuum oven at 50° C. to afford the title compound (63 mg, 42%). LCMS (Method 5): Rt 3.73 min, m/z 721.5 [MH⁺]. ¹H NMR (400 MHz, d₆-DMSO): 0.60 (3H, d, J=6.2 Hz), 0.63 (3H, d, J=6.2 Hz), 1.29 (9H, s), 1.38-1.63 (3H, m), 1.66-1.75 (2H, m), 1.76-1.98 (3H, m), 2.00-2.15 (2H, m), 2.18 (6H, s), 2.62 (2H, t, J=5.7 Hz), 3.13-3.24 (1H, m), 3.38 (m, obscured by water), 4.16 (2H, t, J=5.6 Hz), 4.76-4.85 (1H, m), 5.52 (1H, t, J=4.1 Hz), 6.37 (1H, s), 7.15 (1H, d, J=8.5 Hz), 7.21 (1H, dd, J=2.2, 9.8 Hz), 7.23-7.29 (2H, m), 7.30-7.37 (2H, m), 7.56 (1H, t, J=2.3 Hz), 7.64-7.69 (1H, m), 7.88 (1H, d, J=1.5 Hz), 8.20 (0.6H, s), 8.28 (1H, s), 8.31 (1H, d, J=2.6 Hz), 8.36 (1H, d, J=2.0 Hz).

Example 15

1-{5-tert-Butyl-2-[5-(2-dimethylamino-ethoxy)-pyridin-3-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

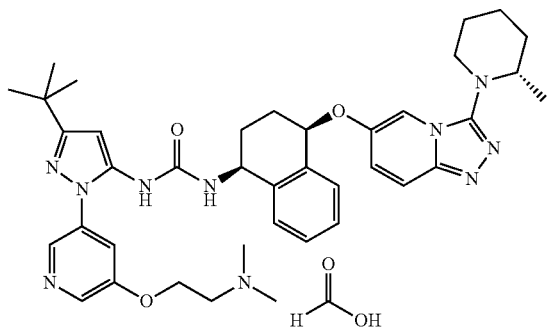

a. 1-{5-tert-Butyl-2-[5-(2-hydroxy-ethoxy)-pyridin-3-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 15a)

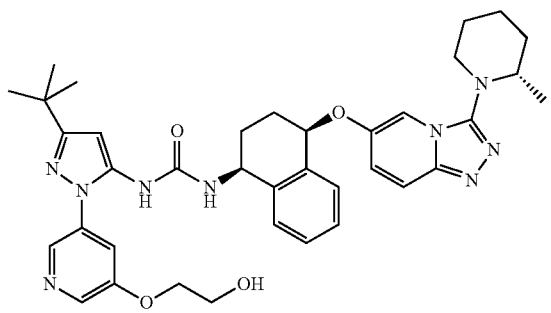 [SMILES: C[C@H]1CCCCN1c1nnc2ccc(O[C@@H]3CC[C@H](NC(=O)Nc4cc(C(C)(C)C)nn4-c4cncc(OCCO)c4)c4ccccc43)cn12]

A mixture of Intermediate 14d (130 mg, 0.29 mmol), Intermediate 2 (109 mg, 0.29 mmol) and DIPEA (75.0 µL, 0.43 mmol) in dioxane (5 mL) was stirred at 80° C. for 24 h. The volatiles were concentrated in vacuo and the resultant residue was purified by FCC, eluting with 1-8% [2M NH₃ in MeOH] in DCM to afford the title compound (158 mg, 81%). LCMS (Method 3): Rt 3.44 min, m/z 680.5 [MH⁺].

b. Methanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-pyridin-3-yloxy}-ethyl ester (Intermediate 15b)

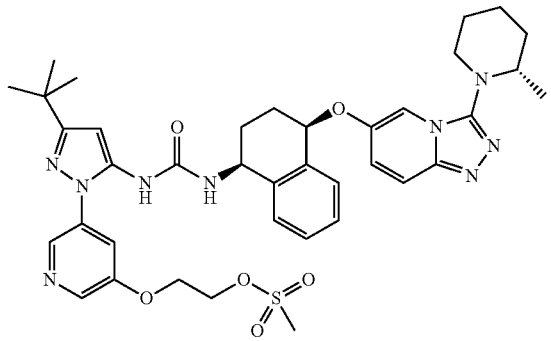 [SMILES: C[C@H]1CCCCN1c1nnc2ccc(O[C@@H]3CC[C@H](NC(=O)Nc4cc(C(C)(C)C)nn4-c4cncc(OCCOS(C)(=O)=O)c4)c4ccccc43)cn12]

A mixture of Intermediate 15a (158 mg, 0.23 mmol), methanesulfonyl chloride (23.0 µL, 0.30 mmol) and DIPEA (119 µL, 0.70 mmol) in DCM (5 mL) was stirred at RT for 20 min. The reaction mixture was partitioned between DCM and water, stirred vigorously, separated through a phase separating cartridge and concentrated in vacuo to afford the title compound (176 mg, 100%). LCMS (Method 3): Rt 3.66 min, m/z 758.4 [MH⁺].

c. 1-{5-tert-Butyl-2-[5-(2-dimethylamino-ethoxy)-pyridin-3-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 15)

A mixture of Intermediate 15b (176 mg, 0.23 mmol) and dimethylamine (2.0M in THF, 4 mL, 8.00 mmol) was stirred at 60° C. for 5 h in a sealed vial. The volatiles were concentrated in vacuo and the resultant residue was purified by FCC, eluting with 1-7% [2M NH₃ in MeOH] in DCM. Further purification by reverse-phase HPLC (Method 6) and the product fractions concentrated in vacuo, and triturated with Et₂O and dried in a vacuum oven at 50° C., to afford the title compound (53 mg, 32%). LCMS (Method 5): Rt 3.56 min, m/z 707.5 [MH⁺]. ¹H NMR (400 MHz, d₆-DMSO): 0.87 (3H, d, J=6.4 Hz), 1.25 (9H, s), 1.42-1.53 (2H, m) 1.58-1.69 (2H, m), 1.70-1.92 (3H, m), 1.94-2.05 (1H, m), 2.05-2.12 (1H, m), 2.14 (6H, s), 2.59 (2H, t J=5.6 Hz), 2.82-2.91 (1H, m), 3.08-3.16 (1H, m), 3.28 (m, obscured by water), 4.13 (2H, t, J=5.9 Hz), 4.72-4.81 (1H, m), 5.47 (1H, t, J=4.1 Hz), 6.33 (1H, s), 7.1 (1H, d, J=8.6 Hz), 7.15 (1H, dd, J=2.1, 9.8 Hz), 7.19-7.26 (2H, m), 7.26-7.35 (2H, m), 7.51 (1H, t, J=2.4 Hz), 7.6 (1H, d, J=9.9 Hz), 7.65 (1H, d, J=1.7 Hz), 8.15 (0.7H, s), 8.23 (1H, s), 8.28 (1H, d, J=2.6 Hz), 8.32 (1H, d, J=2.0 Hz).

Example 16

1-{5-tert-Butyl-2-[6-(2-dimethylamino-ethoxy)-pyridin-2-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

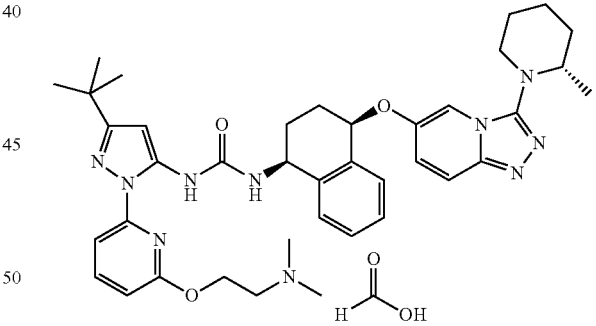

a. 5-tert-Butyl-2-[6-(2-dimethylamino-ethoxy)-pyridin-2-yl]-2H-pyrazol-3-ylamine (Intermediate 16a)

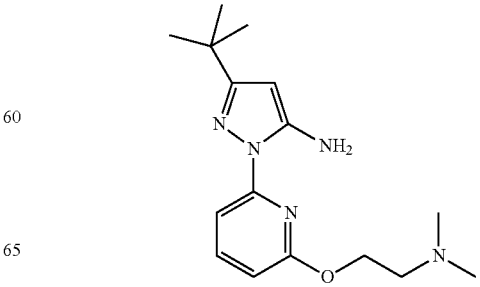

A solution of [2-(6-bromo-pyridin-2-yloxy)-ethyl]-dimethyl-amine (WO2003/082278, 500 mg, 2.00 mmol), 3-tert-butyl-1H-pyrazole-5-amine (341 mg, 2.50 mmol) and trans-N,N'-dimethyl-cyclohexane-diamine (58.0 mg, 0.40 mmol) was formed in toluene (5 mL). Potassium carbonate (592 mg, 4.30 mmol) was added and the mixture degassed by bubbling N₂ through it. Copper(I) iodide (39.0 mg, 0.20 mmol) was added and the mixture was sealed in a microwave vial and heated using microwave irradiation at 150° C. for 2 h. The resulting mixture was partitioned between EtOAc/Water and extracted with EtOAc. The combined organics were dried over Na₂SO₄, filtered and evaporated. Purification by FCC, eluting with a gradient of 0-10% [2M NH₃/MeOH] in DCM, gave the crude title compound (428 mg, 69%) as a brown oil. LCMS (Method 3): Rt 2.29 min, m/z 304 [MH⁺].

b. {5-tert-Butyl-2-[6-(2-dimethylamino-ethoxy)-pyridin-2-yl]-2H-pyrazol-3-yl}-carbamic acid 2,2,2-trichloro-ethyl ester (Intermediate 16b)

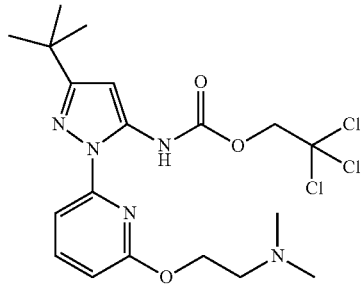 [SMILES: CN(C)CCOc1cccc(-n2nc(C(C)(C)C)cc2NC(=O)OCC(Cl)(Cl)Cl)n1]

A solution of Intermediate 16a (100 mg, 0.33 mmol) was formed in DCM (3 mL). Pyridine (40.0 µL, 0.49 mmol) was added followed by 2,2,2-trichlororethyl-chloroformate (50.0 µL, 0.36 mmol). The mixture was stirred at RT for 1 h. Further 2,2,2-trichlororethyl-chloroformate (25.0 µL, 0.18 mmol) was added and the mixture stirred at RT for 1 h. The mixture was partitioned between DCM/Water and the phases were separated through a phase separation cartridge and evaporated. Purification by FCC, eluting with a gradient of 0-10% MeOH in DCM, gave the title compound (115 mg, 73%). LCMS (Method 3): Rt 3.10 min, m/z 478, 480 [MH⁺].

c. 1-{5-tert-Butyl-2-[6-(2-dimethylamino-ethoxy)-pyridin-2-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 16)

A solution of Intermediate 16b (115 mg, 0.24 mmol), Intermediate 2 (91.0 mg, 0.24 mmol) and triethylamine (84.0 µL, 0.48 mmol) was formed in dioxane (3 mL) and heated at 80° C. for 72 h. The resulting mixture was partitioned between EtOAc/Water and extracted with EtOAc. The combined organics were dried over Na₂SO₄, filtered and evaporated. Purification by FCC, eluting with a gradient of 0-20% MeOH in DCM, followed by further purification using MDAP (method 7) gave the title compound (35 mg, 20%). LCMS (Method 5): Rt 3.98 min, m/z 707.5 [MH⁺]. ¹H NMR (400 MHz, d₆-DMSO): 0.91 (3H, d, J=6.3 Hz), 1.29 (9H, s), 1.46-1.55 (2H, m), 1.65-1.72 (2H, m), 1.76-1.86 (2H, m), 1.87-1.95 (1H, m), 1.98-2.11 (2H, m), 2.06 (6H, s), 2.17-2.24 (1H, m), 2.59 (2H, t, J=6.4 Hz), 2.88-2.95 (1H, m), 3.14-3.20 (1H, m), 3.29-3.35 (1H, m), 4.40-4.45 (2H, m), 4.90-4.96 (1H, m), 5.54 (1H, t, J=3.9 Hz), 6.52 (1H, s), 6.71 (1H, d, J=8.4 Hz), 7.17 (1H, dd, J=4.9, 2.2 Hz), 7.26-7.31 (1H, m), 7.34-7.42 (4H, m), 7.64-7.69 (2H, m), 7.78 (1H, d, J=8.7 Hz), 7.87 (1H, t, J=7.9 Hz), 8.17 (1H, s), 9.80 (1H, s).

Example 17

1-[3-tert-Butyl-1'-(2-dimethylamino-ethyl)-1'H-[1,4']bipyrazolyl-5-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea formate salt

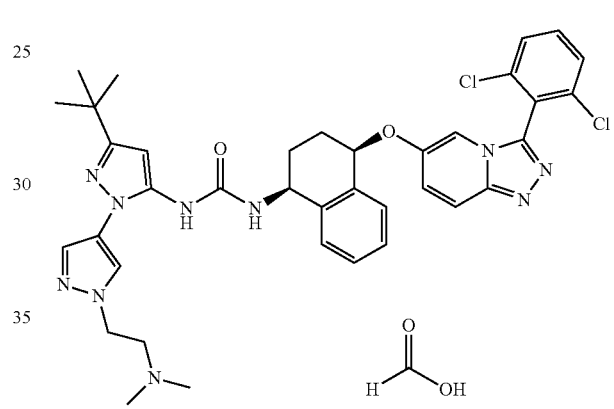

a. 2,6-Dichloro-benzoic acid N'-(5-fluoro-pyridin-2-yl)-hydrazide (Intermediate 17a)

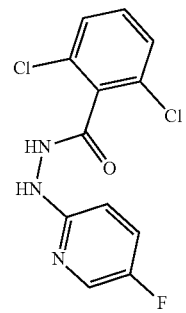 [SMILES: O=C(NNc1ccc(F)cn1)c1c(Cl)cccc1Cl]

DIPEA (2.73 mL, 15.7 mmol) was added dropwise to a solution of (5-fluoro-pyridin-2-yl)-hydrazine (For reference procedure see WO2010022076; 1.00 g, 7.87 mmol) and 2,6-dichloro-benzoyl (1.65 g, 7.87 mmol) in DCM (50 mL). The reaction mixture was stirred at RT for 30 min and then suspended in DCM and Water. The resulting suspension was filtered and the solid was washed with water and air dried to afford the title compound (1.66 g, 71%). LCMS (Method 3): Rt 3.04 min, m/z 300, 302 [MH+].

b. 3-(2,6-Dichloro-phenyl)-6-fluoro-[1,2,4]triazolo[4,3-a]pyridine (Intermediate 17b)

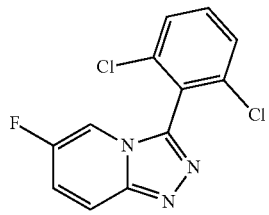 [SMILES: Fc1ccc2nnc(-c3c(Cl)cccc3Cl)n2c1]

Hexachloroethane (2.60 g, 11.0 mmol) was added portionwise over 5 min at RT to a stirred mixture of Intermediate 17a (1.65 g, 5.50 mmol), triphenylphosphine (2.88 g, 11.0 mmol) and triethylamine (3.06 mL, 22.0 mmol) in THF (50 mL). The reaction mixture was stirred at RT for 18 h and then allowed to stand at RT for 72 h. The resulting suspension was filtered and the filtrate was concentrated in vacuo and purified by FCC using SCX-2 cartridge. The cartridge was washed with MeOH and the product was eluted with 2M NH₃ in MeOH to give the title compound (1.44 g, 93%). LCMS (Method 3): Rt 3.08 min, m/z 282, 284 [MH+].

c. (1S,4R)-4-[3-(2,6-Dichloro-phenyl)-[1,2,4]triazolo[4,3-a]pyridin-6-yloxy]-1,2,3,4-tetrahydro-naphthalen-1-ylamine (Intermediate 17c)

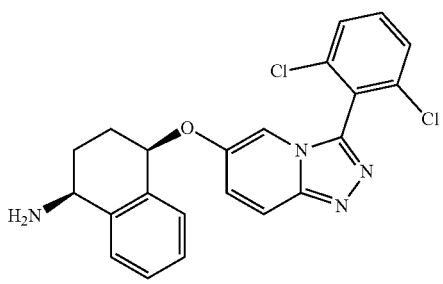 [SMILES: N[C@H]1CC[C@@H](Oc2ccc3nnc(-c4c(Cl)cccc4Cl)n3c2)c2ccccc21]

Intermediate 1 (404 mg, 2.48 mmol) was added to a stirred solution of sodium hydride (60% in mineral oil, 298 mg, 7.44 mmol) in anhydrous DMF (15 mL) at RT under an Argon atmosphere. The reaction mixture was stirred at RT for 15 min, then Intermediate 17b (0.70 g, 2.48 mmol) was added and stirring was continued at 60° C. for 1 h. After cooling, the reaction mixture was quenched by careful addition of a saturated aqueous NH₄Cl solution and Water (1:1) and extracted with EtOAc (×3). The combined organic layers were washed with a saturated aqueous NaHCO₃ solution, followed by brine, dried and concentrated in vacuo. The resultant residue was purified by FCC, using 0-20% [2M NH₃ in MeOH] in DCM, to afford the title compound (345 mg, 33%) as a brown residue. LCMS (Method 3): Rt 2.34 min, m/z 425, 427 [MH+].

d. 1-[3-tert-Butyl-1'-(2-hydroxy-ethyl)-1'H-[1,4']bipyrazolyl-5-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea (Intermediate 17d)

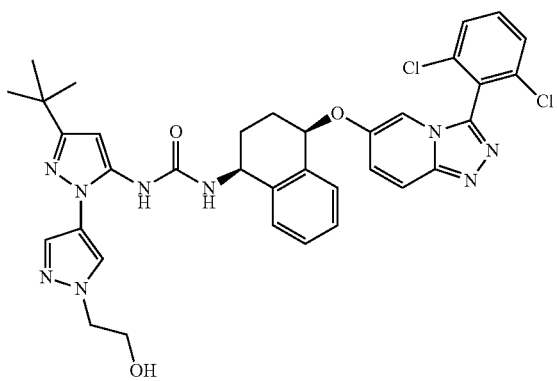 [SMILES: CC(C)(C)c1cc(NC(=O)N[C@H]2CC[C@@H](Oc3ccc4nnc(-c5c(Cl)cccc5Cl)n4c3)c3ccccc32)n(-c2cnn(CCO)c2)n1]

A mixture of Intermediate 6 (118 mg, 279 µmol), Intermediate 17c (108 mg, 254 µmol) and DIPEA (73.0 µL, 419 µmol) in dioxane (2.5 mL) was stirred at 60° C. for 42 h. After cooling, the mixture was diluted with DCM, washed (water and brine) and concentrated to dryness. The residue was purified by FCC, using 0-10% MeOH in DCM, to afford the title compound (160 mg, 90%). LCMS (Method 3): Rt 3.54 min, m/z 700, 702 [MH+].

e. Methanesulfonic acid 2-[3-tert-butyl-5-(3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester (Intermediate 17e)

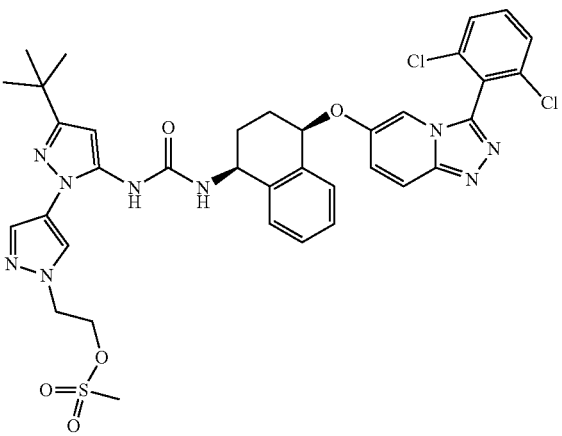 [SMILES: CC(C)(C)c1cc(NC(=O)N[C@H]2CC[C@@H](Oc3ccc4nnc(-c5c(Cl)cccc5Cl)n4c3)c3ccccc32)n(-c2cnn(CCOS(C)(=O)=O)c2)n1]

A mixture of Intermediate 17d (160 mg, 228 μmol), methanesulfonyl chloride (26.5 μL, 342 μmol) and DIPEA (119 μL, 684 μmol) in DCM (5 mL) was stirred at RT for 2 h. The reaction mixture was partitioned between DCM and Water. The organic layer was washed (water (2×), and brine) and then passed through a phase separating cartridge and concentrated in vacuo to afford the title compound (140 mg, 79%). LCMS (Method 3): Rt 3.78 min, m/z 778, 780 [MH+].

f. 1-[3-tert-Butyl-1'-(2-dimethylamino-ethyl)-1'H-[1, 4']bipyrazolyl-5-yl]-3-{(1S,4R)-4-[3-(2,6-dichloro-phenyl)-[1,2,4]triazolo[4,3-a]pyridin-6-yloxy]-1,2,3, 4-tetrahydro-naphthalen-1-yl}-urea formate salt (Example 17)

A mixture of Intermediate 17e (140 mg, 180 μmol) and dimethylamine (2.0M in THF, 0.9 mL, 1.80 mmol) in THF (1.1 mL) was stirred at RT for 48 h in a sealed vial. The mixture was diluted with DCM, washed (water and brine) and concentrated to dryness. The resulting residue was purified by MDAP (Method 7) to afford the title compound (75 mg, 57%). LCMS (Method 5): Rt 3.68 min, m/z 727 [MH+]. ¹H NMR (400 MHz, d₆-DMSO): 1.24 (9H, s), 1.80-2.10 (4H, m), 2.17 (6H, s), 2.68 (2H, t, J=6.4 Hz), 4.21 (2H, t, J=6.4 Hz), 4.81 (1H, m), 5.53 (1H, t, J=4.5 Hz), 6.25 (1H, s), 7.13 (1H, d, J=8.4 Hz), 7.26 (1H, m), 7.29-7.36 (4H, m), 7.62 (1H, d, J=0.9 Hz), 7.69-7.79 (3H, m), 7.90 (1H, d, J=9.7 Hz), 7.97 (1H, d, J=1.8 Hz), 7.99 (1H, s), 8.04 (1H, s), 8.16 (1H, s).

Example 18

1-[3-tert-Butyl-1'-(2-dimethylamino-ethyl)-1'H-[1,4'] bipyrazolyl-5-yl]-3-[(1S,4R)-4-(3-isopropyl-[1,2,4] triazolo[4,3-a]pyridin-6-yloxy)-1,2,3,4-tetrahydro-naphthalen-1-yl]-urea

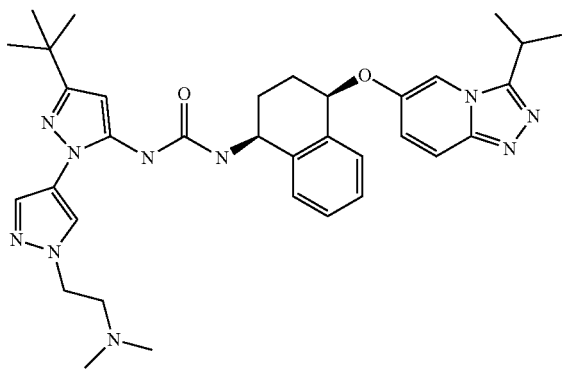 [SMILES: CC(C)c1nnc2ccc(O[C@@H]3CC[C@H](NC(=O)Nc4cc(C(C)(C)C)nn4-c4cnn(CCN(C)C)c4)c4ccccc43)cn12]

a. Isobutyric acid N'-(5-fluoro-pyridin-2-yl)-hydrazide (Intermediate 18a)

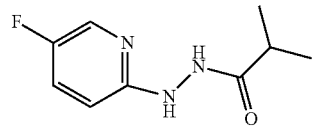

EDC (11.25 g, 58.6 mmol) was added portionwise to a solution of (5-fluoro-pyridin-2-yl)-hydrazine (For reference procedure see WO2010022076; 6.2 g, 48.8 mmol), isobutyric acid (5.15 g, 58.4 mmol) and HOBt (0.66 g, 4.88 mmol) in DCM (200 mL). The reaction mixture was stirred at RT for 2 h before being washed with saturated aqueous Na₂CO₃ solution, dried on Na₂SO₄ and concentrated in vacuo. The residue was triturated with diethyl ether to afford the title compound (6.15 g, 64%). ¹H NMR (300 MHz, CDCl₃): 1.23 (6H, d, J=6.9 Hz), 2.49 (1H, septet, J=6.9 Hz), 6.64 (1H, dd, J=9.0, 3.5 Hz), 6.76 (1H, br), 7.24-7.32 (1H, m), 7.71 (1H, br), 8.02 (1H, d, J=2.8 Hz).

b. 6-Fluoro-3-isopropyl-[1,2,4]triazolo[4,3-a]pyridine (Intermediate 18b)

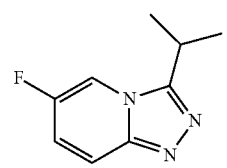

Hexachloroethane (14.6 g, 61.9 mmol) was added to a stirred mixture of Intermediate 18a (6.10 g, 31.0 mmol), triphenylphosphine (16.2 g, 61.9 mmol) and triethylamine (12.5 g, 123.8 mmol) in THF (110 mL) pre-cooled in an ice bath. The reaction mixture was stirred for 30 min then at RT for 1.5 h. The resulting suspension was filtered, and the filtrate concentrated in vacuo. The residue was purified by FCC, using SCX-2 cartridge: The cartridge was washed with MeOH and the product then eluted with 2M NH₃ in MeOH to give the title compound (4.49 g, 81%). ¹H NMR (300 MHz, CDCl₃): 1.54 (6H, d, J=6.9 Hz), 3.32 (1H, septet, J=6.9 Hz), 7.17 (1H, ddd, J=10.0, 7.5, 2.2 Hz), 7.73-7.80 (1H, m), 7.81-7.86 (1H, m).

c. (1S,4R)-4-(3-Isopropyl-[1,2,4]triazolo[4,3-a]pyridin-6-yloxy)-cis-1,2,3,4-tetrahydro-naphthalen-1-ylamine (Intermediate 18c)

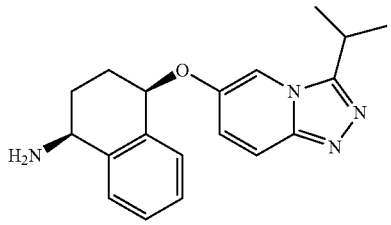 [SMILES: CC(C)c1nnc2ccc(O[C@@H]3CC[C@H](N)c4ccccc43)cn12]

Intermediate 1 (0.48 g, 2.94 mmol) was added to a stirred solution of sodium hydride (60% in mineral oil, 0.34 g, 8.50 mmol) in anhydrous DMF (15 mL) at RT under an Argon atmosphere. The reaction mixture was stirred at RT for 45 min, then Intermediate 18b (0.50 g, 2.79 mmol) was added and stirred at 50° C. for 2 h. After cooling, the reaction mixture was quenched by careful addition of a saturated aqueous NH$_4$Cl solution and water (1:1), and extracted with DCM (8×50 mL). The combined organic layers were washed with water followed by brine, dried and concentrated in vacuo. The resultant residue was purified by FCC, using 0-10% [2M NH$_3$ in MeOH] in DCM, to afford the title compound (0.61 g, 67%) as a brown residue. LCMS (Method 3): Rt 1.98 min, m/z 323 [MH$^+$].

d. 1-[3-tert-Butyl-1'-(2-hydroxy-ethyl)-1'H-[1,4']bipyrazolyl-5-yl]-3-[(1S,4R)-4-(3-isopropyl-[1,2,4]triazolo[4,3-a]pyridin-6-yloxy)-1,2,3,4-tetrahydro-naphthalen-1-yl]-urea (Intermediate 18d)

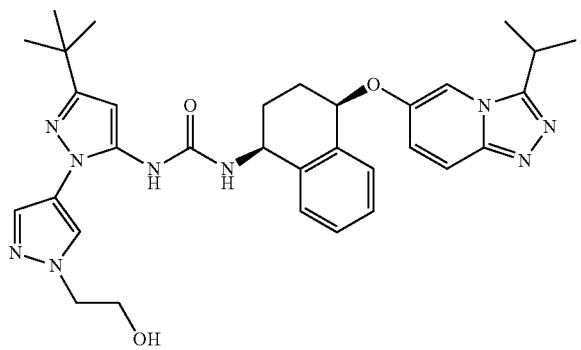 [SMILES: CC(C)c1nnc2ccc(O[C@@H]3CC[C@H](NC(=O)Nc4cc(C(C)(C)C)nn4-c4cnn(CCO)c4)c4ccccc43)cn12]

A mixture of Intermediate 6 (0.80 g, 1.88 mmol), Intermediate 18c (0.61 g, 1.89 mmol) and DIPEA (0.49 mL, 2.81 mmol) in dioxane (10 mL) was stirred at 70° C. for 18 h. The volatiles were concentrated in vacuo and the resultant residue was purified by FCC, using 50% DCM in cyclohexane then eluting with 0-10% [2M NH$_3$ in MeOH] in DCM, to afford the title compound (0.97 g, 85%). LCMS (Method 3): Rt 3.12 min, m/z 598 [MH$^+$].

e. Methanesulfonic acid 2-(3-tert-butyl-5-{3-[(1S,4R)-4-(3-isopropyl-[1,2,4]triazolo[4,3-a]pyridin-6-yloxy)-1,2,3,4-tetrahydro-naphthalen-1-yl]-ureido}-[1,4']bipyrazolyl-1'-yl)-ethyl ester. (Intermediate 18e)

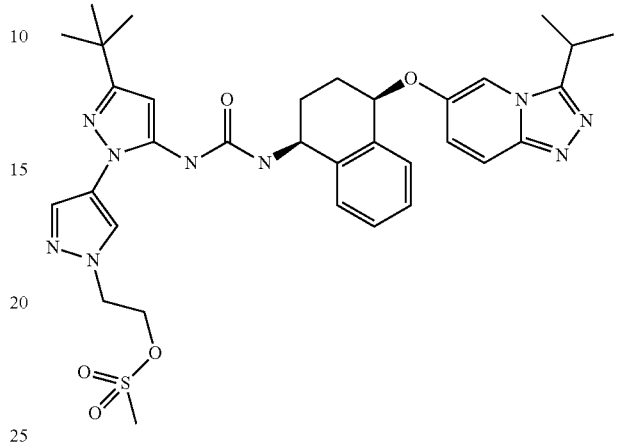

A mixture of Intermediate 18d (0.30 g, 0.50 mmol), methanesulfonyl chloride (58.0 µL, 0.75 mmol) and DIPEA (260 µL, 1.49 mmol) in DCM (8 mL) was stirred at RT for 1 h. The reaction mixture was partitioned between DCM and water. The organic layer was washed with brine, passed through a phase separating cartridge and concentrated in vacuo to afford the title compound (0.34 g, 100%). LCMS (Method 3): Rt 3.35 min, m/z 676 [MH$^+$].

f. [3-tert-Butyl-1'-(2-dimethylamino-ethyl)-1'H-[1,4']bipyrazolyl-5yl]-3[(1S,4R)-4-(3-isopropyl-[1,2,4]triazolo[4,3-a]pyridin-6-yloxy) 1,2,3,4-tetrahydro-naphthalen-1-yl]-urea (Example 18)

A mixture of Intermediate 18e (0.34 g, 0.50 mmol) and dimethylamine (2.0M in THF, 5.0 mL, 10.0 mmol) was stirred at 60° C. for 18 h in a sealed vial. The volatiles were concentrated in vacuo and the resultant residue was purified by FCC, using 0-10% [2M NH$_3$ in MeOH] in DCM. The isolated product was further purified by HPLC (Gemini C18, 20-60% MeCN in H$_2$O, 0.1% HCO$_2$H) and freeze dried to afford the title compound (90 mg, 29%). LCMS (Method 5): Rt 3.20 min, m/z 625.4 [MH$^+$]. $^1$H NMR (400 MHz, d$_6$-DMSO): 1.24 (9H, s), 1.36-1.41 (6H, m), 1.83-2.02 (2H, m), 2.07-2.14 (2H, m), 2.17 (6H, s), 2.67 (2H, t, J=6.6 Hz), 3.57 (1H, septet, J=6.8 Hz), 4.20 (2H, t, J=6.6 Hz), 4.81-4.89 (1H, m), 5.55 (1H, t, J=4.8 Hz), 6.27 (1H, s), 7.14-7.19 (2H, m), 7.26-7.42 (4H, m), 7.62 (1H, s), 7.69 (1H, d, J=9.9 Hz), 8.00 (1H, s), 8.04 (1H, s), 8.18 (0.5H, s), 8.21 (1H, s).

Examples 19-24 a. General Displacement Procedure

A mixture of Intermediate A-E (0.115 mmol) and an appropriate amine [see table 2] (2.30 mmol) in anhydrous THF (1 mL) was stirred at 60° C. for 18 h in a sealed vial. The volatiles were concentrated in vacuo and the resulting residue was purified by either by MDAP (method 7) or HPLC (Gemini C18, 20-40% MeCN in H$_2$O, 0.1% HCO$_2$H, 18 ml/min.) or both to afford the title compound (40-80%).

| Example No. | Amine | Interm. Used | Example Structure | NMR (400 MHz) δ | LCMS |
|---|---|---|---|---|---|
| 19 | <br>Pyrrolidine | D | 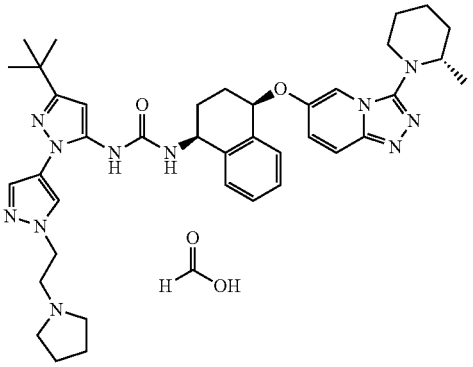 [SMILES: C[C@H]1CCCCN1c1nnc2ccc(O[C@@H]3CC[C@H](NC(=O)Nc4cc(C(C)(C)C)nn4-c4cnn(CCN5CCCC5)c4)c4ccccc43)cn12 ; O=CO]<br>1-[3-tert-Butyl-1'-(2-pyrrolidin-1-yl-ethyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J = 6.2 Hz), 1.25 (9H, s), 1.45-1.57 (2H, m), 1.61-1.73 (6H, m), 1.75-2.18 (6H, m), ~2.48 (4H, m, obscured by solvent), 2.87 (2H, t, J = 6.6 Hz), 2.89-2.95 (1H, m), 3.12-3.20 (1H, m, obscured by water), 3.27-3.36 (1H, m, obscured by water), 4.23 (2H, t, J = 6.6 Hz), 4.80-4.88 (1H, m), 5.53 (1H, t, J = 4.5 Hz), 6.27 (1H, s), 7.16 (1H, d, J = 8.6 Hz), 7.20 (1H, dd, J = 9.9, 2.1 Hz), 7.25-7.32 (1H, m), 7.32-7.40 (3H, m), 7.62-7.66 (2H, m), 7.70 (1H, d, J = 1.9 Hz), 8.01 (1H, s), 8.06 (1H, s), 8.16 (1.2H, s). | (Method 5): Rt 3.55 min, m/z 706.4 [MH$^+$]. |
| 20 | 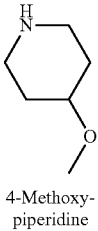<br>4-Methoxy-piperidine | D | 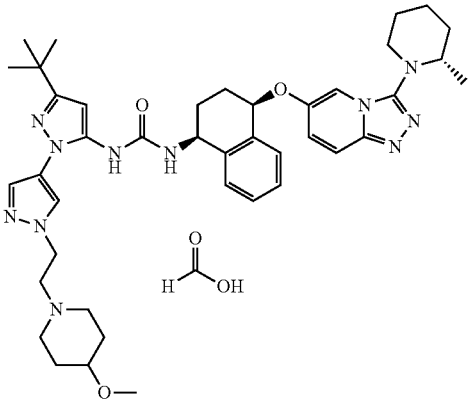<br>1-{3-tert-Butyl-1'-[2-(4-methoxy-piperidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J = 6.4 Hz), 1.25 (9H, s), 1.32-1.44 (2H, m), 1.45-1.57 (2H, m), 1.61-2.19 (12H, m), 2.65-2.75 (2H, m), 2.71 (2H, t, J = 6.7 Hz), 2.86-2.95 (1H, m), 3.09-3.18 (2H, m, obscured by water), 3.19 (3H, s), ~3.32 (1H, m, completely obscured by water), 4.22 (2H, t, J = 6.7 Hz), 4.79-4.88 (1H, m), 5.53 (1H, t, J = 4.4 Hz), 6.26 (1H, s), 7.14 (1H, d, J = 8.8 Hz), 7.20 (1H, dd, J = 10.0, 2.0 Hz), 7.25-7.32 (1H, m), 7.32-7.41 (3H, m), 7.62-7.67 (2H, m), 7.70 (1H, d, J = 1.8 Hz), 8.00 (1H, s), 8.04 (1H, s), 8.15 (1.3H, s). | (Method 5): Rt 3.60 min, m/z 750.5 [MH$^+$]. |
| 21 | 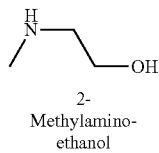<br>2-Methylamino-ethanol | D | 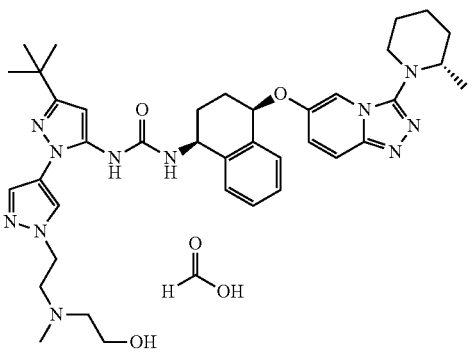 [SMILES: C[C@H]1CCCCN1c1nnc2ccc(O[C@@H]3CC[C@H](NC(=O)Nc4cc(C(C)(C)C)nn4-c4cnn(CCN(C)CCO)c4)c4ccccc43)cn12 ; O=CO]<br>1-(3-tert-Butyl-1'-{2-[(2-hydroxy-ethyl)-methyl-amino]-ethyl}-1'H-[1,4']bipyrazolyl-5-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J = 6.2 Hz), 1.25 (9H, s), 1.44-1.57 (2H, m), 1.60-1.73 (2H, m), 1.73-2.19 (6H, m), 2.23 (3H, s), 2.46 (2H, t, J = 6.2 Hz), 2.81 (2H, t, J = 6.6 Hz), 2.86-2.95 (1H, m), 3.12-3.20 (1H, m, obscured by water), ~3.32 (1H, m, completely obscured by water), 3.44 (2H, t J = 6.2 Hz, obscured by water), 4.20 (2H, t, J = 6.6 Hz), 4.80-4.89 (1H, m), 5.53 (1H, t, J = 4.5 Hz), 6.27 (1H, s), 7.15 (1H, d, J = 8.4 Hz), 7.20 (1H, dd, J = 9.8, 2.2 Hz), 7.25-7.32 (1H, m), 7.32-7.40 (3H, m), 7.61-7.66 (2H, m), 7.70 (1H, d, J = 1.7 Hz), 7.99 (1H, s), 8.07 (1H, s), 8.16 (1H, s). | (Method 5): Rt 3.49 min, m/z 710.5 [MH$^+$]. |

| Example No. | Amine | Interm. Used | Example Structure | NMR (400 MHz) δ | LCMS |
|---|---|---|---|---|---|
| 22 | <br>(S)-Pyrrolidin-3-ol | D | 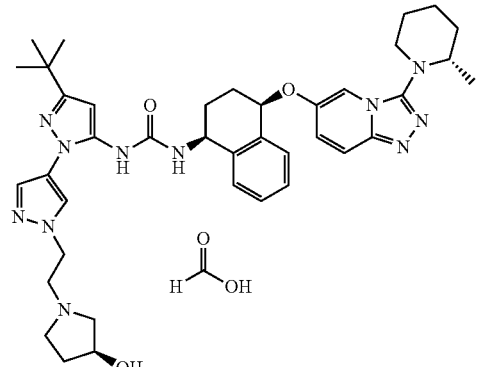<br>1-{3-tert-Butyl-1'-[2-((S)-3-hydroxy-pyrrolidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J = 6.3 Hz), 1.25 (9H, s), 1.44-1.57 (3H, m), 1.61-2.18 (9H, m), 2.34 (1H, dd, J = 9.5, 3.6 Hz), 2.44-2.50 (1H, m, obscured by solvent), 2.56-2.64 (1H, m), 2.75 (1H, dd, J = 9.5, 2.8 Hz), 2.84 (2H, t, J = 6.7 Hz), 2.87-2.95 (1H, m), 3.12-3.20 (1H, m, obscured by water), ~3.32 (1H, completely obscured by water), 4.12-4.18 (1H, m), 4.21 (2H, t, J = 6.6 Hz), 4.80-4.88 (1H, m), 5.53 (1H, t, J = 4.4 Hz), 6.27 (1H, m), 7.16 (1H, d, J = 8.6 Hz), 7.20 (1H, dd, J = 10.0, 2.1 Hz), 7.25-7.31 (1H, m), 7.32-7.40 (3H, m), 7.62-7.66 (2H, m), 7.70 (1H, d, J = 2.0 Hz), 8.01 (1H, s), 8.06 (1H, s), 8.18 (1H, s). | (Method 5): Rt 3.48 min, m/z 722.5 [MH$^+$]. |
| 23 | 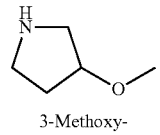<br>3-Methoxy-pyrrolidine | D | 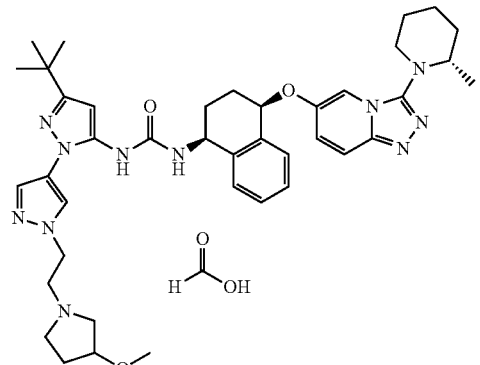<br>1-{3-tert-Butyl-1'-[2-(3-methoxy-pyrrolidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | | (Method 5): Rt 3.58 min, m/z 736.4 [MH$^+$]. |
| 24 | 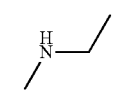<br>Ethyl-methyl-amine | D | 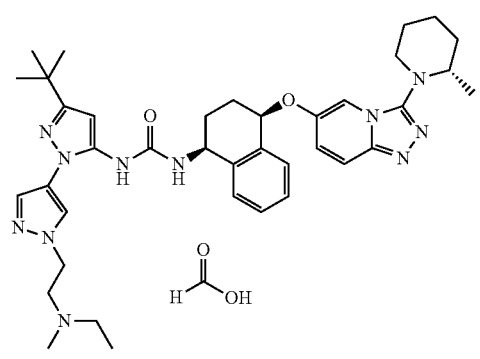 [SMILES: CCN(C)CCn1cc(-n2nc(C(C)(C)C)cc2NC(=O)N[C@H]2CC[C@@H](Oc3ccc4nnc(N5CCCC[C@@H]5C)n4c3)c3ccccc32)cn1 ; O=CO]<br>1-{3-tert-Butyl-1'-[2-(ethyl-methyl-amino)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | | (Method 5): Rt 3.55 min, m/z 694.4 [MH$^+$]. |

| Example No. | Amine | Interm. Used | Example Structure | NMR (400 MHz) δ | LCMS |
|---|---|---|---|---|---|
| 25 | (S)-1-Pyrrolidin-2-yl-methanol | D | 1-{3-tert-Butyl-1'-[2-((S)-2-hydroxymethyl-pyrrolidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J = 6.2 Hz), 1.25 (9H, s), 1.39-2.18 (16H, m), 2.18-2.26 (1H, m), 2.67-2.75 (1H, m), 2.86-2.95 (1H, m), 2.99-3.05 (1H, m), 3.12-3.37 (4H, m, obscured by water), 4.20 (2H, t, J = 6.8 Hz), 4.36 (1H, br, s), 4.80-4.88 (1H, m), 5.53 (1H, t, J = 4.4 Hz), 6.26 (1H, s), 7.14-7.22 (2H, m), 7.25-7.32 (1H, m), 7.32-7.40 (3H, m), 7.61-7.66 (2H, m), 7.70 (1H, d, J = 1.7 Hz), 8.01 (1H, s), 8.07 (1H, s), 8.27 (0.3H, s). | (Method 5): Rt 3.56 min, m/z 736.6 [MH$^+$]. |
| 26 | (1S,4S)-2-Methyl-2,5-diaza-bicyclo[2.2.1]-heptane | D | 1-{3-tert-Butyl-1'-[2-((1S,4S)-5-methyl-2,5-diaza-bicyclo[2.2.1]hept-2-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt | $^1$H NMR (400 MHz, d$_6$-DMSO): 0.91 (3H, d, J = 6.1 Hz), 1.25 (9H, s), 1.45-2.18 (12H, m), 2.28 (3H, s), ~2.52 (1H, m, obscured by solvent), 2.63 (2H, s), 2.68-2.73 (1H, m), 2.80-2.97 (3H, m), 3.13-3.22 (2H, m, obscured by water), 3.25-3.34 (2H, m, obscured by water), 4.14 (2H, t, J = 6.6 Hz), 4.80-4.88 (1H, m), 5.53 (1H, t, J = 4.4 Hz), 6.26 (1H, s), 7.16-7.22 (2H, m), 7.25-7.31 (1H, m), 7.32-7.40 (3H, m), 7.61-7.66 (2H, m), 7.70 (1H, d, J = 1.9 Hz), 8.04-8.07 (2H, m), 8.26 (0.9H, s). | (Method 5): Rt 3.48 min, m/z 47.5 [MH$^+$]. |

Example 27

1-[3-tert-Butyl-1'-(2-dimethylamino-ethyl)-1'H-[1,4']bipyrazolyl-5-yl]-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea a. 6-Fluoro-[1,2,4]triazolo[4,3-a]pyridine (Intermediate 27a)

(5-Fluoro-pyridin-2-yl)-hydrazine (500 mg, 3.93 mmol) in diethoxymethyl acetate (5 mL) was stirred at RT for 2 h. The resulting precipitate was diluted with cyclohexane (5 ml) and filtered to give the title compound (379 mg, 70%). $^1$H NMR (400 MHz, CDCl$_3$): 7.25 (1H, m), 7.84 (1H, m), 8.09 (1H, t), 8.84 (1H, s).

b. 3-Chloro-6-fluoro-[1,2,4]triazolo[4,3-a]pyridine (Intermediate 27b)

A solution of Intermediate 27a (789 mg, 5.98 mmol) and N-chlorosuccinimide (878 mg, 6.57 mmol) in chloroform (15 mL) was heated at 65° C. overnight. The cooled mixture was washed with sat. aq. NaHCO₃ solution (2×15 mL) and dried (Na₂SO₄). The solvent was evaporated, then the residue suspended in diethyl ether (10 mL) and filtered to give the title compound (730 mg, 76%). LCMS (Method 1): Rt 1.83 min, m/z 172 [MH⁺].

c. [(S)-1-(6-Fluoro-[1,2,4]triazolo[4,3-a]pyridin-3-yl)-pyrrolidin-2-yl]-methanol (Intermediate 27c)

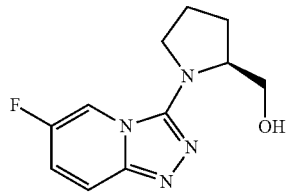 [SMILES: OC[C@@H]1CCCN1c1nnc2ccc(F)cn12]

A mixture of Intermediate 27b (300 mg, 1.74 mmol) and L-prolinol (704 mg, 9.96 mmol) in NMP (4 mL) was heated in the microwave at 160° C. for 2 h. The reaction mixture was applied to an SCX-2 cartridge (70 g) and washed with MeOH. The product was eluted with 2M NH₃ in MeOH; concentration in vacuo gave a residue. FCC, using 0-10% [2M NH₃ in MeOH] in DCM, gave the title compound (210 mg, 50%). LCMS (Method 4): Rt 1.50 min, m/z 237 [MH⁺].

d. 6-Fluoro-3-((S)-2-triisopropylsilanyloxymethyl-pyrrolidin-1-yl)-[1,2,4]triazolo[4,3-a]pyridine (Intermediate 27d)

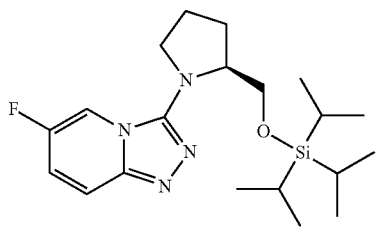 [SMILES: CC(C)[Si](OC[C@@H]1CCCN1c1nnc2ccc(F)cn12)(C(C)C)C(C)C]

Triisopropylsilyl trifluoromethanesulfonate (327 mg, 1.06 mmol) was added to a solution of Intermediate 27c (210 mg, 0.89 mmol) and Et₃N (135 mg, 1.33 mmol) in a DMF (3 mL) and the mixture stirred at RT for 1 h. The reaction mixture was applied to an SCX-2 cartridge (25 g) and washed with MeOH. The product was eluted with 2M NH₃ in MeOH; concentration in vacuo gave a residue. FCC, using 0-10% [2M NH₃ in MeOH] in DCM, gave the title compound (110 mg, 31%). LCMS (Method 1): Rt 4.45 min, m/z 393 [MH⁺].

e. (1S,4R)-4-[3-((S)-2-Triisopropylsilanyloxymethyl-pyrrolidin-1-yl)-[1,2,4]triazolo[4,3-a]pyridin-6-yloxy]-1,2,3,4-tetrahydro-naphthalen-1-ylamine (Intermediate 27e)

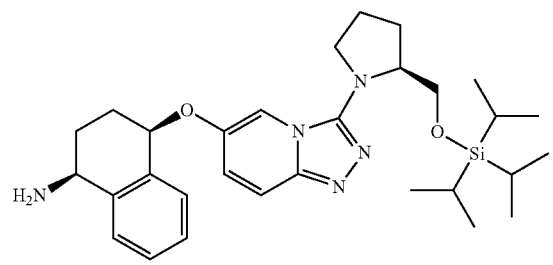 [SMILES: CC(C)[Si](OC[C@@H]1CCCN1c1nnc2ccc(O[C@@H]3CC[C@H](N)c4ccccc43)cn12)(C(C)C)C(C)C]

To a solution of Intermediate 1 (50 mg, 0.309 mmol) in DMF (2 mL) was added NaH (60% in oil, 33 mg, 0.80 mmol) and the mixture stirred at RT for 20 min, before Intermediate 27d (110 mg, 0.280 mmol) was added. This mixture was heated at 60° C. in the microwave for 1.25 h. The reaction mixture was applied to an SCX-2 cartridge (25 g) and washed with MeOH. The product was eluted with 2M NH₃ in MeOH; concentration in vacuo gave a residue. FCC, using 0-7% [2M NH₃ in MeOH] in DCM gave the title compound as a viscous yellow oil (42 mg, 28%). LCMS (Method 4): Rt 2.55 min, m/z 536 [MH⁺].

f. 1-[3-tert-Butyl-1'-(2-hydroxy-ethyl)-1'H-[1,4']bipyrazolyl-5-yl]-3-{(1S,4R)-4-[3-((S)-2-triisopropylsilanyloxymethyl-pyrrolidin-1-yl)-[1,2,4]triazolo[4,3-a]pyridin-6-yloxy]-1,2,3,4-tetrahydro-naphthalen-1-yl}-urea (Intermediate 27f)

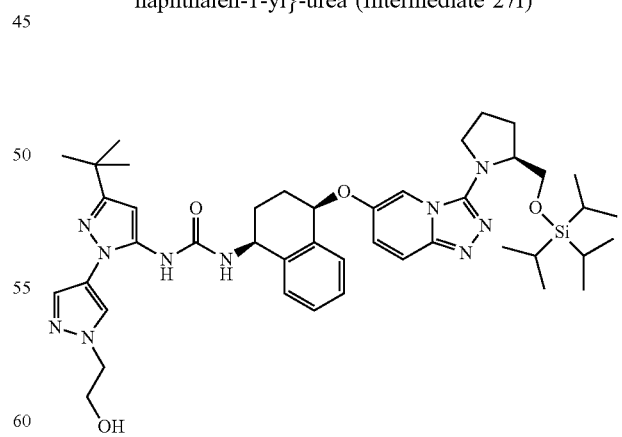

The title compound was prepared starting from Intermediate 6 and Intermediate 27e by using an analogous procedure to that described for Example 18 step d. LCMS (Method 3): Rt 4.19 min, m/z 811.6 [MH⁺].

g. Methanesulfonic acid 2-[3-tert-butyl-5-(3-{(1S,4R)-4-[3-((S)-2-triisopropylsilanyloxymethyl-pyrrolidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester (Intermediate 27 g)

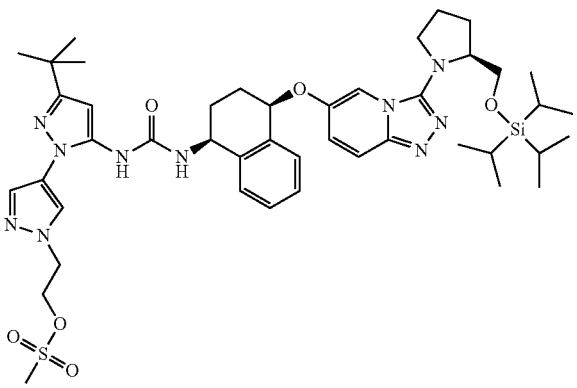 [SMILES: CC(C)[Si](OC[C@@H]1CCCN1c1nnc2ccc(O[C@@H]3CC[C@H](NC(=O)Nc4cc(C(C)(C)C)nn4-c4cnn(CCOS(C)(=O)=O)c4)c4ccccc43)cn12)(C(C)C)C(C)C]

The title compound was prepared starting from Intermediate 27f by using an analogous procedure to that described for Example 18 step e. LCMS (Method 3): Rt 4.37 min, m/z 889.5 [MH+].

h. 1-[3-tert-Butyl-1'-(2-dimethylamino-ethyl)-1'H-[1,4']bipyrazolyl-5-yl]-3-{(1S,4R)-4-[3-((S)-2-triisopropylsilanyloxymethyl-pyrrolidin-1-yl)-[1,2,4]triazolo[4,3-a]pyridin-6-yloxy]-1,2,3,4-tetrahydro-naphthalen-1-yl}-urea (Intermediate 27 h)

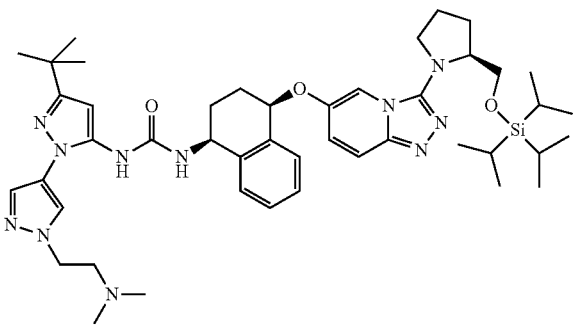 [SMILES: CC(C)[Si](OC[C@@H]1CCCN1c1nnc2ccc(O[C@@H]3CC[C@H](NC(=O)Nc4cc(C(C)(C)C)nn4-c4cnn(CCN(C)C)c4)c4ccccc43)cn12)(C(C)C)C(C)C]

The title compound was prepared starting from Intermediate 27 g by using an analogous procedure to that described for Example 18 step f. LCMS (Method 3): Rt 3.28 min, m/z 838.6 [MH+].

i. 1-[3-tert-Butyl-1'-(2-dimethylamino-ethyl)-1'H-[1,4']bipyrazolyl-5-yl]-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea (Example 27)

To a solution of Intermediate 27 h (139 mg, 0.166 mmol) in 2-methylTHF (3 mL) was added a solution of TBAF in THF (1M, 0.21 mL, 0.21 mmol). Stirred at RT for 1 h then diluted with water and extracted with DCM (4×20 mL). The combined organic phases were passed through a phase separator tube then evaporated to dryness. The residue was purified by FCC, eluting with 0-16% 2M NH$_3$/MeOH in DCM, to give a pale yellow glass. This was dissolved in acetonitrile/water and freeze-dried to give the title compound as a pale cream solid (90 mg, 80%). LCMS (Method 5): Rt 2.93 min, m/z 682.4 [MH+]. $^1$H NMR (400 MHz, d$_6$-DMSO): 1.25 (9H, s), 1.72-2.13 (8H, m), 2.17 (6H, s), 2.67 (2H, t, J 6.5), 3.31-3.39 (2H, m), 3.41-3.48 (1H, m), 3.69 (1H, dt, J 9.5, 6.9), 4.02-4.10 (1H, m), 4.20 (2H, t, J 6.6), 4.77-4.87 (2H, m), 5.46 (1H, t, J 4.5), 6.27 (1H, s), 7.06 (1H, dd, J 9.9, 2.0), 7.15 (1H, d, J 8.5), 7.27-7.43 (4H, m), 7.54 (1H, d, J 9.9), 7.63 (1H, s), 7.98 (1H, br s), 8.03-8.06 (2H, m).

Example 28

1-[3-tert-Butyl-1'-(2-hydroxy-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt

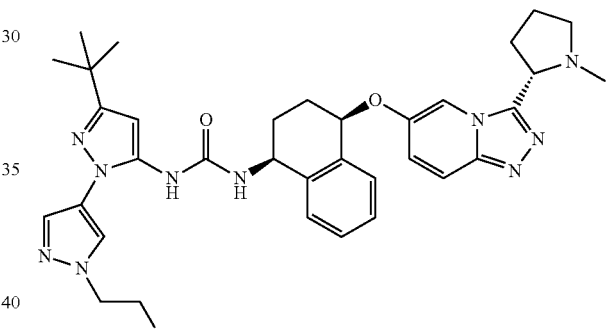

a. (S)-1-Methyl-pyrrolidine-2-carboxylic acid N'-(5-fluoro-pyridin-2-yl)-hydrazide (Intermediate 28a)

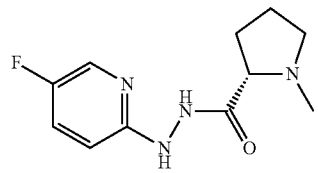 [SMILES: CN1CCC[C@H]1C(=O)NNc1ccc(F)cn1]

EDC (271 mg, 1.41 mmol) was added portionwise to a solution of 5-fluoro-2-hydrazinyl-pyridine (for reference procedure see WO2010022076; 0.15 g, 1.18 mmol), N-methyl-L-proline monohydrate (0.20 g, 1.36 mmol) and HOBt (16 mg, 0.12 mmol) in dry DCM (5 mL) at RT and stirred for 16 h. The solution was diluted with DCM (15 mL), washed with water (150 mL), dried (Na$_2$SO$_4$) and evaporated to give the title compound as a pale yellow gum (189 mg, 67%). LCMS (Method 1): Rt 0.31 min, m/z 239 [MH+].

b. 6-Fluoro-3-((S)-1-methyl-pyrrolidin-2-yl)-[1,2,4]triazolo[4,3-a]pyridine (Intermediate 28b)

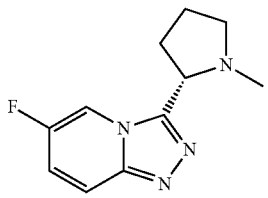 [SMILES: CN1CCC[C@H]1c1nnc2ccc(F)cn12]

Hexachloroethane (375 mg, 1.59 mmol) was added portionwise to a solution of Intermediate 28a (189 mg, 0.79 mmol), triphenylphosphine (416 mg, 1.59 mmol) and triethylamine (0.44 mL, 3.17 mmol) in dry THF (10 mL) at RT and stirred for 4 h. The resulting precipitate was filtered off and the filtrate evaporated. The residue was purified by SCX-2, eluting with MeOH followed by 2M NH$_3$ in MeOH gave the title compound as a brown foam (136 mg, 78%). LCMS (Method 1): Rt 0.45 min, m/z 221 [MH$^+$].

c. (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine. (Intermediate 28c)

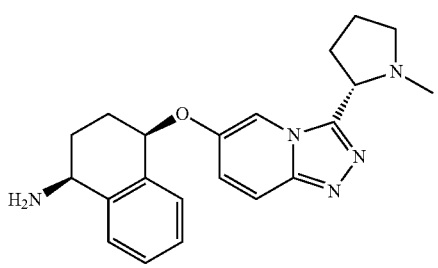 [SMILES: CN1CCC[C@H]1c1nnc2ccc(O[C@@H]3CC[C@H](N)c4ccccc43)cn12]

Intermediate 1 (128 mg, 0.77 mmol) was added portionwise to a suspension of sodium hydride (60% in mineral oil, 92 mg, 2.30 mmol) in dry DMF (3 mL) at RT and stirred for 15 mins. Intermediate 28b (169 mg, 0.77 mmol) was then added in one portion and the mixture heated at 60° C. for 4 h. After cooling, saturated NH$_4$Cl (ca. 0.2 mL) was added. The mixture was partitioned between water (10 mL) and ethyl acetate (3×10 mL). The aqueous phase was concentrated in vacuo and the residue purified by SCX-2, eluting with MeOH followed by 2M NH$_3$ in MeOH, to give the title compound as brown coloured foam (103 mg, 36%). LCMS (Method 1): Rt 1.34 min, m/z 364 [MH$^+$].

d. 1-[3-tert-Butyl-1'-(2-hydroxy-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt (Example 28)

A mixture of Intermediate 6 (0.23 g, 0.54 mmol), Intermediate 28c (0.195 g, 0.54 mmol) and DIPEA (0.18 mL, 1.03 mmol) in dioxane (5 mL) was stirred at 70° C. for 18 h. The volatiles were concentrated in vacuo and the resultant residue redissolved in DCM (50 mL), washed with water and brine then dried and evaporated to give a brown residue. This was purified by FCC using 0-10% [2M NH$_3$ in MeOH] in DCM followed by MDAP to afford the title compound (96 mg, 26%) as a glass. LCMS (Method 5): Rt 2.99 min, m/z 639.4 [MH$^+$]. $^1$H NMR (400 MHz, DMSO): 1.25 (9H, s), 1.83-2.25 (9H, m), 2.13 (3H, s), 2.35-2.39 (1H, m), 3.11-3.17 (1H, m), 3.77 (2H, t, J 5.7 Hz), 3.99 (1H, t, J 8.1 Hz), 4.17 (2H, t, J 5.7 Hz), 4.81-4.89 (1H, m), 5.40 (1H, t, J 4.4 Hz), 6.27 (1H, s), 7.18 (1H, d, J 8.5 Hz), 7.25-7.39 (5H, m), 7.64 (1H, d, J 0.7 Hz), 7.79 (1H, d, J 9.7 Hz), 8.00 (1H, s), 8.01 (1H, d, J 0.6 Hz), 8.15 (1H, s), 8.24-8.26 (1H, m).

Example 29

1-[3-tert-Butyl-1'-(2-dimethylamino-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt

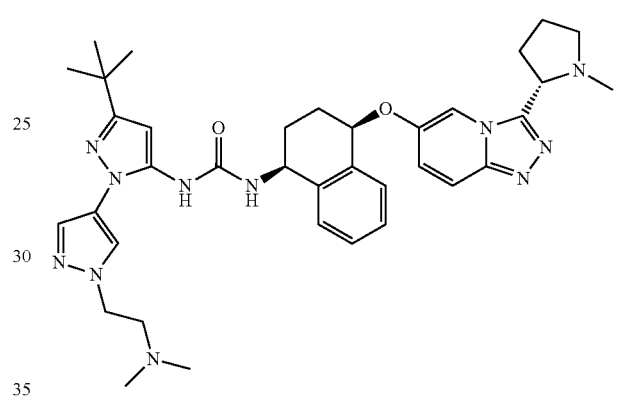

a. Methanesulfonic acid 2-[3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester (Intermediate 29a)

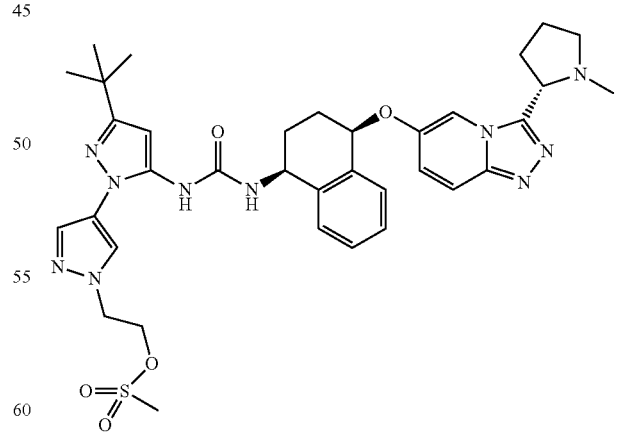

A mixture of Example 28 (0.140 g, 0.219 mmol), methanesulfonyl chloride (26 µL, 0.336 mmol) and DIPEA (115 µL, 0.660 mmol) in DCM (1 mL) was stirred at RT for 1 hour. The reaction mixture was partitioned between DCM and water. The organic layer was washed with brine, separated through a phase separating cartridge and concentrated in vacuo to afford the title compound (0.17 g, 100%) as a pale yellow solid. LCMS (Method 3): Rt 2.65 min, m/z 717 [MH+].

b. 1-[3-tert-Butyl-1'-(2-dimethylamino-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt (Example 29)

A mixture of Intermediate 29a (0.17 g, 0.22 mmol) and dimethylamine (2.0M in THF, 1.2 mL, 2.4 mmol) was stirred at r.t. for 18 h in a sealed vial.

The volatiles were concentrated in vacuo and the resultant residue was purified by MDAP to afford the title compound (93 mg, 57%). LCMS (Method 5): Rt 2.57 min, m/z 666.4 [MH+]. $^1$H NMR (400 MHz, DMSO): 1.25 (9H, s), 1.83-2.25 (8H, m), 2.13 (3H, s), 2.19 (6H, s), 2.31-2.39 (1H, m), 2.70 (2H, t, J 6.5 Hz), 3.11-3.17 (1H, m), 4.00 (1H, t, J 8.1 Hz), 4.21 (2H, t, J 6.5 Hz), 4.81-4.89 (1H, m), 5.41 (1H, t, J 4.4 Hz), 6.27 (1H, s), 7.16 (1H, t, J 8.6 Hz), 7.25-7.39 (5H, m), 7.63 (1H, d, J 0.6 Hz)), 7.75 (1H, dd, J 10.0, 0.5 Hz), 7.99 (1H, s), 8.05 (1H, d, J 0.6 Hz), 8.14 (1.6H, s), 8.24-8.26 (1H, m).

Example 30

1-{5-tert-Butyl-2-[6-(2-dimethylamino-ethoxy)-pyridazin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

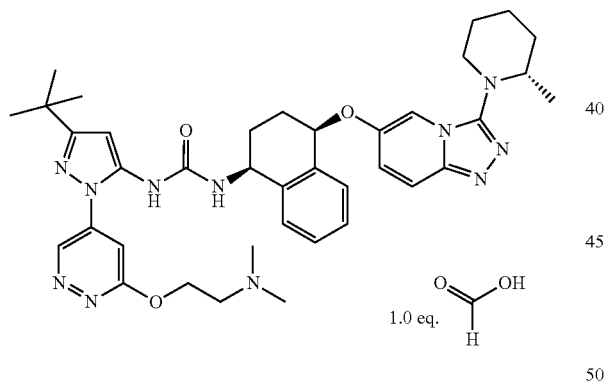

a. 5-Iodo-3-[2-(tetrahydro-pyran-2-yloxy)-ethoxy]-pyridazine (Intermediate 30a)

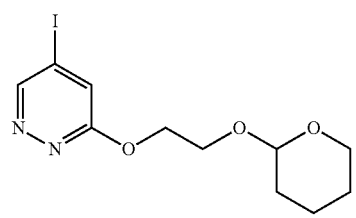 [SMILES: Ic1cnnc(OCCOC2CCCCO2)c1]

To a solution of 5-iodo-3(2H)-pyridazinone (917 mg, 4.13 mmol), 2-(tetrahydro-2H-pyran-2-yloxy)ethanol (755 mg, 701 μL, 5.16 mmol) and triphenylphosphine (1.63 g, 6.20 mmol), in THF at 3° C. was added diethyl azodicarboxylate (1.08 g, 976 μL, 6.20 mmol) dropwise over 10 min, ensuring the temperature did not exceed 10° C. After 15 min, the reaction mixture was concentrated in vacuo and subjected to FCC eluting with 5-40% EtOAc/cyclohexane to afford the title compound as an off-white solid (1.35 g, 93%). LCMS (Method 4): Rt 3.15 min, m/z 373 [M+Na+].

b. 2-(5-Iodo-pyridazin-3-yloxy)-ethanol (Intermediate 30b)

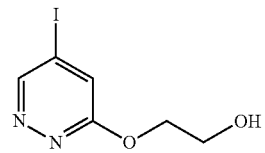 [SMILES: OCCOc1cc(I)cnn1]

To a solution of Intermediate 30a (1.25 g, 3.57 mmol) in MeOH (25 mL) was added pyridinium p-toluenesulfonate (2.69 g, 10.7 mmol) and the reaction was heated to 40° C. After 1 h, the reaction mixture was concentrated in vacuo, dissolved in water (20 mL) and saturated NaHCO$_3$ solution (20 mL), and extracted with DCM (3×20 mL). The combined organics were passed through a phase separator cartridge and concentrated in vacuo to afford a pale yellow solid. Residual pyridine was then removed by azeotrope with toluene to afford the title compound as an off-white solid (815 mg, 86%). LCMS (Method 4): Rt 1.99 min, m/z 267 [MH+].

c. 2-[5-(5-Amino-3-tert-butyl-pyrazol-1-yl)-pyridazin-3-yloxy]-ethanol (Intermediate 30c)

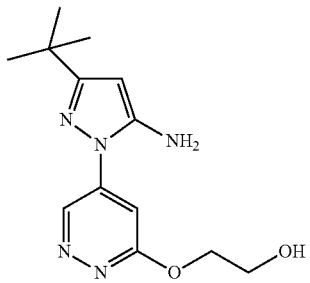 [SMILES: CC(C)(C)c1cc(N)n(-c2cnnc(OCCO)c2)n1]

3-(tert-butyl)-1H-pyrazole-5-amine (503 mg, 3.61 mmol), Intermediate 30b (915 mg, 3.44 mmol), copper (I) iodide (32.8 mg, 0.172 mmol), trans-N,N'-dimethylcyclohexane-1,2-diamine (97.8 mg, 0.688 mmol) and K$_2$CO$_3$ (998 mg, 7.22 mmol) were weighed in a round bottom flask, sealed with a septum and evacuated and purged with Ar 3 times. Xylene (4 ml, sparged with Ar for 45 min), was then introduced to the flask and the brown suspension was heated to 150° C. for 90 min. The reaction was cooled, diluted with EtOAc (10 mL), water (10 mL) and saturated aqueous NH$_4$OH solution (5 mL). The aqueous layer was extracted with EtOAc (2×10 mL), and the combined organics washed with brine (15 mL), dried over Na$_2$SO$_4$, filtered, concentrated in vacuo and subjected to FCC eluting with 0-4% MeOH/EtOAc to afford the title compound as a pale yellow solid (457 mg, 48%). LCMS (Method 4): Rt 2.81 min, m/z 278 [MH+].

d. {5-tert-Butyl-2-[6-(2-hydroxy-ethoxy)-pyridazin-4-yl]-2H-pyrazol-3-yl}-carbamic acid 2,2,2-trichloro-ethyl ester (Intermediate 30d)

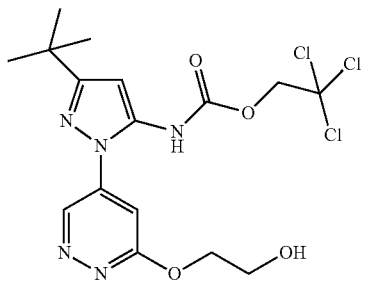 [SMILES: CC(C)(C)c1cc(NC(=O)OCC(Cl)(Cl)Cl)n(-c2cnnc(OCCO)c2)n1]

To an ice-cooled, stirred solution of Intermediate 30c (382 mg, 1.38 mmol) in 1M aqueous NaOH solution (3.4 mL, 3.4 mmol) and EtOAc (5 mL) was added dropwise 2,2,2-trichloroethyl chloroformate (321 mg, 209 µL, 1.52 mmol) and the ice bath removed. After 2 h, a further 1.1 eq. of 2,2,2-trichloroethyl chloroformate was added. After another 2 h, another 1.1 eq. of 2,2,2-trichloroethyl chloroformate was added and the reaction stirred overnight. The reaction was then partitioned between H2O and EtOAc; the organic layer was separated, and the aqueous layer extracted again with EtOAc. The combined organics were dried over MgSO$_4$ concentrated in vacuo and subjected to FCC, eluting with 20-60% EtOAc/cyclohexane to afford the title compound as a yellow foam (476 mg, 76%). LCMS (Method 4): Rt 3.70 min, m/z 452,454 [MH$^+$].

e. 1-{5-tert-Butyl-2-[6-(2-hydroxy-ethoxy)-pyridazin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 30e)

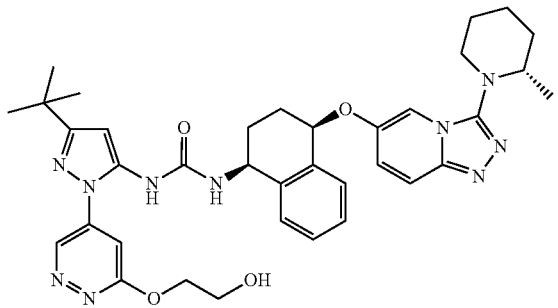 [SMILES: C[C@H]1CCCCN1c1nnc2ccc(O[C@@H]3CC[C@H](NC(=O)Nc4cc(C(C)(C)C)nn4-c4cnnc(OCCO)c4)c4ccccc43)cn12]

A solution of Intermediate 30d (476 mg, 1.05 mmol), Intermediate 2 (397 mg, 1.05 mmol) and DIPEA (204 mg, 269 µL, 1.58 mmol) in 2-methyltetrahydrofuran was heated to 60° C. overnight. The reaction mixture was cooled, concentrated in vacuo, and partitioned between H$_2$O and DCM. The mixture was passed through a phase separator cartridge, and the organic layer concentrated in vacuo and triturated with Et$_2$O to afford the title compound as a light brown solid (703 mg, 98%). LCMS (Method 4): Rt 3.40 min, m/z 681.4 [MH$^+$].

f. Methanesulfonic acid 2-{5-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-pyridazin-3-yloxy}-ethyl ester (Intermediate 30f)

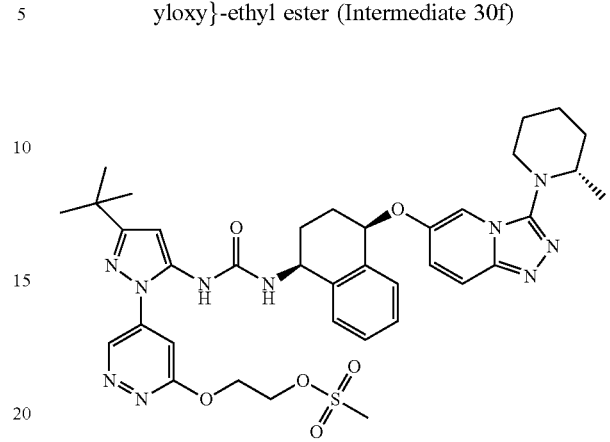

To a solution of Intermediate 30e (125 mg, 0.18 mmol) and DIPEA (71 mg, 94 µL, 0.24 mmol) in DCM (6 mL) was added methanesulfonyl chloride (27 mg, 19 µL, 0.24 mmol) and the reaction stirred at RT. After 30 min a further 0.65 eq. of methanesulfonyl chloride was added; after an additional 20 min the reaction was partitioned between H$_2$O and DCM, stirred vigorously and passed through a phase separator cartridge. The organic layer was concentrated in vacuo to afford the title compound as a yellow foam (139 mg, 100%). Rt 3.88 min, m/z 759.4 [MH$^+$].

g. 1-{5-tert-Butyl-2-[6-(2-dimethylamino-ethoxy)-pyridazin-4-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 30)

Intermediate 30f (139 mg, 0.18 mmol) was dissolved in dimethylamine solution (2 M in THF, 3 ml) in a capped microwave vial and stirred at RT for 72 h. The reaction was concentrated in vacuo, and subjected to FCC, eluting with 1-7% 2 M NH$_3$ in MeOH/DCM and concentrated in vacuo to afford a brown glass. This was further purified by HPLC (Gemini C18 column, 10-98% MeCN in H$_2$O, 0.1% formic acid) to afford the title compound as a white solid after lyophilisation (32.8 mg, 25%). LCMS (Method 5): Rt 3.55 min, m/z 708.5 [MH$^+$]. $^1$H NMR (400 MHz, d$_6$-DMSO): 0.91 (3H, d, J=6.0 Hz), 1.28 (9H, s), 1.45-1.58 (2H, m), 1.61-1.74 (2H, m), 1.74-1.87 (2H, m), 1.88-1.97 (2H, m), 1.98-2.10 (1H, m), 2.16 (6H, s), 2.19 (1H, m, obscured by singlet), 2.61 (2H, t, J=6.6 Hz), 2.86-2.95 (1H, m), 3.13-3.20 (2H, m), 4.17 (2H, t, J=6.5 Hz), 4.82 (1H, q, J=7.8 Hz), 5.52 (1H, t, J=4.1 Hz), 6.42 (1H, s), 7.00 (1H, d, J=2.2 Hz), 7.20 (1H, dd, J=2.1, 9.7 Hz), 7.26-7.31 (1H, m), 7.34-7.41 (4H, m), 7.64 (1H, d, J=10.0 Hz), 7.70 (1H, d, J=1.9 Hz), 8.18 (1H, s), 8.35 (1H, d, J=2.5 Hz), 8.51 (0.84H, br s).

Biological Assays

P38alpha Enzyme Inhibition Assay

The inhibitory activity of compounds was determined using an Alphascreen® (Perkin Elmer) based kinase activity assay. Kinase reactions consisted of 25 mM HEPES pH 7.5, 10 mM MgCl$_2$, 100 µM Na$_3$VO$_4$, 2 mM DTT, 0.05 mg/ml Tween 20, 100 pM p38alpha (Invitrogen, PV3304), 1% DMSO and 0.3 µg/ml ATF-2 fusion protein (New England Biolabs, 9224). Compounds were incubated under these conditions for 2 hours, at 25° C., prior to the initiation of the kinase activity by the addition of the 250 μM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. $IC_{50}$ values were determined from concentration-response curves.

All the compounds of the invention show a p38α binding potencies ($IC_{50}$ values) lower than 10 nM.

LPS-Stimulated PBMC TNFα Release Assay

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18 h. Cell-free supernatants were removed and assayed for TNFα levels using an ELISA kit from R&D Systems.

A dose response curve to each test compound was performed and the effect of compound in each experiment was expressed as a percentage inhibition of the control TNFα release. Dose response curves were plotted and compound potency ($IC_{50}$) was determined. Compounds were tested in at least three separate experiments.

All the compounds of the invention show p38α potencies ($IC_{50}$ values) lower than 10 nM.

The invention claimed is:
1. A compound selected from the group consisting of:
1-[3-tert-Butyl-1'-(2-[1,4]oxazepan-4-yl-ethyl)-1'H[1,4']bipyrazolyl-5-yl]-3-{(4-[3-2-methyl-piperidin-1-yl)-[1,2,4]triazolo[4,3-a]pyridin-6-yloxy]-1,2,3,4-tetrahydro-naphthalen-1-yl}-urea formate salt;
1-{3-tert-Butyl-1'-[2-(4-methyl-piperazin-1-yl)-ethyl]-1'H-[1,4']bipyrazolyl-5-yl}-3-{(4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;
1-{3-tert-Butyl-1'-[2-(4-hydroxy-piperidin-1-yl)-ethyl]-1'H-[1,4']bipyrazolyl-5-yl}-3-{4-[3-2-methyl-piperidin-1-yl)-[1,2,4]triazolo[4,3-a]pyridin-6-yloxy]-1,2,3,4-tetrahydro-naphthalen-1-yl}-urea formate salt;
1-(3-tert-Butyl-1'-{2-[(2-methoxy-ethyl)-methyl-amino]-ethyl}-1'H-[1,4']bipyrazolyl-5-yl)-3-4-[3-(-2-methyl-piperidin-1-yl)-[1,2,4]triazolo[4,3-a]pyridin-6-yloxy]-1,2,3,4-tetrahydro-naphthalen-1-yl}-urea;
1-[3-tert-Butyl-1'-(2-piperidin-1-yl-ethyl)-1'H-[1,4']bipyrazolyl-5-yl]-3-{4-[3-2,6-dimethyl-piperidin-1-yl)-[1,2,4]triazolo[4,3-a]pyridin-6-yloxy]-1,2,3,4-tetrahydro-naphthalen-1-yl}-urea formate salt;
1-[3-tert-Butyl-1'-(2-[1,4]oxazepan-4-yl-ethyl)-1'H-[1,4']bipyrazolyl-5-yl]-3-{4-[3-2,6-dimethyl-piperidin-1-yl)-[1,2,4]triazolo[4,3-a]pyridin-6-yloxy]-1,2,3,4-tetrahydro-naphthalen-1-yl}-urea formate salt;
1-[3-tert-Butyl-1'-(2-dimethylamino-ethyl)-1'H-[1,4']bipyrazolyl-5-yl]-3-[4-(3-dimethylamino-[1,2,4]triazolo[4,3-a]pyridin-6-yloxy)-1,2,3,4-tetrahydro-naphthalen-1-yl]-urea formate salt;
1-[3-tert-Butyl-1'-(2-dimethylamino-ethyl)-1'H[1,4']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-[3-tert-Butyl-1'-(3-dimethylamino-propyl)-1'H-[1,4']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-{3-tert-Butyl-1'-[3-(4-methyl-piperazin-1-yl)-propyl]-1'H-[1,4']bipyrazolyl-5-yl}-3-{4-[3-2-methyl-piperidin-1-yl)-[1,2,4]triazolo[4,3-a]pyridin-6-yloxy]-1,2,3,4-tetrahydro-naphthalen-1-yl}-urea formate salt;
1-[3-tert-Butyl-1'-(2-dimethylamino-ethyl)-1'H-[1,3']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-[3-tert-Butyl-1'-(2-dimethylamino-ethyl)-1'H-[1,3']bipyrazolyl-5-yl]-3-{4-[3-(2,6-dimethyl-piperidin-1-yl)-[1,2,4]triazolo[4,3-a]pyridin-6-yloxy]-1,2,3,4-tetrahydro-naphthalen-1-yl}-urea formate salt;
1-[5-tert-Butyl-2-(2-dimethylamino-ethyl)-2H-pyrazol-3-yl]-3-{4-[3-(2,6-dimethyl-piperidin-1-yl)-[1,2,4]triazolo[4,3-a]pyridin-6-yloxy]-1,2,3,4-tetrahydronaphthalen-1-yl}-urea formate salt;
1-{5-tert-Butyl-2-[5-(2-dimethylamino-ethoxy)-pyridin-3-yl]-2H-pyrazol-3-yl}-3-{4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;
1-{5-tert-Butyl-2-[5-(2-dimethylamino-ethoxy)-pyridin-3-yl]-2H-pyrazol-3-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-{5-tert-Butyl-2-[6-(2-dimethylamino-ethoxy)-pyridin-2-yl]-2H-pyrazol-3-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-[3-tert-Butyl-1'-(2-dimethylamino-ethyl)-1'H-[1,4']bipyrazolyl-5-yl]-3-{-4-[3-(2,6-dichloro-phenyl)-[1,2,4]triazolo[4,3-a]pyridin-6-yloxy]-1,2,3,4-tetrahydro-naphthalen-1-yl}-urea formate salt;
1-[3-tert-Butyl-1'-(2-dimethylamino-ethyl)-1'H-[1,4']bipyrazolyl-5-yl]-3[4-(3-isopropyl-[1,2,4]triazolo[4,3-a]pyridin-6-yloxy)-1,2,3,4-tetrahydro-naphthalen-1-yl]-urea formate salt;
1-[3-tert-Butyl-1'-(2-pyrrolidin-1-yl-ethyl)-1'H-[1,4']bipyrazolyl-5-yl]-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-{3-tert-Butyl-1'-[2-(4-methoxy-piperidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-(3-tert-Butyl-1'-{2-[(2-hydroxy-ethyl)-methyl-amino]-ethyl}-1'H-[1,4']bipyrazolyl-5-yl)-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-{3-tert-Butyl-1'-[2-((S)-3-hydroxy-pyrrolidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;
1-{3-tert-Butyl-1'-[2-(3-methoxy-pyrrolidin-1-yl)-ethyl]-1'H-[1,4']bipyrazolyl-5-yl}-3-{4-[3-(2-methyl-piperi- din-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(ethyl-methyl-amino)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-((S)-2-hydroxymethyl-pyrrolidin-1-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(5-methyl-2,5-diaza-bicyclo[2.2.1]hept-2-yl)-ethyl]-1'H-[1,4']bipyrazolyl-5-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{4-[3-(2-hydroxymethyl-pyrrolidin-1-yl)-[1,2,4]triazolo[4,3-a]pyridin-6-yloxy]-1,2,3,4-tetrahydro-naphthalen-1-yl}-urea;

1-[3-tert-Butyl-1'-(2-hydroxy-ethyl)-1'H-[1,4']bipyrazolyl-5-yl]-3-{4-[3-(1-methyl-pyrrolidin-2-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{4-[3-(1-methyl-pyrrolidin-2-yl)-[1,2,4]triazolo[4,3-a]pyridin-6-yloxy]-1,2,3,4-tetrahydro-naphthalen-1-yl}-urea formate salt; and 1-{5-tert-Butyl-2-[6-(2-dimethylamino-ethoxy)-pyridazin-4-yl]-2H-pyrazol-3-yl}-3-{4-[3-(2-methyl-piperidin-1-yl)-[1,2,4]triazolo[4,3-a]pyridin-6-yloxy]-1,2,3,4-tetrahydro-naphthalen-1-yl}-urea formate salt, or a pharmaceutically acceptable salt of said compound.

2. A compound or pharmaceutically acceptable salt according to claim 1 which is a compound selected from the group consisting of:

1-[3-tert-Butyl-1'-(2-[1,4]oxazepan-4-yl-ethyl)-1'H[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(4-methyl-piperazin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(4-hydroxy-piperidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(3-tert-Butyl-1'-{2-[(methoxy-ethyl)-methyl-amino]-ethyl}-1'H-[1,4']bipyrazolyl-5-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[3-tert-Butyl-1'-(2-piperidin-1-yl-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-[1,4]oxazepan-4-yl-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-[(1S,4R)-4-(3-dimethylamino-[1,2,4]triazolo[4,3-a]pyridin-6-yloxy)-1,2,3,4-tetrahydro-naphthalen-1-yl]-urea formate salt;

1-[3-tert-Butyl-1'-(2-dimethylamino-ethyl)-1'H[1,4']bipyrazolyl-5-yl]-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(3-dimethylamino-propyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[3-(4-methyl-piperazin-1-yl)-propyl]-1'H-[1,4']bipyrazolyl-5-yl}-3-{(1S,4R)-4-[3-((S)-2-methyl-piperidin-1-yl)[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,3']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,3']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt;

1-[5-tert-Butyl-2-(2-dimethylamino-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydronaphthalen-1-yl}-urea formate salt;

1-{5-tert-Butyl-2-[5-(2-dimethylamino-ethoxy)-pyridin-3-yl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy)-1,2,3,4-tetrahydro-naphthalen-1-yl}-urea formate salt;

1-{5-tert-Butyl-2-[5-(2-dimethylamino-ethoxy)-pyridin-3-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{5-tert-Butyl-2-[6-(2-dimethylamino-ethoxy)-pyridin-2-yl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{(1S,4R)-4-[3-(2,6-dichloro-phenyl)-[1,2,4]triazolo[4,3-a]pyridin-6-yloxy)-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3 [(1S,4R)-4-(3-isopropyl-[1,2,4]triazolo[4,3-a]pyridin-6-yloxy)-1,2,3,4-tetrahydro-naphthalen-1-yl]-urea;

1-[3-tert-Butyl-1'-(2-pyrrolidin-1-yl-ethyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(4-methoxy-piperidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-(3-tert-Butyl-1'-{2-[(2-hydroxy-ethyl)-methyl-amino]-ethyl}-1'H-[1,4']bipyrazolyl-5-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-((S)-3-hydroxy-pyrrolidin-1-yl)-ethyl]-1'H-[1,4']bipyrazolyl-5-yl}-3-{(1S,4R)-4-[3-

((S)-2-methyl-piperidin-1-yl)[1,2,4]triazolo[4,3-a]pyridin-6-yloxy]-1,2,3,4-tetrahydro-naphthalen-1-yl}-urea formate salt;

1-{3-tert-Butyl-1'-[2-(3-methoxy-pyrrolidin-1-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-(ethyl-methyl-amino)-ethyl]-1'H-[1,4']bipyrazolyl-5-yl}-3-{(1S,4R)-4-[3-((S)-2-methyl-piperidin-1-yl)[1,2,4]triazolo[4,3-a]pyridin-6-yloxy]-1,2,3,4-tetrahydro-naphthalen-1-yl}-urea formate salt;

1-{3-tert-Butyl-1'-[2-((S)-2-hydroxymethyl-pyrrolidin-1-yl)-ethyl]-1   [1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-{3-tert-Butyl-1'-[2-((1S,4S)-5-methyl-2,5-diaza-bicyclo[2.2.1]hept-2-yl)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea;

1-[3-tert-Butyl-1'-(2-hydroxy-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt;

1-[3-tert-Butyl-1'-(2-dimethylamino-ethyl)-1'H-[1,4']bipyrazolyl-5-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt; and 1-{5-tert-Butyl-2-[6-(2-dimethylamino-ethoxy)-pyridazin-4-yl]-2H-pyrazol-3-yl   1-3-(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt;

or a pharmaceutically acceptable salt of said compound.

3. A compound or pharmaceutically acceptable salt, which is a compound of formula (Ia):

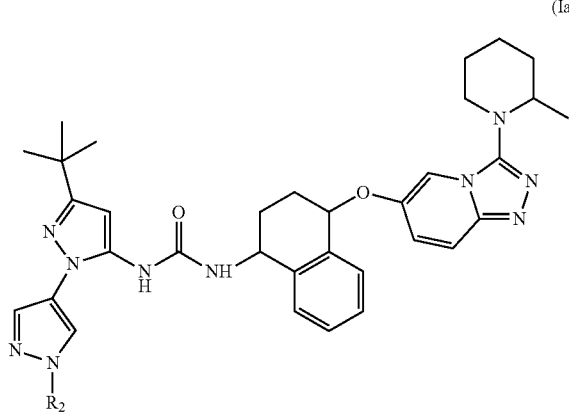

(Ia)

wherein $R_2$ is selected from the group consisting of:
1'-(2-[1,4]oxazepan-4-yl-ethyl);
2-[1,4]oxazepan-4-yl-ethyl;
2-(4-hydroxy-piperidin-1-yl)-ethyl;
{2-[(2-methoxy-ethyl)-methyl-amino]-ethyl};
1'-(2-dimethylamino-ethyl);
1'-(3-dimethylamino-propyl);
1'-[3-(4-methyl-piperazin-1-yl)-propyl];
1'-(2-dimethylamino-ethyl);
1'-(2-pyrrolidin-1-yl-ethyl);
1'-[2-(4-methoxy-piperidin-1-yl)-ethyl];
1'-{2-[(2-hydroxy-ethyl)-methyl-amino]-ethyl};
1'-[2-((S)-3-hydroxy-pyrrolidin-1-yl)-ethyl];
1'-[2-(3-methoxy-pyrrolidin-1-yl)-ethyl];
1'-[2-(ethyl-methyl-amino)-ethyl];
1'-[2-((S)-2-hydroxymethyl-pyrrolidin-1-yl)-ethyl];
1'-[2-((1S,4S)-5-methyl-2,5-diaza-bicyclo[2.2.1]hept-2-yl)-ethyl];
2-[6-(2-dimethylamino-ethoxy)-pyridazin-4-yl], or a pharmaceutically acceptable salt of said compound of formula (Ia).

4. A compound or pharmaceutically acceptable salt, which is a compound of formula (Ib):

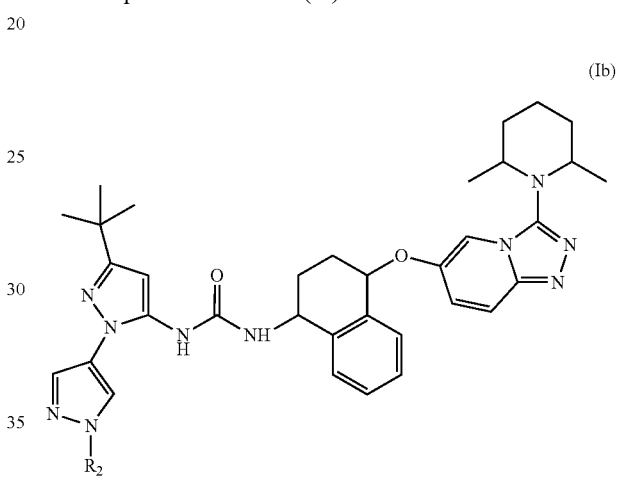

(Ib)

wherein $R_2$ is selected from the group consisting of:
1'-(2-piperidin-1-yl-ethyl);
1'-(2-[1,4]oxazepan-4-yl-ethyl); and
1'-(2-dimethylamino-ethyl), or a pharmaceutically acceptable salt of said compound of formula (Ib).

5. A compound or pharmaceutically acceptable salt, which is a compound of formula (Ic):

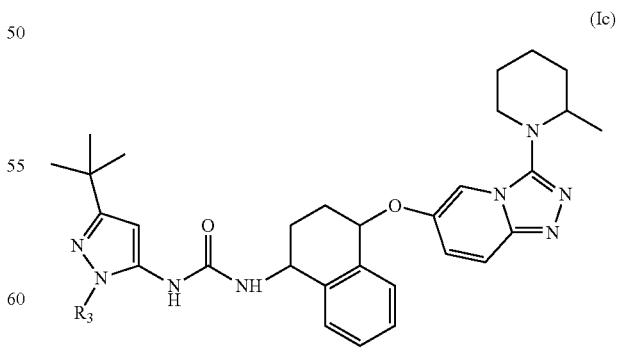

(Ic)

wherein $R_3$ is selected from the group consisting of:
2-[5-(2-dimethylamino-ethoxy)-pyridin-3-yl];
2-[6-(2-dimethylamino-ethoxy)-pyridin-2-yl]; and
2-[6-(2-dimethylamino-ethoxy)-pyridazin-4-yl], or a pharmaceutically acceptable salt of said compound of formula (Ic).

6. A compound or pharmaceutically acceptable salt, which is a compound of formula (Id):

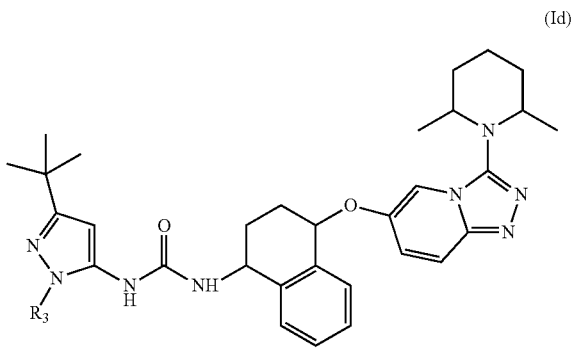

(Id)

wherein R₄ is selected from the group consisting of:
2-(2-dimethylamino-ethyl); and
2-[5-(2-dimethylamino-ethoxy)-pyridin-3-yl],
or a pharmaceutically acceptable salt of said compound of formula (Id).

7. A pharmaceutical composition, comprising a compound or pharmaceutically acceptable salt according to claim 1 and one or more pharmaceutically acceptable carriers.

8. A composition as claimed in claim 7, which is in a form suitable for inhalation for pulmonary administration.

9. A method of treating a disease or condition selected from the group consisting of chronic eosinophilic pneumonia, asthma, COPD, adult respiratory distress syndrome (ARDS), exacerbation of airways hyper-reactivity consequent to other drug therapy, and airways disease that is associated with pulmonary hypertension, comprising administering to a subject in need thereof an effective amount of a compound or pharmaceutically acceptable salt as claimed in claim 1.

10. A method according to claim 9, wherein said disease or condition is asthma, COPD, or adult respiratory distress syndrome (ARDS).

11. A method of treating a disease or condition selected from the group consisting of chronic eosinophilic pneumonia, asthma, COPD, adult respiratory distress syndrome (ARDS), exacerbation of airways hyper-reactivity consequent to other drug therapy, and airways disease that is associated with pulmonary hypertension, comprising administering to a subject in need thereof an effective amount of a compound or pharmaceutically acceptable salt as claimed in claim 2.

12. A method according to claim 11, wherein said disease or condition is asthma, COPD, or adult respiratory distress syndrome (ARDS).

13. A method of treating a disease or condition selected from the group consisting of chronic eosinophilic pneumonia, asthma, COPD, adult respiratory distress syndrome (ARDS), exacerbation of airways hyper-reactivity consequent to other drug therapy, and airways disease that is associated with pulmonary hypertension, comprising administering to a subject in need thereof an effective amount of a compound or pharmaceutically acceptable salt as claimed in claim 3.

14. A method according to claim 13, wherein said disease or condition is asthma, COPD, or adult respiratory distress syndrome (ARDS).

15. A method of treating a disease or condition selected from the group consisting of chronic eosinophilic pneumonia, asthma, COPD, adult respiratory distress syndrome (ARDS), exacerbation of airways hyper-reactivity consequent to other drug therapy, and airways disease that is associated with pulmonary hypertension, comprising administering to a subject in need thereof an effective amount of a compound or pharmaceutically acceptable salt as claimed in claim 4.

16. A method according to claim 15, wherein said disease or condition is asthma, COPD, or adult respiratory distress syndrome (ARDS).

17. A method of treating a disease or condition selected from the group consisting of chronic eosinophilic pneumonia, asthma, COPD, adult respiratory distress syndrome (ARDS), exacerbation of airways hyper-reactivity consequent to other drug therapy, and airways disease that is associated with pulmonary hypertension, comprising administering to a subject in need thereof an effective amount of a compound or pharmaceutically acceptable salt as claimed in claim 5.

18. A method according to claim 17, wherein said disease or condition is asthma, COPD, or adult respiratory distress syndrome (ARDS).

19. A method of treating a disease or condition selected from the group consisting of chronic eosinophilic pneumonia, asthma, COPD, adult respiratory distress syndrome (ARDS), exacerbation of airways hyper-reactivity consequent to other drug therapy, and airways disease that is associated with pulmonary hypertension, comprising administering to a subject in need thereof an effective amount of a compound or pharmaceutically acceptable salt as claimed in claim 6.

20. A method according to claim 19, wherein said disease or condition is asthma, COPD, or adult respiratory distress syndrome (ARDS).

* * * * *